(12) United States Patent
Plotkin et al.

(10) Patent No.: US 11,214,613 B2
(45) Date of Patent: Jan. 4, 2022

(54) EPITOPES IN THE RNA RECOGNITION MOTIF 1 (RRM1) OF TDP-43 AND MISFOLDING-SELECTIVE ANTIBODIES THERETO

(71) Applicant: THE UNIVERSITY OF BRITISH COLUMBIA, Vancouver (CA)

(72) Inventors: Steven S. Plotkin, Vancouver (CA); Neil R. Cashman, Vancouver (CA); Xubiao Peng, Beijing (CN)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/616,832

(22) PCT Filed: May 30, 2018

(86) PCT No.: PCT/CA2018/050634
§ 371 (c)(1),
(2) Date: Nov. 25, 2019

(87) PCT Pub. No.: WO2018/218352
PCT Pub. Date: Dec. 6, 2018

(65) Prior Publication Data
US 2020/0165327 A1      May 28, 2020

Related U.S. Application Data

(60) Provisional application No. 62/595,866, filed on Dec. 7, 2017, provisional application No. 62/570,582, filed
(Continued)

(51) Int. Cl.
*C07K 16/18* (2006.01)
*C07K 5/12* (2006.01)
(Continued)

(52) U.S. Cl.
CPC .............. *C07K 16/18* (2013.01); *C07K 5/12* (2013.01); *C07K 14/4703* (2013.01);
(Continued)

(58) Field of Classification Search
None
See application file for complete search history.

(56) References Cited

U.S. PATENT DOCUMENTS 9,428,575 B2 *   8/2016   Lai ......................... A61P 37/02
10,751,382 B2 *  8/2020   Cashman ............. G01N 33/6896

FOREIGN PATENT DOCUMENTS

WO      1997/012975 A1    4/1997
WO      2010040209 A1     4/2010
(Continued)

OTHER PUBLICATIONS

Igaz, Lionel M. et al. Dysregulation of the ALS-associated gene TDP-43 leads to neuronal death and degeneration in mice. J Clin Invest. Feb. 2011;121(2):726-38.
(Continued)

*Primary Examiner* — Aurora M Fontainhas
(74) *Attorney, Agent, or Firm* — Bereskin & Parr LLP; Carmela De Luca; Amy Dam

(57) ABSTRACT

The disclosure pertains to conformational epitopes in TDP-43, antibodies thereto and methods of making and using immunogens and antibodies specific thereto.

26 Claims, 16 Drawing Sheets
Specification includes a Sequence Listing.

Related U.S. Application Data on Oct. 10, 2017, provisional application No. 62/512,647, filed on May 30, 2017.

(51) Int. Cl.
  *C07K 14/47* (2006.01)
  *G01N 33/68* (2006.01)

(52) U.S. Cl.
  CPC ..... *G01N 33/6872* (2013.01); *C07K 2317/24* (2013.01); *C07K 2317/34* (2013.01); *C07K 2317/565* (2013.01); *C07K 2317/622* (2013.01); *C07K 2317/92* (2013.01)

(56) References Cited

FOREIGN PATENT DOCUMENTS

| | | |
|---|---|---|
| WO | 2011051351 A1 | 5/2011 |
| WO | 2013061163 A2 | 5/2013 |
| WO | 2016053610 A1 | 4/2016 |
| WO | 2016086320 A1 | 6/2016 |
| WO | 2017079836 A1 | 5/2017 |

OTHER PUBLICATIONS

Chen-Plotkin, Alice S. et al. TAR DNA-binding protein 43 in neurodegenerative disease. Nat Rev Neurol., Apr. 2010 ; 6(4):211-220.

Kuo, Pan Hsien et al. The Crystal Structure of TDP-43 RRM1-DNA Complex Reveals the Specific Recognition for UG- and TG-Rich Nucleic Acids. Nucleic Acids Research, 2014, vol. 42, No. 7, 4712-4722.

He, F. et al. Solution Structure of RRM Domain in TAR DNA-binding protein-43. RCSB Protein Data Bank (2004) DOI: 10.2210/pdb1wf0/pdb, 4 pages.

Mompean, Miguel et al. The TDP-43 N-terminal domain structure at high resolution. The FEBS Journal 283 (2016) 1242-1260.

Arai, Tetsuaki et al. TDP-43 is a component of ubiquitin-positive tau-negative inclusions in frontotemporal lobar degeneration and amyotrophic lateral sclerosis. Biochem. Biophys. Res. Commun., 2006, 351, 602-611.

Sephton, Chantelle F. TDP-43 is a Developmentally Regulated Protein Essential for Early Embryonic Development. J. Biol. Chem. vol. 285, No. 9, pp. 6826-6834, Feb. 26, 2010.

Abel, Olubunmi et al. ALSoD: A User-Friendly Online Bioinformatics Tool for Amyotrophic Lateral Sclerosis Genetics. Human Mutattion, vol. 33, No. 9, 1345-1351, 2012.

Hamley, Ian W. PEG-Peptide Conjugates. dx.doi.org/10.1021/bm500246w. Biomacromolecules 2014, 15, 1543-1559.

Roberts, M.J. et al. Chemistry for peptide and protein PEGylation. Advanced Drug Delivery Reviews 54 (2002) 459-476.

Karkan, Delara et al. A Unique Carrier for Delivery of Therapeutic Compounds beyond the Blood-Brain Barrier. PLoS ONE, Jun. 2008, vol. 3, Issue 6, e2469, 14 pages.

Zuchero, Y. Joy Yu et al. Discovery of Novel Blood-Brain Barrier Targets to Enhance Brain Uptake of Therapeutic Antibodies. Neuron 89, 70-82, Jan. 6, 2016.

Webster, Carl I. et al. Brain penetration, target engagement, and disposition of the blood-brain barrier-crossing bispecific antibody antagonist of metabotropic glutamate receptor type 1. The FASEB Journal. vol. 30, May 2016, 14 pages.

\* cited by examiner

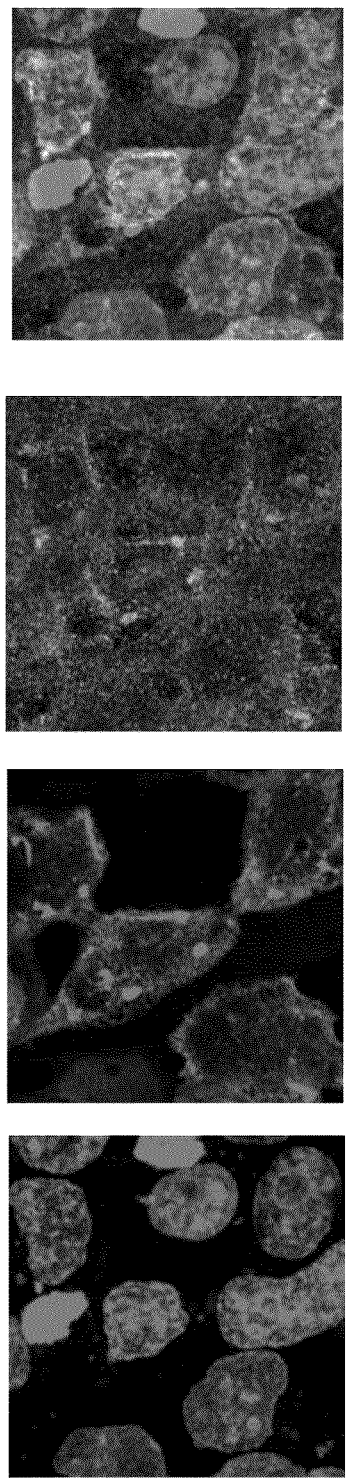

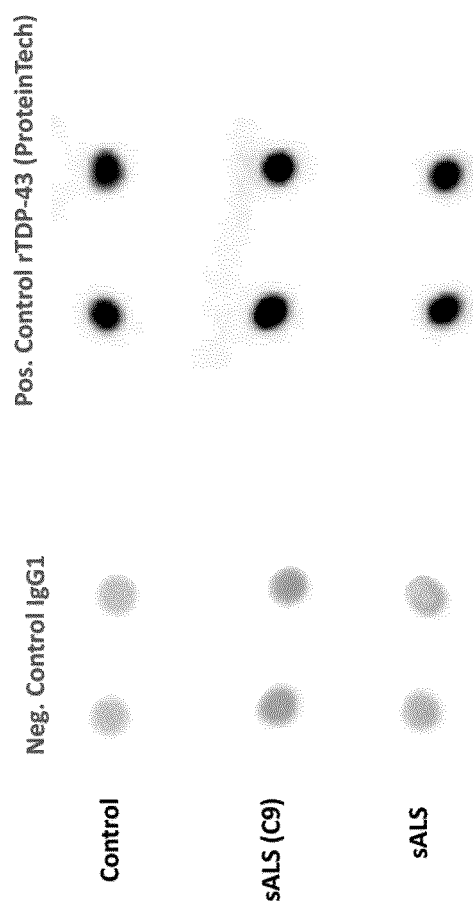
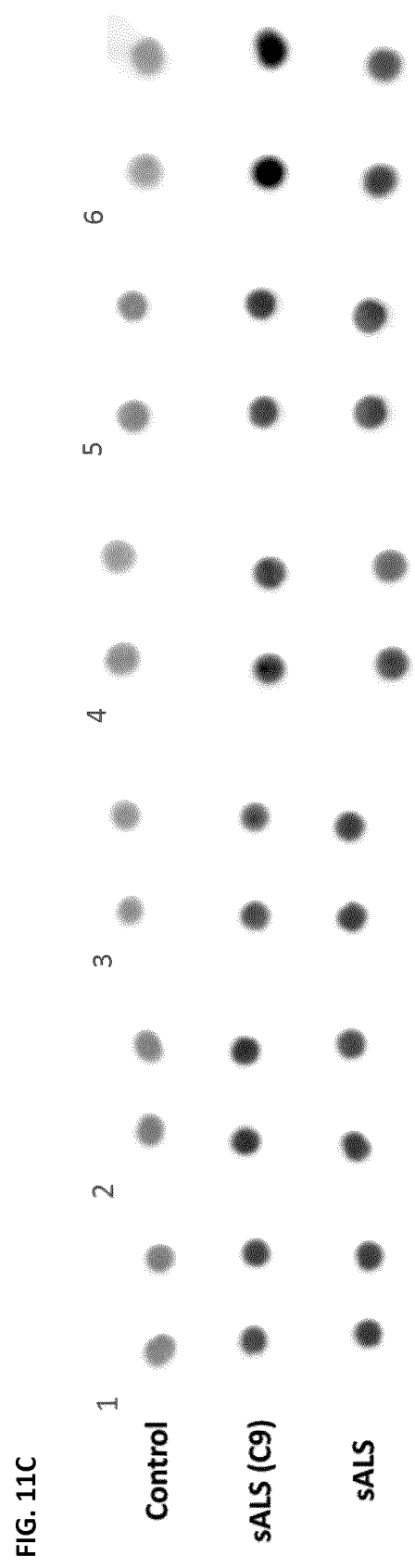

FIG. 13A

```
2H10.1-VH1  EVKLVESGGGLVQPGGSLRLSCATSGFTFSDFYINWVRQPPGKRLEWIATSRSKAHDYTT  60
6C5.1       EVKLVESGGGLVQPGGSLKLSCATSGFTFSDYYMYWVRQTPEKRLEWVAYISNG----GGST  58
9C5.1       EVQLVESGGGLVKPGGSLKLSCAASGFTFSDYYMYWVRQTPEKRLEWVATISDG----GSYT  58
2H10.1-VH2  QVQLQQSGTELVRPGTSVKVSCKASGYAFTNYLIEWVKQRPGQGLEWIGVINPG----SGGT  58
3H5.1       QIQLVQSGPELKKPGETVKISCKASGYTFTDYSMHWVKQAPGKGLKWMGWINTE----TGEP  58
11F3.1      QIQLVQSGPELKKPGETVKISCKASGYTFTDYSMHWVKHSPGKGLKWMGWINTE----TGEP  58
            ::*:**:...::  . ** ::***:******  :  **::*.:*:. :  .        *
                             CDR1                          CDR2

2H10.1-VH1  EYSASVKGRFIVSRDTSQSILYLQMDALKPEDTAIYYCARDTW------YGSWFAYWGQGTL  116
6C5.1       YYPDTVKGRFTISRDNAKNTLYLQMSRLKSEDTAMYCAREG---------GTAWFAYWGQGTL  113
9C5.1       SYPDSVKGRFTISRDNAKNNLYLQMSSLRSEDTAMYCARDYYGSSSYTSGFAYWGQGTL  118
2H10.1-VH2  RYNEKFKGKATLTADKSSTTAHMQLSSLTSDDSAVFYCARW---GGNYSGYAMDYWGQGTS  116
3H5.1       TYADDFKGREAFSLETSASTAYLQINNLKNEDTATYFCASR---R---WYPYYFDYWGQGTT  114
11F3.1      TYADDFKGREAFSLETSASTAYLQINNLKNEDTATYFCAR------GYGNWFAYWGQGTL  112
            . .   :* : : :*.::::  :: : .:: ::: : **         .       ****
                                                              CDR3

2H10-VH1    VTVST121                  2H10.1-VH1  SEQ ID NO: 62
6C5.1       VTVSA118                  6C5.1       SEQ ID NO: 50
9C5.1       VTVSA123                  9C5.1       SEQ ID NO: 54
2H10-VH2    VTVSS121                  2H10.1-VH2  SEQ ID NO: 66
3H5.1       LTVS-118                  3H5.1       SEQ ID NO: 46
11F3.1      VTVSA117                  11F3.1      SEQ ID NO: 58
            :**
```

FIG. 13B

```
3H5.1    QAVVTQ-ESALTTSPGETVTLTCRSSTGAVT---TSNYANWVQEKPDHLFTGLIGGPNNRA    57
11F3.1   QIVLTQSPAIMSASLGERVTMTCTASSSV----SSSYLHWYQQKPGSSPKLWIYSTSNLA    56
2H10.1   DVLMTQTPLSLPVSLGDQASISCRSSQSIVHSNGNTYLEWYLQKPGQSPKLLIYKVSNRF    60
6C5.1    DVLMTQTPLSLPVSLGDQASISCRSSQSIVHSNGNTYLEWYLQKPGQSPKLLIYKVSNRF    60
9C5.1    DVLMTQTPLSLPVSLGDQASISCRSSQSIVHSNGNTYLEWYLQKPGQSPKLLIYKVSNRF    60
            : ::**   *   :**  *  ::*      ..*  * ***  ***:* :* ***
                         CDR1                              CDR2

3H5.1    PGVPARFSGSLIGDKAALTITGAQTEDEAIYFCALWYSNHWVFGGGTKLTVL          109
11F3.1   SGVPARFSGSGSGTSYSLTISSMEAEDAATYYCHQYHRSPLTFGAGTKLELK          108
2H10.1   SGVPDRFSGSGSGTDFTLKISRVEAEDLGVYYCFQGSHVPPTFGGGSKLEIK          112
6C5.1    SGVPDRFSGSGSGTDFTLKISRVEAEDLGVYYCFQGSHVPYTFGGGTKLEIK          112
9C5.1    SGVPDRFSGSGSGTDFTLKISRVEAEDLGVYYCFQGSHVPGTFGGGTKLEIK          112
         ***.********.:*:  **** * * * *::*  *  :* ******:** *
                                           CDR3
```

| | |
|---|---|
| 3H5.1 | SEQ ID NO: 48 |
| 11F3.1 | SEQ ID NO: 60 |
| 2H10.1 | SEQ ID NO: 64 |
| 6C5.1 | SEQ ID NO: 52 |
| 9C5.1 | SEQ ID NO: 56 |

SEQUENCE LISTING

<160> NUMBER OF SEQ ID NOS: 92

<210> SEQ ID NO 1
<211> LENGTH: 4
<212> TYPE: PRT
<213> ORGANISM: Homo Sapiens

```
<400> SEQUENCE: 1

Thr Thr Glu Gln
1

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Cys Gly Gly Thr Thr Glu Gln Gly Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Cys Gly Thr Thr Glu Gln Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gly Thr Thr Glu Gln Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Thr Thr Glu Gln Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Gly Thr Thr Glu Gln
1               5

<210> SEQ ID NO 7
<211> LENGTH: 6
<212> TYPE: PRT
<213> ORGANISM: Homo Sapiens

<400> SEQUENCE: 7

Lys Thr Thr Glu Gln Asp
```

```
1               5

<210> SEQ ID NO 8
<211> LENGTH: 4
<212> TYPE: PRT
<213> ORGANISM: Homo Sapiens

<400> SEQUENCE: 8

Thr Glu Gln Asp
1

<210> SEQ ID NO 9
<211> LENGTH: 5
<212> TYPE: PRT
<213> ORGANISM: Homo Sapiens

<400> SEQUENCE: 9

Thr Thr Glu Gln Asp
1               5

<210> SEQ ID NO 10
<211> LENGTH: 4
<212> TYPE: PRT
<213> ORGANISM: Homo Sapiens

<400> SEQUENCE: 10

Lys Thr Thr Glu
1

<210> SEQ ID NO 11
<211> LENGTH: 6
<212> TYPE: PRT
<213> ORGANISM: Homo Sapiens

<400> SEQUENCE: 11

Thr Thr Glu Gln Asp Leu
1               5

<210> SEQ ID NO 12
<211> LENGTH: 5
<212> TYPE: PRT
<213> ORGANISM: Homo Sapiens

<400> SEQUENCE: 12

Lys Thr Thr Glu Gln
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Cys Gly Thr Thr Glu Gln Gly Cys
1               5

<210> SEQ ID NO 14
<211> LENGTH: 7
<212> TYPE: PRT
<213> ORGANISM: Homo Sapiens

<400> SEQUENCE: 14

Lys Thr Thr Glu Gln Asp Leu
```

```
<210> SEQ ID NO 15
<211> LENGTH: 6
<212> TYPE: PRT
<213> ORGANISM: Homo Sapiens

<400> SEQUENCE: 15

Thr Glu Gln Asp Leu Lys
1               5

<210> SEQ ID NO 16
<211> LENGTH: 7
<212> TYPE: PRT
<213> ORGANISM: Homo Sapiens

<400> SEQUENCE: 16

Thr Glu Gln Asp Leu Lys Glu
1               5

<210> SEQ ID NO 17
<211> LENGTH: 8
<212> TYPE: PRT
<213> ORGANISM: Homo Sapiens

<400> SEQUENCE: 17

Thr Glu Gln Asp Leu Lys Glu Tyr
1               5

<210> SEQ ID NO 18
<211> LENGTH: 9
<212> TYPE: PRT
<213> ORGANISM: Homo Sapiens

<400> SEQUENCE: 18

Thr Glu Gln Asp Leu Lys Glu Tyr Phe
1               5

<210> SEQ ID NO 19
<211> LENGTH: 4
<212> TYPE: PRT
<213> ORGANISM: Homo Sapiens

<400> SEQUENCE: 19

Glu Gln Asp Leu
1

<210> SEQ ID NO 20
<211> LENGTH: 6
<212> TYPE: PRT
<213> ORGANISM: Homo Sapiens

<400> SEQUENCE: 20

Trp Lys Thr Thr Glu Gln
1               5

<210> SEQ ID NO 21
<211> LENGTH: 16
<212> TYPE: PRT
<213> ORGANISM: Homo Sapiens

<400> SEQUENCE: 21

Thr Thr Glu Gln Asp Leu Lys Glu Tyr Phe Ser Thr Phe Gly Glu Val
1               5                   10                  15
```

```
<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Cys Gly Gly Thr Thr Glu Gln Gly Gly Gly
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Cys Gly Thr Thr Glu Gln Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Cys Thr Thr Glu Gln Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Cys Thr Thr Glu Gln Gly Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26

Cys Gly Thr Thr Glu Gln
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Cys Gly Thr Thr Glu Gln
1               5
```

```
<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Cys Gly Thr Thr Glu Gly
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Cys Gly Thr Thr Glu Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Cys Gly Gly Thr Thr Glu Gly Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Cys Gly Gly Gly Thr Thr Glu Gly Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Cys Gly Gly Thr Thr Glu Gly Gly Gly
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Cys Gly Gly Gly Thr Thr Glu Gly Gly Gly
1               5                   10

<210> SEQ ID NO 34
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Cys Gly Gly Gly Gly Thr Thr Glu Gly Gly Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Cys Gly Gly Gly Gly Thr Thr Glu Gly Gly Gly Gly
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Cys Thr Thr Glu Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Cys Thr Thr Glu Gly Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Cys Gly Thr Thr Glu
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct

<400> SEQUENCE: 39

Cys Gly Gly Thr Thr Glu
1               5

<210> SEQ ID NO 40
<211> LENGTH: 5
```

```
<212> TYPE: PRT
<213> ORGANISM: Artificial Sequence
<220> FEATURE:
<223> OTHER INFORMATION: Linker

<400> SEQUENCE: 40

Gly Gly Cys Gly Gly
1               5

<210> SEQ ID NO 41
<211> LENGTH: 4
<212> TYPE: PRT
<213> ORGANISM: Artificial Sequence
<220> FEATURE:
<223> OTHER INFORMATION: Linker

<400> SEQUENCE: 41

Gly Cys Gly Gly
1

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Cys Gly Gly Gly Thr Thr Glu Gln Gly Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Construct

<400> SEQUENCE: 43

Cys Gly Gly Gly Gly Thr Thr Glu Gln Gly Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Construct

<400> SEQUENCE: 44

Cys Gly Gly Gly Gly Thr Thr Glu Gln Gly Gly Gly
1               5                   10

<210> SEQ ID NO 45
<211> LENGTH: 355
<212> TYPE: DNA
<213> ORGANISM: Mus musculus

<400> SEQUENCE: 45
cagatccagt tggtgcagtc tggacctgag ctgaagaagc ctggagagac agtcaagatc      60
tcctgcaagg cttctggtta taccttcaca gactattcaa tgcactgggt gaaacaggct     120
ccaggaaggg tttaaagtgg atgggctgga taaacactga gactggtgag ccaacatatg     180
cagatgactt caagggacgg tttgccttct ctttggaaac ctctgccagc actgcctatt     240
tgcagatcaa caactcaaaa atgaggacac ggctacatat ttctgtgcta gtcgacgatg     300
```
gtacccgtac tactttgact actggggcca aggcaccact ctcacagtct cctca        355

<210> SEQ ID NO 46
<211> LENGTH: 119
<212> TYPE: PRT
<213> ORGANISM: Mus musculus

<400> SEQUENCE: 46

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Arg Arg Trp Tyr Pro Tyr Tyr Phe Asp Tyr Trp Gly Gln Gly
            100                 105                 110

Thr Thr Leu Thr Val Ser Ser
        115

<210> SEQ ID NO 47
<211> LENGTH: 326
<212> TYPE: DNA
<213> ORGANISM: Mus musculus

<400> SEQUENCE: 47
caggctgttg tgactcagga atctgcactc accacatcac ctggtgaaac agtcacactc        60
acttgtcgct caagtactgg ggctgttaca actagtaact atgccaactg gtccaagaa        120 aaaccagatc atttattcac tggtctaata ggtggtccca caaccgagc tccaggtgtt        180 cctgccagat tctcaggctc cctgattgga gacaaggctg ccctcaccat cacagggca        240 cagactgagg atgaggcata tttctgtgc tctatggta cagcaaccat gggtgttcg        300 gtggaggaac aaactgact gtccta                                            326

<210> SEQ ID NO 48
<211> LENGTH: 109
<212> TYPE: PRT
<213> ORGANISM: Mus musculus

<400> SEQUENCE: 48

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Pro Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn

His Trp Val Phe Gly Gly Gly Thr Lys Leu Thr Val Leu
                100                 105

<210> SEQ ID NO 49
<211> LENGTH: 352
<212> TYPE: DNA
<213> ORGANISM: Mus musculus

<400> SEQUENCE: 49
gaagtgaagc tggtggagtc tgggggaggc ttagtgcagc ctggagggtc cctgaaactc       60
tcctgtgcaa cctctggatt cactttcagt gactattaca tgtattgggt tcgccagact      120
ccagagagag gctggagtgg gtcgcataca ttagtaatgg tggtggtagc acctattatc      180
cagacactgt aaagggccga ttcaccatct ccagagacaa tgccaagaac accctgtacc      240
tgcaaatgag ccgttgaagt ctgaggacac agccatgtat tactgtgcaa gagaggggg       300 taccgcctgg tttgcttact ggggccaagg gactctggtc actgtctctg ca              352

<210> SEQ ID NO 50
<211> LENGTH: 118
<212> TYPE: PRT
<213> ORGANISM: Mus musculus

<400> SEQUENCE: 50

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Glu Gly Gly Thr Ala Trp Phe Ala Tyr Trp Gly Gln Gly Thr
            100                 105                 110

Leu Val Thr Val Ser Ala
        115

<210> SEQ ID NO 51
<211> LENGTH: 334
<212> TYPE: DNA
<213> ORGANISM: Mus musculus

<400> SEQUENCE: 51
gatgttttga tgacccaaac tccactctcc ctgcctgtca gtcttggaga tcaagcctcc       60
atctcttgca gatctagtca gagcattgta catagtaatg gaaacaccta tttagaatgg      120
tacctgcgaa accaggccag tctccaaagc tcctgatcta caaagtttcc aaccgatttt      180
ctggggtccc agacaggttc agtggcagtg gatcagggac agatttcaca ctcaagatca      240
gcagagtgga ggctaggatc tgggagtttt ttactgcttt caaggttcac atgttccgta      300
cacgttcgga gggggaccaa gctggaaata aaa                                   334

<210> SEQ ID NO 52

```
<211> LENGTH: 112
<212> TYPE: PRT
<213> ORGANISM: Mus musculus

<400> SEQUENCE: 52

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 53
<211> LENGTH: 367
<212> TYPE: DNA
<213> ORGANISM: Mus musculus

<400> SEQUENCE: 53
gaagtgcagc tggtggagtc tgggggaggc ttagtgaagc ctggagggtc cctgaaactc     60
tcctgtgcag cctctggatt cactttcagt gactattaca tgtattgggt tcgccagact    120
ccggaaagag gctggagtgg gtcgcaacca ttagtgatgg tggtagttac acctcctatc    180
cagacagtgt gaagggacga ttcaccatct ccagagacaa tgccaagaac aacctgtacc    240
tgcaaatgag cagttgaggt ctgaggacac agccatgtat tactgtgcaa gagattacta    300
tggtagtagt agctacacct cgggctttgc ttactggggc caagggactc tggtcactgt    360
ctctgca                                                               367

<210> SEQ ID NO 54
<211> LENGTH: 123
<212> TYPE: PRT
<213> ORGANISM: Mus musculus

<400> SEQUENCE: 54

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Tyr Thr Ser Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Met Tyr Tyr Cys
                85                  90                  95

Ala Arg Asp Tyr Tyr Gly Ser Ser Ser Tyr Thr Ser Gly Phe Ala Tyr
            100                 105                 110

Trp Gly Gln Gly Thr Leu Val Thr Val Ser Ala
```

<210> SEQ ID NO 55
<211> LENGTH: 334
<212> TYPE: DNA
<213> ORGANISM: Mus musculus

<400> SEQUENCE: 55

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcgaa accaggccag tctccaaagc tcctgatcta caaagtttcc aaccgatttt   180
ctggggtccc agacaggttc agtggcagtg gatcagggac agatttcaca ctcaagatca   240
gcagagtgga ggctaggatc tgggagttta ttactgcttt caaggttcac atgttcctgg   300
gacgttcggt ggaggcacca agctggaaat caaa                                334
```

<210> SEQ ID NO 56
<211> LENGTH: 112
<212> TYPE: PRT
<213> ORGANISM: Mus musculus

<400> SEQUENCE: 56

```
Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Gly Thr Phe Gly Gly Gly Thr Lys Leu Glu Ile Lys
            100                 105                 110
```

<210> SEQ ID NO 57
<211> LENGTH: 349
<212> TYPE: DNA
<213> ORGANISM: Mus musculus

<400> SEQUENCE: 57

```
cagatccagt tggtgcagtc tggacctgag ctgaagaagc ctggagagac agtcaagatc    60
tcctgcaagg cttctggtta taccttcaca gactattcaa tgcactgggt gaagcactct   120
ccaggaaggg tttaaagtgg atgggctgga taaacactga gactggtgag ccaacatatg   180
cagatgactt caagggacgg tttgccttct ctttggaaac ctctgccagc actgccatt    240
tgcagatcaa caactcaaaa atgaggacac ggctacatat ttctgtgcta gagggtatgg   300
caactggttt gcttactggg gccaagggac tctggtcact gtctctgca                349
```

<210> SEQ ID NO 58
<211> LENGTH: 117
<212> TYPE: PRT
<213> ORGANISM: Mus musculus

<400> SEQUENCE: 58

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys His Ser Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Tyr Gly Asn Trp Phe Ala Tyr Trp Gly Gln Gly Thr Leu
            100                 105                 110

Val Thr Val Ser Ala
            115

<210> SEQ ID NO 59
<211> LENGTH: 322
<212> TYPE: DNA
<213> ORGANISM: Mus musculus

<400> SEQUENCE: 59
caaattgttc tcacccagtc tccagcaatc atgtctgcat ctctagggga acgggtcacc      60
atgacctgca ctgccagctc aagtgtaagt tccagttact acactggta ccagcagaag     120 ccaggatctc ccccaaactc tggatttata gcacatccaa cctggcttct ggagtcccag     180
ctcgcttcag tggcagtggg tctgggacct cttactctct cacaatcagc agcatggagg     240
ctgaagatgc tgcccttatt actgccacca gtatcatcgt tccccgctca cgttcggtgc     300
tgggaccaag ctggagctga aa                                              322

<210> SEQ ID NO 60
<211> LENGTH: 108
<212> TYPE: PRT
<213> ORGANISM: Mus musculus

<400> SEQUENCE: 60

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Thr Phe Gly Ala Gly Thr Lys Leu Glu Leu Lys
            100                 105

<210> SEQ ID NO 61
<211> LENGTH: 361
<212> TYPE: DNA
<213> ORGANISM: Mus musculus

<400> SEQUENCE: 61

```
gaggtgaagc tggtggaatc tggaggaggc ttggtacagc ctgggggttc tctgagactc    60
tcctgtgcaa cttctgggtt caccttcagt gatttctaca taaactgggt ccgccagcct   120
ccagggagag actggagtgg attgctacaa gtaggagcaa agctcatgat tatacaacag   180
agtacagtgc atctgtgaag ggtcggttca tcgtctccag agacacttcc caaagcatcc   240
tctaccttca gatgatgccc taaaacctga ggacactgcc atttattact gtgcaagaga   300
tacatggtat ggttcctggt ttgcttactg gggccaaggg actctggtca ctgtctctac   360
a                                                                   361
```

<210> SEQ ID NO 62
<211> LENGTH: 121
<212> TYPE: PRT
<213> ORGANISM: Mus musculus

<400> SEQUENCE: 62

```
Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Ser Asp Phe
             20                  25                  30

Tyr Ile Asn Trp Val Arg Gln Pro Pro Gly Lys Arg Leu Glu Trp Ile
         35                  40                  45

Ala Thr Ser Arg Ser Lys Ala His Asp Tyr Thr Thr Glu Tyr Ser Ala
     50                  55                  60

Ser Val Lys Gly Arg Phe Ile Val Ser Arg Asp Thr Ser Gln Ser Ile
 65                  70                  75                  80

Leu Tyr Leu Gln Met Asp Ala Leu Lys Pro Glu Asp Thr Ala Ile Tyr
                 85                  90                  95

Tyr Cys Ala Arg Asp Thr Trp Tyr Gly Ser Trp Phe Ala Tyr Trp Gly
            100                 105                 110

Gln Gly Thr Leu Val Thr Val Ser Thr
        115                 120
```

<210> SEQ ID NO 63
<211> LENGTH: 334
<212> TYPE: DNA
<213> ORGANISM: Mus musculus

<400> SEQUENCE: 63

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcgaa accaggccag tctccaaagc tcctgatcta caaagtttcc aaccgatttt   180
ctggggtccc agacaggttc agtggcagtg gatcaggaac agatttcaca ctcaagatca   240
gcagagtgga ggctaggatc tgggagttta ttactgcttt caaggttcac atgttcctcc   300
gacgttcggt ggaggctcca agctggaaat caaa                               334
```

<210> SEQ ID NO 64
<211> LENGTH: 112
<212> TYPE: PRT
<213> ORGANISM: Mus musculus

<400> SEQUENCE: 64

```
Asp Val Leu Met Thr Gln Thr Pro Leu Ser Leu Pro Val Ser Leu Gly
  1               5                  10                  15
```

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Ser Lys Leu Glu Ile Lys
            100                 105                 110

<210> SEQ ID NO 65
<211> LENGTH: 361
<212> TYPE: DNA
<213> ORGANISM: Mus musculus

<400> SEQUENCE: 65
caggtccagc tgcagcagtc tggaactgaa ctggtgaggc ctgggacttc agtgaaggtg     60
tcctgcaagg cttctggata cgccttcact aattacttga tagagtgggt aaagcagagg    120
cctggacggg ccttgagtgg attggagtga ttaatcctgg aagtggtggt actaggtaca    180
atgagaagtt caagggcaag gcaacactga ctgcagacaa atcctccacc actgcccaca    240
tgcagctcag cagctgacat ctgatgactc tgcggtctat ttctgtgcaa gatgggggg     300 aaactactct ggctatgcta tggactactg gggtcaagga acctcagtca ccgtctcctc    360
a                                                                    361

<210> SEQ ID NO 66
<211> LENGTH: 121
<212> TYPE: PRT
<213> ORGANISM: Mus musculus

<400> SEQUENCE: 66

Gln Val Gln Leu Gln Gln Ser Gly Thr Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Arg Tyr Asn Glu Lys Phe
    50                  55                  60

Lys Gly Lys Ala Thr Leu Thr Ala Asp Lys Ser Ser Thr Thr Ala His
65                  70                  75                  80

Met Gln Leu Ser Ser Leu Thr Ser Asp Asp Ser Ala Val Tyr Phe Cys
                85                  90                  95

Ala Arg Trp Gly Gly Asn Tyr Ser Gly Tyr Ala Met Asp Tyr Trp Gly
            100                 105                 110

Gln Gly Thr Ser Val Thr Val Ser Ser
        115                 120

<210> SEQ ID NO 67
<211> LENGTH: 8
<212> TYPE: PRT
<213> ORGANISM: Mus musculus

<400> SEQUENCE: 67

Gly Tyr Thr Phe Thr Asp Tyr Ser
1               5

<210> SEQ ID NO 68
<211> LENGTH: 8
<212> TYPE: PRT
<213> ORGANISM: Mus musculus

<400> SEQUENCE: 68

Ile Asn Thr Glu Thr Gly Glu Pro
1               5

<210> SEQ ID NO 69
<211> LENGTH: 12
<212> TYPE: PRT
<213> ORGANISM: Mus musculus

<400> SEQUENCE: 69

Ala Ser Arg Arg Trp Tyr Pro Tyr Tyr Phe Asp Tyr
1               5                   10

<210> SEQ ID NO 70
<211> LENGTH: 9
<212> TYPE: PRT
<213> ORGANISM: Mus musculus

<400> SEQUENCE: 70

Thr Gly Ala Val Thr Thr Ser Asn Tyr
1               5

<210> SEQ ID NO 71
<211> LENGTH: 3
<212> TYPE: PRT
<213> ORGANISM: Mus musculus

<400> SEQUENCE: 71

Gly Pro Asn
1

<210> SEQ ID NO 72
<211> LENGTH: 9
<212> TYPE: PRT
<213> ORGANISM: Mus musculus

<400> SEQUENCE: 72

Ala Leu Trp Tyr Ser Asn His Trp Val
1               5

<210> SEQ ID NO 73
<211> LENGTH: 8
<212> TYPE: PRT
<213> ORGANISM: Mus musculus

<400> SEQUENCE: 73

Gly Phe Thr Phe Ser Asp Tyr Tyr
1               5

<210> SEQ ID NO 74
<211> LENGTH: 8
<212> TYPE: PRT
<213> ORGANISM: Mus musculus

<400> SEQUENCE: 74

Ile Ser Asn Gly Gly Gly Ser Thr

```
<210> SEQ ID NO 75
<211> LENGTH: 11
<212> TYPE: PRT
<213> ORGANISM: Mus musculus

<400> SEQUENCE: 75

Ala Arg Glu Gly Gly Thr Ala Trp Phe Ala Tyr
1               5                   10

<210> SEQ ID NO 76
<211> LENGTH: 11
<212> TYPE: PRT
<213> ORGANISM: Mus musculus

<400> SEQUENCE: 76

Gln Ser Ile Val His Ser Asn Gly Asn Thr Tyr
1               5                   10

<210> SEQ ID NO 77
<211> LENGTH: 3
<212> TYPE: PRT
<213> ORGANISM: Mus musculus

<400> SEQUENCE: 77

Lys Val Ser
1

<210> SEQ ID NO 78
<211> LENGTH: 9
<212> TYPE: PRT
<213> ORGANISM: Mus musculus

<400> SEQUENCE: 78

Phe Gln Gly Ser His Val Pro Tyr Thr
1               5

<210> SEQ ID NO 79
<211> LENGTH: 8
<212> TYPE: PRT
<213> ORGANISM: Mus musculus

<400> SEQUENCE: 79

Ile Ser Asp Gly Gly Ser Tyr Thr
1               5

<210> SEQ ID NO 80
<211> LENGTH: 16
<212> TYPE: PRT
<213> ORGANISM: Mus musculus

<400> SEQUENCE: 80

Ala Arg Asp Tyr Tyr Gly Ser Ser Ser Tyr Thr Ser Gly Phe Ala Tyr
1               5                   10                  15

<210> SEQ ID NO 81
<211> LENGTH: 9
<212> TYPE: PRT
<213> ORGANISM: Mus musculus

<400> SEQUENCE: 81

Phe Gln Gly Ser His Val Pro Gly Thr
1               5
```

<210> SEQ ID NO 82
<211> LENGTH: 10
<212> TYPE: PRT
<213> ORGANISM: Mus musculus

<400> SEQUENCE: 82

Ala Arg Gly Tyr Gly Asn Trp Phe Ala Tyr
1               5                   10

<210> SEQ ID NO 83
<211> LENGTH: 7
<212> TYPE: PRT
<213> ORGANISM: Mus musculus

<400> SEQUENCE: 83

Ser Ser Val Ser Ser Ser Tyr
1               5

<210> SEQ ID NO 84
<211> LENGTH: 3
<212> TYPE: PRT
<213> ORGANISM: Mus musculus

<400> SEQUENCE: 84

Ser Thr Ser
1

<210> SEQ ID NO 85
<211> LENGTH: 9
<212> TYPE: PRT
<213> ORGANISM: Mus musculus

<400> SEQUENCE: 85

His Gln Tyr His Arg Ser Pro Leu Thr
1               5

<210> SEQ ID NO 86
<211> LENGTH: 8
<212> TYPE: PRT
<213> ORGANISM: Mus musculus

<400> SEQUENCE: 86

Gly Phe Thr Phe Ser Asp Phe Tyr
1               5

<210> SEQ ID NO 87
<211> LENGTH: 10
<212> TYPE: PRT
<213> ORGANISM: Mus musculus

<400> SEQUENCE: 87

Ser Arg Ser Lys Ala His Asp Tyr Thr Thr
1               5                   10

<210> SEQ ID NO 88
<211> LENGTH: 12
<212> TYPE: PRT
<213> ORGANISM: Mus musculus

<400> SEQUENCE: 88

Ala Arg Asp Thr Trp Tyr Gly Ser Trp Phe Ala Tyr
1               5                   10

<210> SEQ ID NO 89

```
<211> LENGTH: 8
<212> TYPE: PRT
<213> ORGANISM: Mus musculus

<400> SEQUENCE: 89

Gly Tyr Ala Phe Thr Asn Tyr Leu
1               5

<210> SEQ ID NO 90
<211> LENGTH: 8
<212> TYPE: PRT
<213> ORGANISM: Mus musculus

<400> SEQUENCE: 90

Ile Asn Pro Gly Ser Gly Gly Thr
1               5

<210> SEQ ID NO 91
<211> LENGTH: 14
<212> TYPE: PRT
<213> ORGANISM: Mus musculus

<400> SEQUENCE: 91

Ala Arg Trp Gly Gly Asn Tyr Ser Gly Tyr Ala Met Asp Tyr
1               5                   10

<210> SEQ ID NO 92
<211> LENGTH: 9
<212> TYPE: PRT
<213> ORGANISM: Mus musculus

<400> SEQUENCE: 92

Phe Gln Gly Ser His Val Pro Pro Thr
1               5
```

EPITOPES IN THE RNA RECOGNITION MOTIF 1 (RRM1) OF TDP-43 AND MISFOLDING-SELECTIVE ANTIBODIES THERETO

RELATED APPLICATIONS

This is a Patent Cooperation Treaty Application which claims the benefit of 35 U.S.C. § 119 based on the priority of U.S. Provisional Patent Application Nos. 62/512,647, filed May 30, 2017; 62/570,582, filed Oct. 10, 2017; and 62/595,866, filed Dec. 7, 2017; each of these applications being incorporated herein in their entirety by reference.

INCORPORATION OF SEQUENCE LISTING

A computer readable form of the Sequence Listing "P51866PC00_ST25" (29,211 bytes), submitted via EFS-WEB and created on May 30, 2018, is herein incorporated by reference.

FIELD

The present disclosure relates to TDP-43 epitopes and antibodies thereto and more specifically to conformational TDP-43 epitopes that are predicted to be selectively accessible in misfolded TDP-43, and related antibody compositions.

BACKGROUND

Transactive response (TAR) element DNA binding protein of 43 kDa (TDP-43), is a 414 amino acid protein, and is comprised of an N-terminal ubiquitin like domain (NTD, residues 1-102), two RNA recognition motifs (RRMs) composed of residues 106-177 (RRM1), and residues 192-259 (RRM2), and a C-terminal domain (CTD, residues 274-414). The NTD contains a nuclear localization signal (NLS, residues 82-98). RRM2 includes a nuclear export signal (NES) from residue 239 to 250.

TDP-43 is predominantly a nuclear protein that plays a central role in RNA metabolism. TDP-43 has become a focal point of research in the amyotrophic lateral sclerosis (ALS) and frontotemporal dementia (FTD) disease spectrum, since pathogenic inclusions within affected neurons can contain post-translationally modified TDP-43. The CTD of TDP-43 is particularly relevant to disease, as it is where nearly all familial ALS/FTD-associated mutations are found in TDP-43.

Other mutations include D169G which is located in RRM1 between beta strands 4 and 5, A90V which is a mutation in the NLS region, and the mutations K263E and N267S which are in the linker between RRM2 and the C-terminal domain.

RRM1 and RRM2 have been structurally determined by NMR. For example, RRM1 is available in the Protein Data Bank (PDB), a database of atomic resolution three dimensional structural data, as PDB entry 4IUF, while RRM2 is available as PDB entry 1WF0, and the NTD is available as PDB entry 2N4P.

The structure of 4IUF is reported in Kuo et al. [1]. The structure of 1WF0 is reported in He et al [2]. The structure of 2N4P is reported in Mompean et al. [3].

TDP-43 was found to be hyperphosphorylated, ubiquitinated, and fragmented in neuronal inclusions of patients with both sporadic and familial forms of ALS and FTD [4].

Aggregates of TDP-43 have now been found in nearly all (approx. 97%) cases of ALS and roughly half (approx. 45%) of the cases of FTD. TDP-43 is one of the main components of the cytoplasmic inclusions found in the motor neurons of ALS patients.

Pathological precursors of TDP-43 inclusions may have concentration far below that of functional TDP-43. The low concentration of misfolded TDP-43 makes this target elusive. Antibodies or drugs targeting healthy TDP-43 could be fatal for the cell. TDP-43 is an RNA regulatory protein that is essential for embryonic development [5].

Antibodies that bind TDP-43 have been described.

WO2012174666 titled METHODS FOR THE PROGNOSTIC AND/OR DIAGNOSTIC OF NEURODEGENERATIVE DISEASE, METHODS TO IDENTIFY CANDIDATE COMPOUNDS AND COMPOUNDS FOR TREATING NEURODEGENERATIVE DISEASE discloses methods for diagnosing neurodegenerative diseases such as ALS and FTD through assessing the interaction between TDP-43 and NF-κB p65 using an anti-TDP-43 antibody.

WO2016086320 titled TDP-43-BINDING POLYPEPTIDES USEFUL FOR THE TREATMENT OF NEURODEGENERATIVE DISEASES disclose antibodies that binds to the RRM1 domain of TDP-43 to disrupt its interaction with NF-κB for the treatment of ALS and FTD.

Antibodies that preferentially or selectively bind misfolded TDP-43 over natively folded TDP-43 are desirable.

SUMMARY

Described herein is a conformational epitope in TDP-43 comprising and/or consisting of residues TTEQ (SEQ ID NO: 1) or a part thereof, and antibodies thereto. The epitope is identified as an epitope that may be selectively exposed in the misfolded species of TDP-43, in a conformation that distinguishes it from that in the native protein.

An aspect includes a compound, optionally a cyclic compound comprising: a TDP-43 peptide comprising 1) TTE 2) TTEQ (SEQ ID NO:1); 3) TEQ or a part thereof and up to 6 TDP-43 contiguous residues, and a linker, wherein the linker is covalently coupled to the TDP-43 peptide N-terminus residue and/or the peptide C-terminus residue, wherein at least one amino acid in the TDP-43 peptide is an alternate conformation than T, E, and/or Q in a corresponding linear and/or native TDP-43.

In an embodiment, the TDP-43 peptide is selected from TTEQ (SEQ ID NO: 1), TTE, TEQ, KTTE (SEQ ID NO: 10), KTTEQ (SEQ ID NO:12). TEQD (SEQ ID NO:8) or TTEQD (SEQ ID NO: 9), optionally wherein the cyclic compound is a compound selected from any one of SEQ ID NOs: 2, 3, 13, 22-39, and 42-44.

In an embodiment, the cyclic compound is selected from a cyclic structure described herein, preferably wherein the cyclic compound has a sequence selected from any one of SEQ ID NOs: 2, 3, 13, 22-39, and 42-44, more preferably SEQ ID NOs: 2, 3, 22, 23, 28, 29, 30, 31, 32, 33, 34, 35 and 42, optionally a sequence selected from any one of SEQ ID NOs: 28, 29, 30, 31, 32, 33, 34, 35 and 42 or a sequence selected from SEQ ID NO: 2, 3, 22, 23 and 42.

Also provided in another aspect is an immunogen comprising a cyclic compound described herein.

In an embodiment, the cyclic compound, is coupled to a carrier protein or immunogenicity enhancing component and/or formulated with an adjuvant.

In an embodiment, the carrier protein is bovine serum albumin (BSA) or the immunogenicity-enhancing component is keyhole limpet haemocyanin (KLH) and/or the adjuvant is selected from aluminum phosphate, aluminum hydroxide alum, monophosphoryl lipid A and QS21.

Another aspect provides an antibody that selectively binds an epitope in the TDP-43 peptide in the cyclic compound described herein compared to a corresponding linear compound and/or native TDP-43 polypeptide.

In an embodiment, the antibody selectively binds to a cyclic compound comprising 1) TTE, 2) TEQ, 3) TTEQ (SEQ ID NO:1), 4) KTTE, (SEQ ID NO: 10), 5) KTTEQ (SEQ ID NO:12). 6) TEQD (SEQ ID NO:8) and/or 7) TTEQD (SEQ ID NO: 9) compared to a corresponding linear compound and/or native TDP-43 polypeptide.

In another embodiment, the antibody is at least 2 fold, 3 fold, at least 5 fold, at least 10 fold or at least 20 fold, more selective for the cyclic compound compared to a corresponding linear compound and/or native TDP-43 polypeptide.

Also provided in an embodiment is an antibody that competes for binding misfolded TDP-43 or a cyclic peptide comprising the same or overlapping TDP-43 peptide as an antibody described herein, preferably one that shares at least 80%, or more sequence identity to a heavy chain and/or light chain variable region provided in Table 10.

In an embodiment, the antibody is raised or screened using a cyclic compound or an immunogen described herein.

In an embodiment, the antibody comprises a set of CDRs as described for example in Table 10.

In another embodiment, the antibody comprises a heavy chain variable region comprising: i) an amino acid sequence as set forth in Table 10; ii) an amino acid sequence with at least 50%, at least 60%, at least 70%, at least 80% or at least 90% sequence identity to said heavy chain variable region sequence, wherein the CDR sequences are as set forth in said heavy chain variable region sequence, or iii) a conservatively substituted amino acid sequence of i); and/or wherein the antibody comprises a light chain variable region comprising i) an amino acid sequence as set forth in Table 10, ii) an amino acid sequence with at least 50%, at least 60%, at least 70%, at least 80% or at least 90% sequence identity to said light chain variable region sequence wherein the CDR sequences are as set forth in said light chain variable region sequence, or iii) a conservatively substituted amino acid sequence of i); optionally wherein the heavy chain variable region amino acid sequence is encoded by a nucleotide sequence as set out in Table 10 or a codon degenerate or optimized version thereof and/or wherein the light chain variable region amino acid sequence is encoded by a nucleotide sequence as set out in Table 10 or a codon degenerate or optimized version thereof.

In another embodiment, the antibody is a monoclonal antibody, humanized antibody and/or a single chain antibody or a binding fragment of any of the foregoing.

Another aspect includes an immunoconjugate comprising the antibody descried herein and a detectable label or a transport moiety, optionally a molecule that facilitates transport across the blood brain barrier and/or into a cell.

A further aspect provides a nucleic acid encoding the amino acid residues of the compound, immunogen, antibody or proteinaceous immunoconjugate described herein, or any part thereof.

Another aspect provides a cell expressing an antibody described herein, optionally wherein the cell is a hybridoma.

Another aspect is a composition comprising a cyclic compound, immunogen, antibody, immunoconjugate, nucleic acid or cell described herein, optionally with a diluent.

In an embodiment, the composition comprises a cyclic compound or immunogen described herein and an adjuvant.

In an embodiment, the adjuvant is aluminum phosphate, aluminum hydroxide aluminum hydroxide alum, monophosphoryl lipid A and/or QS21.

Also provided is a kit comprising one or more components described herein for example a compound, immunogen, antibody, immunoconjugate, nucleic acid, cell or composition described herein.

Also provides in another aspect is a method of making the antibody described herein, comprising administering an immunogen described herein or a composition comprising the immunogen to a subject and isolating antibody and/or cells expressing antibody selective or specific for the TDP43 peptide of the immunogen administered.

A further aspect includes a method of determining if a sample suspected of comprising misfolded TDP-43 polypeptides contains misfolded TDP-43 polypeptide the method comprising:

contacting the sample with an antibody described herein under conditions permissive for forming an antibody: misfolded TDP-43 polypeptide complex; and detecting the presence of any complex;

wherein the presence of detectable complex is indicative that the sample may contain misfolded TDP-43 polypeptide.

In an embodiment, the sample comprises brain tissue extract, spinal cord tissue and/or CSF. In another embodiment, the sample is a human sample, optionally from a subject with or suspected of having ALS or FTD.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 1A, is a graph that represents the epitope predictions arising from native structure PDB 4IUF, using the increase in SASA ($\Delta$SASA) as a criterion to choose epitopes. The TTE epitope emerges as a prediction for PDB structure 4IUF. FIG. 1 B is a graph that shows the epitope predictions arising from structure PDB 4IUF, using the loss of native contacts as a criterion for epitope choice. The TTEQ epitope (SEQ ID NO: 1) emerges as a prediction using this metric. FIG. 1C shows several metrics, including increased SASA ($\Delta$SASA), increased root mean squared fluctuations (RMSF) of the atomic positions, which represents the increased dynamics of the epitope, and the decrease in the number of native contacts, $\Delta$contacts. These 3 different metrics predict epitopes TTE, TTE, and TTEQ (SEQ ID NO: 1) respectively.

Figure 1A:
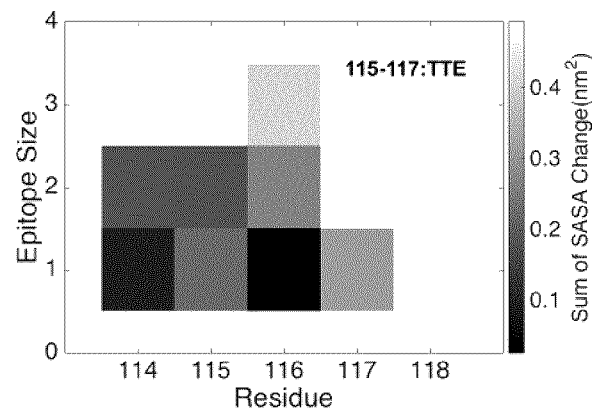
FIGS. 1A to C are graphs plotting different metrics used to predict exposure of an epitope in misfolded TDP-43.

"Wild type" as used herein refers to the primary amino acid sequence of non-mutant or naturally occurring protein.

"Native" as used herein refers to the normal three dimensional structure of a specific protein or part thereof (e.g. the atomic level coordinates of the crystal structure of native TDP-43 RRM1 domain is available at Protein Data Bank Accession Number 4IUF). Native TDP-43 is optionally referred to as "natively folded" TDP-43 "normally folded" TPD-43 and/or "healthy" TDP-43. Similarly native RRM1 domain of TDP-43 is optionally referred to as "natively folded" RRM1 domain of TDP-43 or "normally folded" RRM1 domain of TPD-43. Accordingly the term "native TDP-43 ", or "natively folded TDP-43", herein refers to TDP-43 as natively folded after nascent translation and/or dimeric TDP-43 as folded in non-disease states (e.g. healthy cells) with a molecular structure that comprises a non-covalently associated, individual TDP-43 peptide which shows native structure under in x-ray crystallography or as reconstructed from a nuclear magnetic resonance measurement. The native structure of RRM1 has an alpha/beta structure, consisting of both alpha helices and beta sheets.

"Misfolded" as used herein refers to the secondary and tertiary structure of a polypeptide or part thereof, and indicates that the polypeptide has adopted a conformation that is not normal for that polypeptide in its properly functioning state. Although misfolding can be caused by mutations in a protein, such as amino acid deletion, substitution, or addition, wild-type sequence protein can also be misfolded in disease, and expose disease-specific epitopes for instance, as a result of microenvironmental conditions and/or amino acid modification such as nitration, oxidation, carbonylation or other modification. Other post-translational modifications include aberrant ubiquitination, phosphorylation, acetylation, sumoylation, and cleavage into C-terminal fragments ubiquitylation. Accordingly, "misfolded TDP-43 polypeptide", or "misfolded TDP-43" when referring to the polypeptide herein refers to TDP-43 polypeptide that displays a plurality of conformations of TDP-43 wherein the conformations are partially-ordered, containing parts of the native structure, and partially-disordered, containing polymer segments of amino acids that have alternate conformations than native TDP-43, and often show an increase in SASA, and sample a more diverse conformational ensemble than that explored in the native equilibrium ensemble.

Misfolded TDP-43 is prone to the formation of aggregates resulting in a loss of protein function, toxicity and propagation of pathogenic aggregates.

The term "mutant TDP-43" refers to forms of TDP-43, and particularly endogenous forms of TDP-43 that occur as a result of genetic mutation that result for instance in amino acid substitution, such as those substitutions characteristic for instance of FTD or familial ALS including for example the mutations described in the bioinformatics tool described in [6].

The term "TTEQ (SEQ ID NO: 1)" means the amino acid sequence: threonine, threonine, glutamic acid, glutamine; as shown in SEQ ID NO: 1. Similarly TTE, TEQ, KTTE (SEQ ID NO:10), KTTEQD (SEQ ID NO: 7), TTEQD (SEQ ID NO: 9), TTEQDL (SEQ ID NO: 11), TEQD (SEQ ID NO: 8) refer to the amino acid sequences identified by the 1-letter amino acid code. Depending on the context, the reference of the amino acid sequence can refer to a sequence in TDP-43 or an isolated peptide, such as the amino acid sequence of a cyclic compound. The sequence TTEQ (SEQ ID NO: 1) consists of residues 115-118 in the amino acid primary sequence.

The term "TTEQ (SEQ NO: 1) or a related epitope and/or part of any of the foregoing" as used herein minimally comprises amino acid T115 and/or T116 and/or E117, and includes for example TTE, KTT or TEQ. Reference to TTEQ (SEQ NO: 1) or a related epitope and/or part of any of the foregoing can refer to the region on TDP-43 that is bound by an antibody raised for example by a cyclic compound comprising a TDP-43 peptide sequence. For example the antibody may selectively or specifically bind T115, T116 or E117, a particular part of T115 and/or T116 and/or E117, or a combination of any of the foregoing. Alternatively, it can refer to the TDP-43 peptide sequence that is comprised in a cyclic compound for making antibodies.

The term "alternate conformation than occupied by 115T, 116T, 117E and/or 118Q in the native" as used herein means having one or more differing conformational properties selected from solvent accessibility, (e.g. in the context of a peptide comprising TTEQ (SEQ ID NO: 1) as measured for example in the cyclic peptide described in the examples, RMSD structural alignment, and dihedral angle of one or more backbone or side chain dihedral angles compared to said property for 115T, 116T, 117E and/or 118Q in the TDP-43 native structural ensemble, as shown for example in PDB 4IUF, and shown in the Figures, and/or in the Tables. Similarly, the term "alternate conformation" than occupied by one or more of the T's, E and/or Q in the native structure as used herein means having one or more differing conformational properties selected from solvent accessibility, (e.g. in the context of a corresponding linear peptide comprising TTEQ (SEQ ID NO: 1) or TTE, and dihedral angle of one or more backbone or side chain dihedral angles compared to said property for one or more of T, E and/or Q, for example T, E and/or Q in native TDP-43 as shown for example in PDB 4IUF and shown in FIGS. 1-9 and/or in the Tables. For example, according to FIG. 2, for residue 115T, dihedrals C—CA-CB-OG1 and C—CA-N—HN distinguish both cyclic peptide cyclo(CGGTTEQGG) (SEQ ID NO:2) and the biased ensemble from the corresponding dihedral angles in the native. Specifically, for example, dihedral C—CA-CB-OG1 shows a peak at 180 degrees for cyclic and biased ensembles that is not present in the native ensemble.

An "epitope" as used herein means a region of a protein that is recognized by a B cell or T-cell receptor, or an antibody or a binding fragment thereof. The epitope is optionally represented herein by a linear amino acid sequence or the region of the protein recognized by the antibody. An epitope can comprise one or more antigenic determinants. For example an antibody generated against an isolated peptide corresponding to a misfolded epitope recognizes part or all of said epitope sequence.

As used herein, the term "misfolded epitope" or "conformational epitope" refers to a sequence of amino acids or an antigentic determinant thereof that have a particular three-dimensional structure wherein at least an aspect of the three-dimensional structure not present in a corresponding native structure is recognized by the cognate antibody. The "misfolded- or conformational epitope" becomes exposed or accessible in the misfolded protein (e.g. as present in ALS and FTD). Antibodies which selectively bind a misfolded epitope recognize the spatial arrangement of one or more of the amino acids of that conformation-specific epitope. For example, a TTEQ (SEQ ID NO: 1) conformational epitope refers to an epitope of TTEQ (SEQ ID NO: 1) that is recognized by antibodies selectively, for example at least 2 fold, 3 fold, 5 fold, 10 fold, 50 fold, 100 fold, 250 fold, 500 fold or 1000 fold or greater more selectivity as compared to the epitope on native TDP-43 or for example antibodies raised using a linear peptide comprising TTEQ (SEQ ID NO: 1).

The term "analog" as used herein includes parts, extensions, substitutions, variants, modifications or chemical equivalents and derivatives thereof of the amino acid and nucleotide sequences of the present invention that perform substantially the same function as the peptide, protein or nucleic acid molecules of described herein in substantially the same way. Analogs of the cyclic compounds such as the cyclic peptides also include additions and deletions to the TDP-43 peptides. Analogs of nucleic acids include degenerate nucleotide substitutions that encode an isolated peptide of the invention. In addition, analog peptides and analog nucleotide sequences include derivatives thereof.

The term "amino acid" includes all of the naturally occurring amino acids as well as modified L-amino acids. The atoms of the amino acid can for example include different isotopes. For example, the amino acids can comprise deuterium substituted for hydrogen, nitrogen-15 substituted for nitrogen-14, and carbon-13 substituted for carbon-12 and other similar changes.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-group size for one another. Examples of conservative amino acid substitution include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word length=12 to obtain nucleotide sequences homologous to a nucleic acid molecules of the present application. BLAST protein searches can be performed with the XBLAST program parameters set, e.g., to score-50, word length=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT or other (e.g. Kabat numbering convention). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "antibody" as used herein is intended to include monoclonal antibodies, polyclonal antibodies, single chain, humanized and other chimeric antibodies as well as binding fragments thereof. The antibody may be from recombinant sources and/or produced in transgenic animals. Also included are human antibodies that can be produced through using biochemical techniques or isolated from a library. Humanized or chimeric antibody may include sequences from one or more than one isotype or class.

The phrase "isolated antibody" refers to antibody produced in vivo or in vitro that has been removed from the source that produced the antibody, for example, an animal, hybridoma or other cell line (such as recombinant cells that produce antibody). The isolated antibody is optionally "purified", which means at least: 80%, 85%, 90%, 95%, 98% or 99% purity.

The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

The terms "IMGT numbering" or "ImMunoGeneTics database numbering", which are recognized in the art, refer to a system of numbering amino acid residues which are more variable (i.e. hypervariable) than other amino acid residues in the heavy and light chain variable regions of an antibody, or antigen binding portion thereof.

The CDR sequences referred to herein are based IGBlast identification which searches sequences with BLAST against the IMGT or NCBI germline V gene database. The sequences were also confirmed to correspond to IMGT numbering. As the full sequences for the variable regions are provided, it is possible to identify the CDRs based on other conventions such as Kabat as well.

When an antibody is said to bind to an epitope within specified residues, such as TTEQ (SEQ ID NO:1), what is meant is that the antibody selectively or specifically binds to a polypeptide containing the specified residues or a part thereof for example at least 1 residue or at least 2 residues in a conformation-selective manner. Such an antibody does not necessarily contact every residue of TTEQ (SEQ ID NO:1), and every single amino acid substitution or deletion within said epitope does not necessarily significantly affect or equally affect binding affinity.

The term "detectable label" as used herein refers to moieties such as peptide sequences, fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "epitope selectively presented or accessible in misfolded TDP-43" as used herein refers to an epitope that is selectively presented or accessible on misfolded TDP-43 as present in ALS or FTD (e.g. disease associated misfolded TDP-43) whether in monomeric, dimeric or aggregated forms, but not on the molecular surface of the native, correctly folded, homodimeric form of TDP-43.

The phrase as used herein "epitope consists of TTEQ", indicates an epitope, optionally a conformational epitope, that is bound specifically and preferentially by an antibody that preferentially binds TTEQ (SEQ ID NO: 1) peptide compared to a mutated TTEQ (SEQ ID NO: 1) peptide where any one or more of the residues are mutated for example to alanine. Similarly, the phrase as used herein of "conformational epitope consists of TTEQ" indicates an epitope that is bound specifically by an antibody that preferentially binds TTEQ (SEQ ID NO: 1) in a particular conformation (e.g. misfolded protein, cyclic compound or some other constrained conformation) over another conformation (e.g. native) and optionally over, when at least one or more of the residues, are mutated to for example alanine (e.g cyclic conformation of a peptide comprising TTEQ (SEQ ID NO: 1), versus cyclic conformation of a peptide wherein one or more of the residues are mutated).

The phrase "epitope consisting of TTEQ or a part thereof" indicates an epitope that is bound specifically by an antibody that specifically and preferentially binds TTEQ (SEQ ID NO: 1) peptide compared to a peptide when at least one or more of the residues, optionally 115T, 116T, 117E and/or 118Q, are mutated to alanine or absent. Similarly, the phrase as used herein of "conformational epitope consists of TTEQ or a part thereof" indicates an epitope that is bound specifically by an antibody that preferentially binds TTEQ (SEQ ID NO: 1) or a part thereof when it is in a particular conformation (e.g. misfolded protein, cyclic, or some other constrained conformation) over another conformation (e.g. native conformation) and optionally over, when at least one or more of the residues, optionally 115T, 116T, 117E and/or 118Q, are mutated to alanine or absent (e.g cyclic conformation of a peptide comprising TTEQ (SEQ ID NO: 1), versus cyclic conformation of a peptide wherein one or more of the residues are mutated or absent).

The term "greater affinity" as used herein refers to a degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as KA equal to $1/K_D$ where $K_D$ is equal to $k_{on}/k_{off}$. The $k_{on}$ and $k_{off}$ values can be measured using surface plasmon resonance (measurable for example using a Biacore system).

Also as used herein, the term "immunogenic" refers to substances which elicit the production of antibodies, activate T-cells and other reactive immune cells directed against an antigenic portion of the immunogen.

An "immunogen" as used herein means a substance which provokes an immune response and/or causes production of an antibody. In addition to immunogenic compounds, conjugates and fusions described herein, including for example the isolated compounds conjugated to KLH, peptide mimetics which elicit cross-reactive antibodies to the epitopes identified, e.g. TTEQ and/or related epitopes such as TTE can be employed. To serve as a useful immunogen, the TDP-43 peptide desirably incorporates a minimum of about 3, 4, 5, 6, or 7 TDP-43 residues, comprising minimally T115 and/or T116 and/or E117 and optionally incorporates an immunogenicity enhancing agent such as KLH. As the number of residues in the cyclic peptide increases, the construct becomes more similar conformationally to the linear peptide. The optimal degree of similarity to misfolded states as compared to native structures occurs around 7 to 9 residues (see Table 6C and Table 8A).

The term "corresponding linear compound" with regard to a cyclic compound refers to a compound, optionally a peptide, comprising or consisting of the same sequence or chemical moieties as the cyclic compound but in linear (non-cyclized) form.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.–16.6 (Log 10 [Na+]+0.41(% (G+C)–600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

As used herein "specifically binds" in reference to an antibody means that the antibody recognizes its target antigen and binds its target with greater affinity than it does to a structurally different antigen and/or to an antigen with modified or mutated sequence. For example a multivalent antibody binds its target with $K_D$ of at least 1e-6, at least 1e-7, at least 1e-8, at least 1e-9 or at least 1e-10. Affinities greater than at least 1e-8 are preferred. An antigen binding fragment such as Fab fragment comprising one variable domain, may find its target with a 10 fold or 100 fold less affinity than a multivalent interaction with a non-fragmented antibody.

The term "selective" as used herein with respect to an antibody that preferentially binds a form of TDP-43 (e.g. native, or misfolded protein) means that the binding protein binds the form with at least 3 fold, or at least 5 fold, at least 10 fold, at least 20 fold, at least 100 fold, at least 250 fold, at least 500 fold or at least 1000 fold or more greater affinity. Accordingly an antibody that is more selective for a particular conformation (e.g. misfolded protein, cyclic peptide) preferentially binds the particular form of TDP-43 with at least 3 fold etc greater affinity compared to another form.

The term "linker" as used herein means a chemical moiety that can be covalently linked to the peptide comprising TTEQ (SEQ ID NO:1) epitope peptide, optionally linked to TTEQ (SEQ ID NO:1) peptide N- and C-termini to produce a cyclic compound. The linker can comprise a spacer and/or one or more functionalizable moieties such as a cysteine residue. The linker can be linked via the functionalizable moieties to a carrier protein or an immunogen enhancing component such as keyhole limpet hemocyanin (KLH). The linker can be for example 1 to 9 amino acids.

The term "spacer" as used herein means any non-immunogenic or poorly immunogenic chemical moiety that can be covalently-linked directly or indirectly to a peptide N- and C-termini to produce a cyclic compound of longer length than the peptide itself, for example the spacer can be linked to the N- and C-termini of a peptide consisting of TTEQ (SEQ ID NO:1) to produce a cyclic compound of longer backbone length than the TTEQ (SEQ ID NO:1) sequence itself. That is, when cyclized the peptide with a spacer (for example of 3 amino acid residues) makes a larger closed circle than the peptide without a spacer. The spacer may include, but is not limited to, non-immunogenic moieties such as G, A, or PEG repeats, e.g. when in combination with the peptide being GTTEQG (SEQ ID NO: 4) TTEQG (SEQ ID NO: 5), GTTEQ (SEQ ID NO: 6), etc. The spacer may comprise or be coupled to one or more functionalizing moieties, such as one or more cysteine (C) residues, which can be interspersed within the spacer or covalently linked to one or both ends of the spacer. Where a functionalizable moiety such as a C or D residue is covalently linked to one or more termini of the spacer, the spacer is indirectly covalently linked to the peptide. The spacer can also comprise the functionalizable moiety in a spacer residue as in the case where a biotin molecule is introduced into an amino acid residue.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. Accordingly, the linker can for example be CCC. The reaction with another group of atoms can be covalent or a strong non-covalent bond, for example as in the case of biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be functionalized (e.g. coupled) to the cyclic compound, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing component such as Keyhole limpet hemocyanin (KLH), or a carrier protein such as Bovine serum albumin (BSA) used for in vitro immunoblots or immunohistochemical assays.

The term "reacts with" as used herein generally means that there is a flow of electrons or a transfer of electrostatic charge resulting in the formation of a chemical interaction.

The term "animal" or "subject" as used herein includes all members of the animal kingdom including mammals, optionally including or excluding humans.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a", "an" and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Epitopes and Binding Proteins

The inventors have identified epitopes in TDP-43 including TTEQ (SEQ ID NO: 1) at amino acids 115 to 118 on TDP-43 protein and TTE at amino acids 115 to 117 on TDP-43 protein. They have further identified that these epitopes or parts thereof are conformational epitopes, and that TTE, TEQ or TTEQ (SEQ ID NO: 1) or a part thereof may be selectively accessible to antibody binding in misfolded proteinic species of TDP-43.

Based on one or more conformational differences identified between the epitopes identified in native and biased TDP-43 ensembles, the inventors have designed conformationally restricted compounds and immunogens for producing antibodies that selectively or specifically binds misfolded TDP-43.

Antibodies raised using said immunogens may be useful for detecting misfolded TDP-43.

As described in the Examples, cyclic compounds such as cyclic peptides cyclo (CGGTTEQGG) (SEQ ID NO: 2), cyclo (CGTTEQG) (SEQ ID NO: 3), cyclo (CGTTEG) (SEQ ID NO: 28) and cyclo (CGTTEGG) (SEQ ID NO: 29) may capture the conformational differences of the epitope in misfolded TDP-43 relative to the native species. For example, solvent accessible surface area, RMSD structural alignment, and the dihedral angle distributions for amino acids in the cyclic 9-mer cyclo (CGGTTEQGG) (SEQ ID NO: 2) were found to be significantly different than the corresponding quantities in the native ensemble. This suggests that the cyclic compound may provide for a conformational epitope that is conformationally-distinct from the sequence presented in the native ensemble.

III. TTEQ (SEQ ID NO:1) and TTE "Epitope" Compounds

Accordingly, the present disclosure identifies a conformational epitope in TDP-43 consisting of amino acids TTEQ (SEQ ID NO: 1) or TTE corresponding to amino acids residues 115-117 on TDP-43 and TEQ corresponding to amino acids 116-118. As demonstrated in the Examples, TTEQ (SEQ ID NO: 1) and TTE were identified as regions prone to disorder in TDP-43. The residues TTE and TTEQ (SEQ ID NO:1) emerged in computational predictions.

There are differences in the conformation occupied by the native RRM1 and RRM1 biased to identify regions that may be exposed in misfolded TDP-43. For example, Table 5 shows that E117 is more exposed in the biased protein than in the native protein, and more exposed still in the cyclic peptide cyclo(CGGTTEQGG) (SEQ ID NO: 2). In the native protein this residue participates in a salt bridge with Lys 137 which is disrupted in the biased configuration.

An aspect includes a compound comprising a TDP-43 peptide comprising or consisting of TTEQ (SEQ ID NO: 1), a related epitope and/or part of any of the foregoing such as TTE, wherein if the peptide is TTEQ (SEQ ID NO: 1), the peptide is in a conformation that is distinct in at least one feature from TTE and/or TTEQ (SEQ ID NO: 1) in native TDP-43. In an embodiment, the TDP-43 peptide is selected from TTE, TTEQ (SEQ ID NO: 1), KTTE, (SEQ ID NO: 10), KTTEQ (SEQ ID NO:12), TEQ, TEQD (SEQ ID NO:8) or TTEQD (SEQ ID NO: 9). The TDP-43 peptides TTEQD (SEQ ID NO:9), TEQD (SEQ ID NO:8), KTTEQ (SEQ ID NO:12), TTE, and TEQ can be used to raise antibodies that are included in the epitopes collectively referred to herein as TTEQ (SEQ ID NO: 1) and related epitopes. In an embodiment, the related epitope comprises or consists of TTE, TEQD (SEQ ID NO: 8), KTTE (SEQ ID NO: 10) and epitopes that comprise 1, 2 or 3 amino acids in TDP-43 either N-terminal or C-terminal to TTE.

In some embodiments, the peptide, a conformational peptide, comprising TTE, TEQ or TTEQ (SEQ ID NO: 1) can include 1, or 2 additional residues in TDP-43 N- and/or C-terminus of TTEQ (SEQ ID NO: 1) for example TTEQD (SEQ ID NO:9) or KTTEQD (SEQ ID NO:7). For example, the 3 amino acids N-terminal to TTEQ (SEQ ID NO:1) in TDP-43 are PWK and the 3 amino acids C-terminal to TTEQ (SEQ ID NO:1) are DLK. In an embodiment, the TDP-43 peptide is a maximum of 6 TDP-43 residues. In an embodiment, the TDP-43 peptide is a maximum of 5 TDP-43 residues. In yet another embodiment, the TDP-43 peptide (e.g. in the compound such as a cyclic compound) is 4 TDP-43 residues, optionally TTEQ (SEQ ID NO: 1).

In an embodiment, the compound further includes a linker. The linker comprises a spacer and/or one or more functionalizable moieties. The linker can for example comprise 1, 2, 3, 4, 5, 6, 7, 8 or 9 amino acids and/or equivalently functioning molecules such as polyethylene glycol (PEG) moieties, and/or a combination thereof. In an embodiment, the spacer amino acids are selected from non-immunogenic or poorly immunogenic amino acid residues such as G and A, for example the spacer can be GGG, GAG, G(PEG)G, PEG-PEG (also referred to as PEG2)-GG and the like. One or more functionalizable moieties e.g. amino acids with a functional group may be included for example for coupling the compound to an agent or detectable tag or a carrier such as BSA or an immunogenicity enhancing component such as KLH.

In an embodiment the linker comprises GC-PEG, PEG-GC, GCG or PEG2-CG.

In an embodiment, the linker comprises 1, 2, 3, 4, 5, 6, 7, 8 or 9 amino acids.

In embodiments wherein the peptide comprising TTE or TTEQ (SEQ ID NO: 1) includes 1, 2 or 3 additional residues found in TDP-43 that are N- and/or C-terminal to TTEQ (SEQ ID NO: 1) the linker in the cyclized compound is covalently linked to the N- and/or C-termini of the TDP-43 residues (e.g. where the peptide is KTTEQ (SEQ ID NO:12), the linker is covalently linked to K and Q residues). Similarly, where the TDP-43 peptide is TTEQ (SEQ ID NO: 1), the linker is covalently linked to residues T and Q and where the TDP-43 peptide is TTEQD (SEQ ID NO: 9), the linker is covalently linked to residues T and D.

Proteinaceous portions of compounds (or the compound wherein the linker is also proteinaceous) may be prepared by chemical synthesis using techniques well known in the chemistry of proteins such as solid phase synthesis or synthesis in homogenous solution.

In an embodiment, the compound is a cyclic compound e.g the TDP-43 peptide comprising TTE or TTEQ (SEQ ID NO: 1) is comprised in a cyclic compound. Reference to the "cyclic peptide" herein can refer to a fully proteinaceous compound (e.g. wherein the linker is 2, 3, 4, 5, 6, 7, 8 or 9 amino acids). It is understood that properties described for the cyclic peptide determined in the examples can be incorporated in other compounds (e.g. cyclic compounds) comprising non-amino acid linker molecules.

An aspect therefore provides a cyclic compound comprising peptide TTEQ (SEQ ID NO:1) (or a part thereof such as TTE) and a linker, wherein the linker is covalently coupled directly or indirectly to the peptide comprising TTE or TTEQ (SEQ ID NO:1), optionally wherein at least the one of the T115, the T116, the E117, and/or Q118 residues is in an alternate conformation than the T, T, E, and Q residues in a native ensemble comprising TTEQ (SEQ ID NO:1), as may be manifest in native TDP-43, and optionally wherein at least T, T, E, and/or Q, is in either a more solvent exposed conformation, or an alternative conformation, than the conformation occupied in a native ensemble comprising TTEQ (SEQ ID NO:1), as may be manifest for example in TDP-43 dimer.

In an embodiment, the cyclic compound comprises a TDP-43 peptide comprising TTE or TTEQ (SEQ ID NO:1) and up to 6 TDP-43 residues (e.g. 1 or 2 (or 3 in the case of TTE) amino acids N and/or C terminus to TTE or TTEQ (SEQ ID NO:1)) and a linker, wherein the linker is covalently coupled directly or indirectly to the peptide N-terminus residue and the C-terminus residue of the TDP-43 peptide and optionally wherein at least T115, T116, E or Q is in an alternate conformation than T115, T116, E, or Q in the native ensemble comprising TTEQ (SEQ ID NO: 1), and/or the conformation of T115, T116, E, or Q in TTEQ (SEQ ID NO: 1) in the native and optionally wherein at least T115, T116, E, or Q, has more surface exposure than the conformation occupied in the native ensemble comprising TTEQ (SEQ ID NO: 1).

The cyclic compound can be synthesized as a linear molecule with the linker covalently attached to the N-terminus or C-terminus of the peptide comprising the TDP-43 peptide, optionally TTEQ (SEQ ID NO: 1) or related epitope, prior to cyclization. Alternatively part of the linker is covalently attached to the N-terminus and part is covalently attached to the C-terminus prior to cyclization. In either case, the linear compound is cyclized for example in a head to tail cyclization (e.g. amide bond cyclization).

In an embodiment the cyclic compound comprises a peptide comprising or consisting of TTEQ (SEQ ID NO: 1) and a linker, wherein the linker is coupled to the N- and C-termini of the peptide (e.g. the T and the Q residues when the peptide consists of TTEQ (SEQ ID NO: 1). In an embodiment, at least one of the T, E and/or Q residues is in an alternate conformation in the cyclic compound than occupied by at least one of the T, E and/or Q residues in a native ensemble comprising TTEQ (SEQ ID NO: 1).

In an embodiment, at least one of the T, E, and/or Q residues is in an alternate conformation in the cyclic compound than occupied by a residue, optionally by T, E, and/or Q, in the native ensemble.

In an embodiment, at least one of the T, E, and/or Q residues is in an alternate conformation in the cyclic compound than occupied by a residue in the native.

In an embodiment, the alternate conformation is a more solvent-exposed conformation.

In an embodiment, at least T115, optionally alone or in combination with T116, is in an alternate conformation than the conformation occupied in a native ensemble comprising TTEQ (SEQ ID NO: 1).

For example, the alternate conformation can include one or more differing dihedral angles in residue T115, differing from the dihedral angles in the native ensemble.

For example, the alternate conformation can include one or more differing backbone dihedral angles (Ramachandran angles) in residue T115, differing from the dihedral angles in the native ensemble.

In an embodiment, the cyclic compound comprises a minimum average side-chain/backbone dihedral angle difference between the cyclic compound and native ensemble.

In an embodiment, the cyclic compound comprises a residue selected from T, E, and Q, wherein one or more side-chain or backbone dihedral angles are at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees, at least 140 degrees, at least 150 degrees, at least 160 degrees or at least 170 degrees, different in the cyclic compound, than the corresponding dihedral angle in the context of the native ensemble.

As shown in FIGS. 2 and 3, several backbone and sidechain dihedral angle distributions of T115 and T116 are substantially different in the cyclic peptide ensemble compared to the native ensemble. For example, Table 2A indicates that for simulated native ensembles and cyclic peptides, the difference in the dihedral angle C—CA-CB-OG1 of T115 is most likely about −160 degrees between cyclic and native. In an embodiment, the cyclic compound comprises a T residue comprising an C—CA-CB-OG1 dihedral angle that is at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees, at least 140 degrees, at least 150 degrees or at least 160 degrees than the corresponding dihedral angle in the context of the native ensemble. Similarly, the differences in dihedral angles between cyclic and native ensembles for T116 dihedral N—CA-CB-OG1 is most likely about 150 degrees. Accordingly in an embodiment, the cyclic compound comprises a T comprising a dihedral angle N—CA-CB-OG1 that is at least 30 degrees different, at least 40 degrees different, at least 50 degrees different, at least 60 degrees different, at least 70 degrees different, at least 80 degrees different, at least 90 degrees different, at least 100 degrees different, and so on up to at least 150 degrees different, than the corresponding dihedral angle in the context of the linear compound. The corresponding differences in most-likely dihedral angles between cyclic peptide and native ensembles for T115 dihedral C—CA—N—HN is 50 degrees. Accordingly in an embodiment, the cyclic compound comprises a T comprising dihedral angle for C—CA-N—HN that is at least 30 degrees different, at least 40 degrees different or at least 50 degrees different, than the corresponding dihedral angle in the context of the native ensemble. The corresponding differences in most-likely dihedral angles between cyclic peptide and native ensembles for T116 dihedral CB-CA-N—HN is −70 degrees. Accordingly in an embodiment, the cyclic compound comprises a T comprising dihedral angle for CB-CA-N—HN that is at least 30 degrees different, at least 40 degrees different, at least 50 degrees different, at least 60 degrees different or at least 70 degrees different than the corresponding dihedral angle in the context of either the native ensemble or the native. The above angle differences can for example be positive or negative, (+) or (−).

According to the peak values of Ramachandran angles given in Table 4A, the most-likely Ramachandran φ and ψ values are different between the cyclic and native ensembles for residues T115, T116, E117, and Q118, as also presented in Table 4B. The respective differences Δφ between the cyclic and native peak φ values are 50, −65, −40, and −35 degrees, and the respective differences ΔΨ between the Ψ values of the cyclic and native peaks are −45, 30, 40, and 50 degrees. Overall the φ,Ψ values are significantly different between cyclic and native peptides. Table 3A gives the overlap of the distributions of φ,Ψ values in the cyclic and native ensembles. The average overlap of φ and Ψ distributions for T115, T116, E117, and Q118 is 28%, 63%, 55% and 23% respectively. Together these numbers indicate different distributions of dihedral angles for the cyclic and native ensembles.

In an embodiment, the cyclic compound comprises a Q comprising an Ramachandran backbone angle that is at least 30 degrees, at least 40 degrees different, at least 50 degrees or at least 60 degrees different than the corresponding Ramachandran angle in the context of the native compound.

The angle difference can for example be positive or negative, (+) or (−).

The alternate conformation can comprise an alternate backbone orientation. For example, the backbone orientation that the cyclic epitope exposes for an antibody differs compared to the native form.

In an embodiment, T, T, E, Q, TT, TE, EQ, TTE, TEQ, and/or TTEQ (SEQ ID NO: 1) are in an alternate conformation, for example as compared to what is occupied by these residues in a non-misfolded proteinic conformation, such as the native ensemble.

The cyclic compound in some embodiments that comprises a peptide comprising TTEQ (SEQ ID NO: 1), TTE or KTTE (SEQ ID NO:10) can include 1, or 2 or more residues in TDP-43 upstream and/or downstream of one of the foregoing, for example of TTEQ (SEQ ID NO: 1). In such cases the spacer is covalently linked to the N- and C-termini of the ends of the corresponding residues of the TDP-43 sequence.

In an embodiment, the cyclic compound has a sequence selected from any one of SEQ ID NOs: 2, 3, 22, 23, 28, 29, 30, 31, 32, 33, 34, 35 and 42 or any subset thereof. In an embodiment, the cyclic compound comprises a sequence selected from any one of SEQ ID NOs: 28, 29, 30, 31, 32, 33, 34 and 35. In another embodiment, the cyclic compound comprises a sequence selected from SEQ ID NO: 2, 3, 22, 23 and 42. In yet other embodiments, the cyclic compound comprises a sequence selected from any one of SEQ ID NOs: 29, 32 and 34. In yet other embodiments, the cyclic compound comprises a sequence selected from any one of SEQ ID NOs: 2, 3, 22 and 23.

Methods for making cyclized peptides are known in the art and include SS-cyclization or amide cyclization (head-to-tail, or backbone cyclization). Methods are further described in in the Example section. For example, a peptide with "C" residues at its N- and C-termini, e.g. CGTTEQGC (SEQ ID NO: 13), can be reacted by SS-cyclization to produce a cyclic peptide. As described in the Examples, cyclic compounds were assessed for their relatedness to the conformational epitopes identified. A cyclic compound comprising TTEQ (SEQ ID NO: 1) or TTE TDP-43 peptide for example may be used to raise antibodies selective for misfolded TDP-43.

The epitope TTEQ (SEQ ID NO: 1) and/or a part thereof, as described herein may be a potential target in misfolded propagating strains of TDP-43, and antibodies that recognize the conformational epitope may for example be useful in detecting such propagating strains.

Another aspect includes an immunogen comprising a compound comprising a TTE, TTEQ (SEQ ID NO: 1) or related epitope, optionally a cyclic compound described herein. In an embodiment, the immunogen comprises an immunogenicity enhancing component such as Keyhole Limpet Hemocyanin (KLH) and/or is formulated for co-injection with an adjuvant (e.g. alum, monophosphoryl lipid A or QS21). Other similar components are known in the art and additional adjuvants are described below. The adjuvant is typically formulated in a composition with the compound as is further described below. The immunogenicity enhancing component can be coupled to the compound either directly, such as through an amide bond, disulfide bond, or indirectly through a chemical linker. In another embodiment, the immunogen is a multi-antigenic peptide (MAP). For example, the MAP can be synthesized by preparing a linear compound to be cyclized, cyclizing the peptide, optionally using head to tail cyclization and conjugating the cyclized peptide to a MAP resin through an amino acid in the linker, optionally through a C or D residue in the linker. MAPs have been constructed for cyclic structures (see for example Misumi et al J. Virol. December 2001 vol. 75 no. 23 11614-11620) and similar methods to those described therein can be used.

The immunogen with an immunogenicity enhancing component can be produced by conjugating the cyclic compound containing the constrained epitope peptide and a linker comprising a functionalizable moiety such as cysteine to an immunogenicity enhancing component such as Keyhole Limpet Hemocyanin (KLH) or a carrier such bovine serum albumin (BSA) using for example the method described in Lateef et al 2007, herein incorporated by reference. In an embodiment, the method described in Example 3 is used.

A further aspect is an isolated nucleic acid encoding the proteinaceous portion of a compound or immunogen described herein.

IV. Antibodies, Cells and Nucleic Acids

Accordingly, the compounds and particularly the cyclic compounds comprising epitope TTEQ (SEQ ID NO: 1) or a related epitope described above can be used to raise antibodies. Cyclic compounds comprising TTEQ (SEQ ID NO: 1) or a related epitope for example KTTE (SEQ ID NO:10), TTE, TEQ, TTEQD (SEQ ID NO:9), KTTEQD (SEQ ID NO: 7), KTTEQDL (SED ID NO:14) and/or other related epitope sequences described herein can be used to raise antibodies that selectively bind misfolded TDP-43.

Accordingly, the compounds and particularly the cyclic compounds described herein including for example those comprising epitope or cyclic compound sequences listed in Table 11 can be used to raise antibodies that specifically or selectively bind the epitope in TDP-43 that they comprise and/or which recognize specific conformations of these residues in misfolded TDP-43, including one or more differential features described herein.

Accordingly, an aspect includes an antibody that specifically or selectively bind an epitope on TDP-43, the epitope comprising or consisting TTEQ (SEQ ID NO: 1), a related epitope thereof or a part thereof or a conformational epitope of any of the foregoing. In an embodiment, wherein when the epitope consists of TTEQ (SEQ ID NO: 1) it is a conformational epitope.

In an embodiment the antibody is isolated.

In an embodiment, the antibody does not specifically bind and/or is not selective for native TDP-43 e.g. wherein the conformation of TTEQ (SEQ ID NO:1) or a related epitope such as TTE is as present in native TDP-43. Selective binding can be measured using an ELISA or surface plasmon resonance measurement, as described herein.

Accordingly a further aspect is an antibody which specifically or selectively binds an epitope present on TDP-43, wherein the epitope comprises or consists of at least one amino acid residue predominantly involved in binding to the antibody, wherein at least one amino acid is T115, T116, E, or Q embedded within the sequence TTEQ (SEQ ID NO:1), TEQ, or KTTE (SEQ ID NO:10), optionally wherein the epitope when consisting of TTEQ (SEQ ID NO:1) is a conformational epitope (e.g. selectively binds a peptide in an alternate optionally solvent-exposed conformation relative to the corresponding native ensemble, for example where at least one amino acid of the epitope is more solvent-exposed). In an embodiment, the epitope comprises or consists of at least two consecutive amino acid residues predominantly involved in binding to the antibody, wherein the at least two consecutive amino acids are TE, or EQ embedded within TTEQ (SEQ ID NO:1), TTE or TEQ In another embodiment, the epitope is a conformational epitope and consists of TTEQ (SEQ ID NO:1), TTE or TEQ. In an embodiment, the antibody selectively binds TTEQ (SEQ ID NO:1), TTE or TEQ or other related epitope in a cyclic compound, optionally cyclic peptide, optionally cyclo (CGTTEQG) (SEQ ID NO: 3) or a cyclic peptide having a sequence of any one SEQ ID NOs: 2, 3, 22, 23, 28, 29, 30, 31, 32, 33, 34, 35 and 42, or any subset thereof, relative to a corresponding linear peptide and/or a native ensemble.

In an embodiment, the antibody specifically binds a cyclic compound comprising an epitope peptide described herein comprising at least one alternate conformational feature described herein (e.g. of the epitope in a cyclic compound compared to a native structural ensemble). For example an antibody that binds a particular epitope conformation can be referred to as a conformation specific antibody. The conformation specific antibody can differentially recognize a particular misfolded TDP-43 species, and can have a higher affinity for one species or group of species compared to the native species.

For example, in an embodiment, the antibody specifically binds a cyclic compound comprises a residue selected from T, E, and Q, wherein at least one dihedral angle is at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees, at least 140 degrees or at least 150 degrees different in the cyclic compound, than the corresponding dihedral angle in the context of the native structure.

In an embodiment, the antibody selectively binds a cyclic compound comprising TTEQ (SEQ ID NO:1) or a part thereof, optionally in the context of cyclo (CGGTTEQGG) (SEQ ID NO:2) relative to a native ensemble comprising TTEQ (SEQ ID NO:1), optionally in the context of linear cyclo (CGTTEQG) (SEQ ID NO: 3) relative to a native ensemble comprising TTEQ (SEQ ID NO:1). For example, in an embodiment the antibody selectively binds TTEQ (SEQ ID NO:1) or TTE in a cyclic conformation and has at least 2 fold, at least 3 fold, at least 5 fold, at least 8 fold, at least 10, fold, at least 15 fold, at least 20 fold, at least 30 fold, at least 40 fold, at least 50 fold, at least 100 fold, at least 500 fold or at least 1000 fold more selective greater selectivity (e.g. binding affinity) for TTEQ (SEQ ID NO:1) or TTE in the cyclic conformation compared to TTEQ (SEQ ID NO:1) or TTE in a native ensemble, for example as measured by ELISA, immunohistochemistry or surface plasmon resonance, optionally using a method described herein.

In an embodiment, the cyclic compound selectively bound and/or used to produce antibodies is a compound of Table 11. In another embodiment, said cyclic compound is a cyclic compound selected from SEQ ID NOs: 2, 3, 22, 23, 28, 29, 30, 31, 32, 33, 34, 35 and 42, or any subset thereof. In an embodiment, the cyclic compound comprises a sequence selected from any one of SEQ ID NOs: 28, 29, 30, 31, 32, 33, 34 and 35. In another embodiment, the cyclic compound comprises a sequence selected from SEQ ID NO: 2, 3, 22, 23 and 42. In yet other embodiments, the cyclic compound comprises a sequence selected from any one of SEQ ID NOs: 29, 32 and 34. In yet other embodiments, the cyclic compound comprises a sequence selected from any one of SEQ ID NOs: 2, 3, 22 and 23.

In an embodiment, the cyclic compound selectively bound is a compound of Table 11. In an embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold or at least 1000 fold more selective for the cyclic compound and/or Misfolded TDP-43 polypeptide over a species of TDP-43 selected from native TDP-43.

In yet another aspect, the disclosure provides an antibody that competes for selectively binds to a cyclic peptide having a sequence selected from any one of SEQ ID NOs: 2, 3, 22, 23, 28, 29, 30, 31, 32, 33, 34, 35 and 42.

To produce monoclonal antibodies, antibody producing cells (lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol.Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the desired epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990)).

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (e.g. Scotgen Limited, 2 Holly Road, Twickenham, Middlesex, Great Britain.).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced where members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class. Further, these antibodies are typically produced as antigen binding fragments such as Fab, Fab' F(ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Additionally, antibodies specific for the epitopes described herein are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, Calif.) Methods for screening antibody phage libraries are well known in the art.

As indicated below, several antibodies that were positive for detecting misfolded, disease-associated TDP-43 in transfected cells or ALS spinal cord homogenates were sequenced.

Accordingly, in another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GYTFTDYS; SEQ ID NO: 67

CDR-H2:
INTETGEP; SEQ ID NO: 68

CDR-H3:
ASRRWYPYYFDY; SEQ ID NO: 69

CDR-L1:
TGAVTTSNY; SEQ ID NO: 70

CDR-L2:
GPN; SEQ ID NO: 71
and

CDR-L3:
ALWYSNHWV. SEQ ID NO: 72

In another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GFTFSDYY; SEQ ID NO: 73

CDR-H2:
ISNGGGST; SEQ ID NO: 74

CDR-H3:
AREGGTAWFAY; SEQ ID NO: 75

CDR-L1:
QSIVHSNGNTY; SEQ ID NO: 76

CDR-L2:
KVS; SEQ ID NO: 77
and

CDR-L3:
FQGSHVPYT. SEQ ID NO: 78

In another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GFTFSDYY; SEQ ID NO: 73

CDR-H2:
ISDGGSYT; SEQ ID NO: 79

CDR-H3:
ARDYYGSSSYTSGFAY; SEQ ID NO: 80

CDR-L1:
QSIVHSNGNTY; SEQ ID NO: 76

CDR-L2:
KVS; SEQ ID NO: 77
and

CDR-L3:
FQGSHVPGT. SEQ ID NO: 81

In another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GYTFTDYS; SEQ ID NO: 67

CDR-H2:
INTETGEP; SEQ ID NO: 68

CDR-H3:
ARGYGNWFAY; SEQ ID NO: 82

CDR-L1:
SSVSSSY; SEQ ID NO: 83

CDR-L2:
STS; SEQ ID NO: 84
and

CDR-L3:
HQYHRSPLT. SEQ ID NO: 85

In yet another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GFTFSDFY; SEQ ID NO: 86

CDR-H2:
SRSKAHDYTT; SEQ ID NO: 87
and

CDR-H3:
ARDTWYGSWFAY; SEQ ID NO: 88

CDR-L1:
QSIVHSNGNTY; SEQ ID NO: 76

CDR-L2:
KVS; SEQ ID NO: 77
and

CDR-L3:
FQGSHVPPT. SEQ ID NO: 92.

In yet another embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

CDR-H1:
GYAFTNYL; SEQ ID NO: 89

CDR-H2:
INPGSGGT; SEQ ID NO: 90
and

CDR-H3:
ARWGGNYSGYAMDY; SEQ ID NO: 91

CDR-L1:
QSIVHSNGNTY; SEQ ID NO: 76

CDR-L2:
KVS; SEQ ID NO: 77
and

CDR-L3:
FQGSHVPPT. SEQ ID NO: 92

As shown in FIGS. 13A and B, the CDRS share structural similarity. In particular, the light chain sequences of several clones are similar.

In an embodiment, the antibody is a monoclonal antibody. In an embodiment, the antibody is a chimeric antibody such as a humanized antibody comprising the CDR sequences as recited in Table 10.

Also provided in another embodiment, is an antibody comprising the CDRs in Table 10 and a light chain variable region and a heavy chain variable region, optionally in the context of a single chain antibody.

In yet another aspect, the antibody comprises a heavy chain variable region comprises: i) an amino acid sequence as set forth in SEQ ID NO: 46; ii) an amino acid sequence with at least 50%, at least 60%, at least 70%, at least 80% or at least 90% sequence identity to SEQ ID NO: 46, wherein the CDR sequences are as set forth in SEQ ID NO: 67, 68 and 69, or iii) a conservatively substituted amino acid sequence i). In another aspect the antibody comprises a light chain variable region comprising i) an amino acid sequence as set forth in SEQ ID NO: 48, ii) an amino acid sequence with at least 50%, at least 60%, at least 70%, at least 80% or at least 90% sequence identity to SEQ ID NO: 48 wherein the CDR sequences are as set forth in SEQ ID NO: 70, 71 and 72, or iii) a conservatively substituted amino acid sequence of i). In another embodiment, the heavy chain variable region amino acid sequence is encoded by a nucleotide sequence as set out in SEQ ID NO: 45 or a codon degenerate or optimized version thereof. In another embodiment, the antibody comprises a light chain variable region amino acid sequence encoded by a nucleotide sequence as set out in SEQ ID NO: 47 or a codon degenerate or optimized version thereof. In an embodiment, the heavy chain variable region comprises an amino acid sequence as set forth in SEQ ID NO: 46. In an embodiment, the light chain variable region comprises an amino acid sequence as set forth in SEQ ID NO: 48.

In yet another aspect, the antibody comprises a heavy chain variable region comprises: i) an amino acid sequence as set forth in SEQ ID NO: 50; ii) an amino acid sequence with at least 50%, at least 60%, at least 70%, at least 80% or at least 90% sequence identity to SEQ ID NO: 50, wherein the CDR sequences are as set forth in SEQ ID NO: 73, 74 and 75, or iii) a conservatively substituted amino acid sequence i). In another aspect the antibody comprises a light chain variable region comprising i) an amino acid sequence as set forth in SEQ ID NO: 52, ii) an amino acid sequence with at least 50%, at least 60%, at least 70%, at least 80% or at least 90% sequence identity to SEQ ID NO: 52 wherein the CDR sequences are as set forth in SEQ ID NO: 76, 77 and 78, or iii) a conservatively substituted amino acid sequence of i). In another embodiment, the heavy chain variable region amino acid sequence is encoded by a nucleotide sequence as set out in SEQ ID NO: 49 or a codon degenerate or optimized version thereof. In another embodiment, the antibody comprises a light chain variable region amino acid sequence encoded by a nucleotide sequence as set out in SEQ ID NO: 51 or a codon degenerate or optimized version thereof. In an embodiment, the heavy chain variable region comprises an amino acid sequence as set forth in SEQ ID NO: 50. In an embodiment, the light chain variable region comprises an amino acid sequence as set forth in SEQ ID NO: 52.

In yet another aspect, the antibody comprises a heavy chain variable region comprises: i) an amino acid sequence as set forth in SEQ ID NO: 54; ii) an amino acid sequence with at least 50%, at least 60%, at least 70%, at least 80% or at least 90% sequence identity to SEQ ID NO: 54, wherein the CDR sequences are as set forth in SEQ ID NO: 73, 79 and 80, or iii) a conservatively substituted amino acid sequence i). In another aspect the antibody comprises a light chain variable region comprising i) an amino acid sequence as set forth in SEQ ID NO: 56, ii) an amino acid sequence with at least 50%, at least 60%, at least 70%, at least 80% or at least 90% sequence identity to SEQ ID NO: 56 wherein the CDR sequences are as set forth in SEQ ID NO: 76, 77 and 81, or iii) a conservatively substituted amino acid sequence of i). In another embodiment, the heavy chain variable region amino acid sequence is encoded by a nucleotide sequence as set out in SEQ ID NO: 53 or a codon degenerate or optimized version thereof. In another embodiment, the antibody comprises a light chain variable region amino acid sequence encoded by a nucleotide sequence as set out in SEQ ID NO: 55 or a codon degenerate or optimized version thereof. In an embodiment, the heavy chain variable region comprises an amino acid sequence as set forth in SEQ ID NO: 54. In an embodiment, the light chain variable region comprises an amino acid sequence as set forth in SEQ ID NO: 56.

In yet another aspect, the antibody comprises a heavy chain variable region comprises: i) an amino acid sequence as set forth in SEQ ID NO: 58; ii) an amino acid sequence with at least 50%, at least 60%, at least 70%, at least 80% or at least 90% sequence identity to SEQ ID NO: 58, wherein the CDR sequences are as set forth in SEQ ID NO: 67, 68 and 82, or iii) a conservatively substituted amino acid sequence i). In another aspect the antibody comprises a light chain variable region comprising i) an amino acid sequence as set forth in SEQ ID NO: 60, ii) an amino acid sequence with at least 50%, at least 60%, at least 70%, at least 80% or at least 90% sequence identity to SEQ ID NO: 60 wherein the CDR sequences are as set forth in SEQ ID NO: 83, 84 and 85, or iii) a conservatively substituted amino acid sequence of i). In another embodiment, the heavy chain variable region amino acid sequence is encoded by a nucleotide sequence as set out in SEQ ID NO: 57 or a codon degenerate or optimized version thereof. In another embodiment, the antibody comprises a light chain variable region amino acid sequence encoded by a nucleotide sequence as set out in SEQ ID NO: 59 or a codon degenerate or optimized version thereof. In an embodiment, the heavy chain variable region comprises an amino acid sequence as set forth in SEQ ID NO: 58. In an embodiment, the light chain variable region comprises an amino acid sequence as set forth in SEQ ID NO: 60.

In yet another aspect, the antibody comprises a heavy chain variable region comprises: i) an amino acid sequence as set forth in SEQ ID NO: 62; ii) an amino acid sequence with at least 50%, at least 60%, at least 70%, at least 80% or at least 90% sequence identity to SEQ ID NO: 62, wherein the CDR sequences are as set forth in SEQ ID NO: 86, 87 and 88, or iii) a conservatively substituted amino acid sequence i). In another aspect the antibody comprises a light chain variable region comprising i) an amino acid sequence as set forth in SEQ ID NO: 64, ii) an amino acid sequence with at least 50%, at least 60%, at least 70%, at least 80% or at least 90% sequence identity to SEQ ID NO: 64 wherein the CDR sequences are as set forth in SEQ ID NO: 76, 77 and 92, or iii) a conservatively substituted amino acid sequence of i). In another embodiment, the heavy chain variable region amino acid sequence is encoded by a nucleotide sequence as set out in SEQ ID NO: 61 or a codon degenerate or optimized version thereof. In another embodiment, the antibody comprises a light chain variable region amino acid sequence encoded by a nucleotide sequence as set out in SEQ ID NO: 63 or a codon degenerate or optimized version thereof. In an embodiment, the heavy chain variable region comprises an amino acid sequence as set forth in SEQ ID NO: 62. In an embodiment, the light chain variable region comprises an amino acid sequence as set forth in SEQ ID NO: 64.

In yet another aspect, the antibody comprises a heavy chain variable region comprises: i) an amino acid sequence as set forth in SEQ ID NO: 66; ii) an amino acid sequence with at least 50%, at least 60%, at least 70%, at least 80% or at least 90% sequence identity to SEQ ID NO: 66, wherein the CDR sequences are as set forth in SEQ ID NO: 89, 90 and 91, or iii) a conservatively substituted amino acid sequence i). In another aspect the antibody comprises a light chain variable region comprising i) an amino acid sequence as set forth in SEQ ID NO: 64, ii) an amino acid sequence with at least 50%, at least 60%, at least 70%, at least 80% or at least 90% sequence identity to SEQ ID NO: 64 wherein the CDR sequences are as set forth in SEQ ID NO: 76, 77 and 92, or iii) a conservatively substituted amino acid sequence of i). In another embodiment, the heavy chain variable region amino acid sequence is encoded by a nucleotide sequence as set out in SEQ ID NO: 65 or a codon degenerate or optimized version thereof. In another embodiment, the antibody comprises a light chain variable region amino acid sequence encoded by a nucleotide sequence as set out in SEQ ID NO: 63 or a codon degenerate or optimized version thereof. In an embodiment, the heavy chain variable region comprises an amino acid sequence as set forth in SEQ ID NO: 66. In an embodiment, the light chain variable region comprises an amino acid sequence as set forth in SEQ ID NO: 64.

Another aspect is an antibody that specifically binds a same epitope as the antibody with CDR sequences as recited in Table 10.

Another aspect includes an antibody that competes for binding to a cyclic compound described herein and/or to human misfolded TDP43 with an antibody described herein such as an antibody comprising the CDR sequences as recited in Table 10.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

A further aspect is an antibody conjugated to a detectable label. In an embodiment, the detectable label is a positron-emitting radionuclide. A positron-emitting radionuclide can be used for example in PET imaging. In an embodiment, the antibody is conjugated to a transport moiety that permits transport across the blood brain barrier and/or into a cell. For example the antibody can be covalently linked to the iron-transport protein melanotransferrin (p97) or fused to antibody fragments specific for BBB receptors such as the transferrin receptor, insulin receptor, lipoprotein receptor, basigin, Glut1 or CD98hc. Another example is fusion to the BBB-permeable single domain antibody FC5 or single domain antibodies directed against other BBB surface receptors. In an embodiment, the antibody is conjugated to a transport moiety that facilitates entry into a cell for diagnostic detection of intracellular aggregated TDP43. For example, the antibody can be chemically linked or recobinantly fused to cell-penetrating peptides such as trans-activating transcriptional activator (TAT) and TAT derivatives, penetratin or transportan, and the like.

A further aspect relates to an antibody complex comprising an antibody described herein and/or a binding fragment thereof and misfolded TDP-43. A further aspect is an isolated nucleic acid encoding an antibody or part thereof described herein.

Nucleic acids encoding a heavy chain or a light chain are also provided, for example encoding a heavy chain comprising CDR-H1, CDR-H2 and/or CDR-H3 regions described herein or encoding a light chain comprising CDR-L1, CDR-L2 and/or CDR-L3 regions described herein.

The present disclosure also provides variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences In another embodiment, the variant nucleic acid sequences have at least 50%, at least 60%, at least 70%, most preferably at least 80%, even more preferably at least 90% and even most preferably at least 95% sequence identity to nucleic acid sequences encoding any one of SEQ ID NOs: 45, 47, 49, 51, 53, 55, 57, 59, 61, 63 and 65.

Another aspect is an expression cassette or vector comprising the nucleic acid herein disclosed. In an embodiment, the vector is an isolated vector.

The vector can be any vector, including vectors suitable for producing an antibody and/or binding fragment thereof or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Systems for the transfer of genes for example into neurons and neural tissue both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome-DNA complexes. Another approach is the use of AAV plasmids in which the DNA is polycation-condensed and lipid entrapped and introduced into the brain by intracerebral gene delivery (Leone et al. US Application No. 2002076394).

Accordingly, in another aspect, the compounds, immunogens, nucleic acids, vectors and antibodies described herein may be formulated in vesicles such as liposomes, nanoparticles, and viral protein particles, for example for delivery of antibodies, compounds, immunogens and nucleic acids described herein. In particular synthetic polymer vesicles, including polymersomes, can be used to administer antibodies.

Also provided in another aspect is a cell expressing an antibody or part thereof described herein. In an embodiment, the cell is an isolated and/or recombinant cell, expressing an antibody described herein or comprising a vector herein disclosed. In an embodiment, the cell is a fused cell such as a hybridoma.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In another embodiment, the mammalian cell is a myeloma cell, a spleen cell, or a hybridoma cell.

In an embodiment, the cell is a neural cell.

Yeast and fungi host cells suitable for expressing an antibody or peptide include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, Calif.). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

In an embodiment, the cell is a fused cell such as a hybridoma cell, the hybridoma cell producing an antibody specific and/or selective for an epitope or epitope sequence described herein, including for example that selectively binds TDP-43 pathological oligomers over TDP43 native structures, selectively binds an epitope sequence presented in a cyclic compound relative to a linear compound or lacks or has negligible plaque binding.

A further aspect is a hybridoma cell line producing an antibody specific for an epitope described herein.

V. Compositions

A further aspect is a composition comprising a compound, immunogen, nucleic acid, vector or antibody described herein.

In an embodiment, the composition comprises a diluent. Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment comprising a compound or immunogen described herein, the composition comprises an adjuvant.

In an embodiment, the adjuvant is selected from. alum, monophosphoryl lipid A and QS21.

Adjuvants that can be used for example, include Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide (TM)), or other bacterial cell wall components.

The adjuvant may be administered with an immunogen as a single composition. Alternatively, an adjuvant may be administered before, concurrent and/or after administration of the immunogen.

In an embodiment, the composition comprises an antibody or part thereof described herein. In another embodiment, the composition comprises an antibody or part thereof described herein and a diluent. In an embodiment, the composition is a sterile composition.

In an embodiment, the composition is for a method described herein such as detecting misfolded TDP-43.

VI. Kits

A further aspect relates to a kit comprising i) an antibody and/or binding fragment thereof, ii) a nucleic acid, iii) peptide or immunogen, iv) composition or v) recombinant cell described herein, comprised in a vial such as a sterile vial or other housing and optionally a reference agent and/or instructions for use thereof.

In an embodiment, the kit is an ELISA.

In an embodiment, the kit comprises an antibody or binding fragment described herein contained in a container such as a sterile vial.

VII. Methods

Included are methods for making the compounds, immunogens and antibodies described herein.

In particular, provided are methods of making an antibody selective for a conformational epitope of TTEQ (SEQ ID NO:1) or related epitope. In an embodiment, the method comprises administering an immunogen described herein to a subject and isolating antibodies that selectively bind the TDP-43 peptide of the immunogen and/or misfolded TDP-43.

A further aspect provides a method of detecting whether a sample comprises misfolded TDP-43, for example misfolded TDP-43 comprising TTE, TTEQ (SEQ ID NO:1) or related conformational epitope and/or wherein at least one of the residues T115, T116, E, or Q is in an alternate conformation than occupied by T, E, and/or Q in a non-misfolded proteinic conformation.

In an embodiment, the method comprises:
a. contacting the sample with the antibody described herein under conditions permissive to produce an antibody: misfolded TDP-43 polypeptide complex; and
b. detecting the presence of any complex;
wherein the presence of detectable complex is indicative that the sample may contain misfolded TDP-43 polypeptide.

In another embodiment, the method comprises:
(a) contacting a test sample of said subject with an antibody described herein, under conditions permissive to produce an antibody-antigen complex;
(b) measuring the amount of the antibody-antigen complex in the test sample; and
(c) comparing the amount of antibody-antigen complex in the test sample to a control;
wherein detecting antibody-antigen complex in the test sample as compared to the control indicates that the sample comprises TDP-43 comprising TTEQ (SEQ ID NO:1) or related epitope such as TTE (e.g. misfolded TDP-43).

In an embodiment, the sample is a biological sample. In an embodiment, the sample comprises brain tissue, spinal cord tissue or an extract thereof and/or CSF. In an embodiment, the sample is obtained from a human subject.

In an embodiment, the sample is from a subject with ALS. In another embodiment, the sample is from a subject with FTD.

A number of methods can be used to determine if misfolded TDP-43 polypeptides is present in a sample using the antibodies described herein, including immunoassays such as flow cytometry, dot or slot blots, Western blots, ELISA, and immunoprecipitation followed by SDS-PAGE immunocytochemistry. In an embodiment, the method used comprises one or more of the steps described in Example 7, 8 or 10.

Surface plasmon resonance can be used to assess conformation specific binding.

A labelled antibody described herein can also be administered to a subject detect location of misfolded TDP-43.

A further aspect includes a method of inducing an immune response in a subject, comprising administering to the subject a compound, immunogen and/or composition comprising a compound described herein; and optionally isolating cells and/or antibodies that specifically bind the compound or immunogen administered. The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

TDP-43 Epitope Predictions

Although most ALS/FTD mutations are in the C-terminus, the effects of mutation can lead to pathological aggregates of TDP-43, and these multimeric aggregates can induce the disorder of the structured domains. Accordingly, the RRM1 domain was assessed for the presence of conformation specific epitopes present in misfolded TDP-43.

Putative misfolded epitopes in TDP-43 were predicted with the aid of a method referred to as "Collective Coordinates biasing" which is described in WO/2017/079836, SYSTEMS AND METHODS FOR PREDICTING MISFOLDED PROTEIN EPITOPES BY COLLECTIVE COORDINATE BIASING filed Nov. 9, 2016. As described therein, the method uses molecular-dynamics-based simulations which impose a global coordinate bias on a protein (or peptide-aggregate) to force the protein (or peptide-aggregate) to misfold and then predict the most likely unfolded regions of the partially unstructured protein (or peptide aggregate). Biasing simulations were performed and the solvent accessible surface area (SASA) corresponding to each residue index (compared to that of the initial structure of the protein under consideration). SASA represents a surface area that is accessible to $H_2O$. A positive change in SASA (compared to that of the initial structure of the protein under consideration) may be considered to be indicative of unfolding in the region of the associated residue index. Two other methods were used in addition to SASA to identify candidate epitopes. These were the loss of native contacts, defined by non-hydrogen atoms within a cut-off length, and root mean squared fluctuations (RMSF), measuring the extent of deviations about the average in a structural ensemble; here an increase in RMSF for some amino acids indicates an increase in the dynamics of those amino acids.

The methods were applied to the natively folded RRM1 domain of TDP-43 (PDB entry 4IUF).

Simulations were performed for each initial structure using the a method as described in WO/2017/079836 and the CHARMM force-field parameters described in: K. Vanommeslaeghe, E. Hatcher, C. Acharya, S. Kundu, S. Zhong, J. Shim, E. Darian, O. Guvench, P. Lopes, I. Vorobyov, and A. D. Mackerell. Charmm general force field: A force field for drug-like molecules compatible with the charmm all-atom additive biological force fields. *Journal of Computational Chemistry,* 31(4):671-690, 2010; and P. Bjelkmar, P. Larsson, M. A. Cuendet, B. Hess, and E. Lindahl. Implementation of the CHARMM force field in GROMACS: analysis of protein stability effects from correlation maps, virtual interaction sites, and water models. *J. Chem. Theo. Comp.,* 6:459-466, 2010, both of which are hereby incorporated herein by reference, with TIP3P water as solvent.

I. Conformation Specific Epitopes

This disclosure pertains to antibodies that may be selective for misfolded TDP-43.

A prerequisite for the generation of misfolding-specific antibodies is the identification of targets on TDP-43 peptide that are not present (e.g. not accessible to binding) in the context of the native structure. These misfolding-specific epitopes would not differ in primary sequence from the corresponding segment in native TDP-43, however they would be conformationally distinct in the context of the misfolded protein. That is, they would present a distinct conformation in the misfolded protein that would not be present in the natively folded protein.

Antibodies directed either against native ensemble regions tend not to be selective for misfolded protein, and thus bind to healthy protein as well. Because the concentration of normal protein may be substantially higher than that of misfolded protein, such antibodies would likely suffer from "target distraction", primarily binding to healthy protein and promoting clearance of functional TDP-43, rather than selectively targeting and clearing misfolded proteinic species. This may interfere with critical RNA binding and stress response functions vital to the survival of the cell.

To develop antibodies selective for misfolded proteinic forms of TDP-43, a region in the native protein that is likely to be disrupted upon application of external perturbing forces was identified, using the Collective Coordinates algorithm. Without wishing to be bound to theory, it was hypothesized that disruptions in the context of the native may be exposed as well on the surface of the misfolded protein. On misfolded proteins however, these sequence regions may be exposed in conformations distinct from native TDP-43. For example, being on the surface, they may be exposed in turn regions that have higher exposed surface area, different dihedral angle distribution and/or overall different conformational geometry as determined by structural alignment than the corresponding quantities exhibit in either the native ensemble.

Cyclic compounds comprising TTEQ (SEQ ID NO: 1) and TTE are described herein. The cyclic compounds have been designed to satisfy one or more of the above criteria.

II. Epitope Predictions

The epitopes TTEQ (SEQ ID NO: 1) and TTE emerge as predicted epitopes.

Figure 1B:
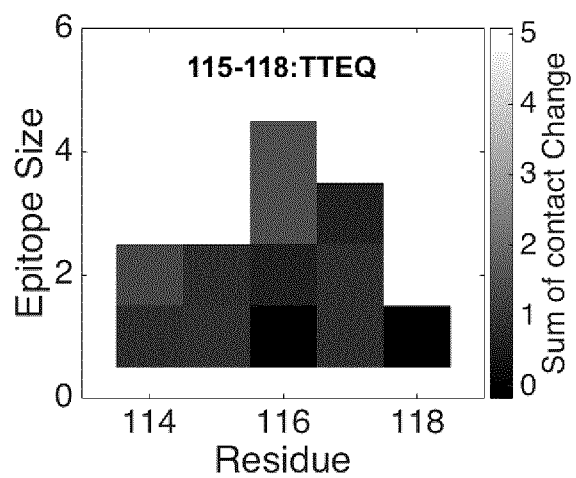
Figure 1C:
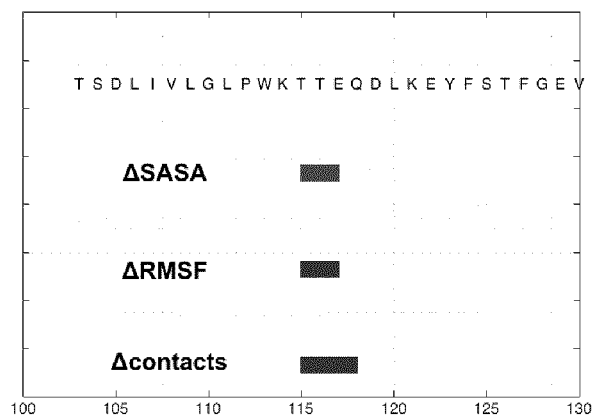
Figure 2A:
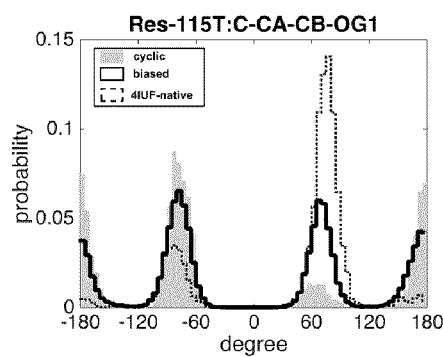
FIGS. 2A-J are graphs that show the Dihedral angle distributions for several dihedral angles that may conformationally distinguish misfolded TTEQ (SEQ ID NO: 1) from natively folded TTEQ (SEQ ID NO: 1). Distributions of the native ensemble (dotted line), biased ensemble (solid line) (a representation of misfolded RRM1 of TDP-43), and cyclic CGGTTEQGG (SEQ ID NO: 2) (shaded histogram) scaffold (for use in conjugating to an immunogen) are shown for the following dihedral angles def butions are included.
Figure 2B:
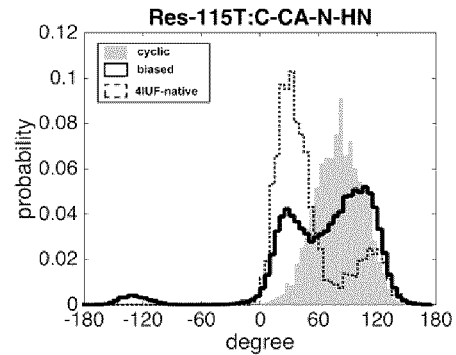
Figure 2C:
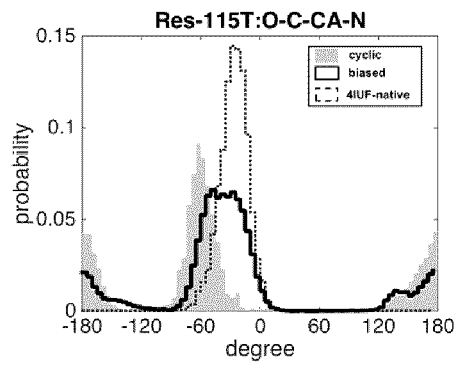
Figure 2D:
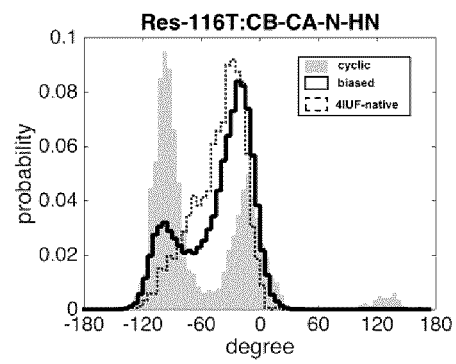
Figure 2E:
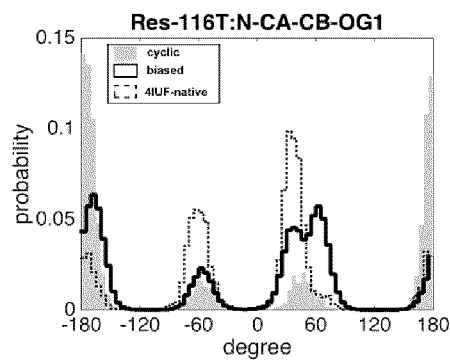
Figure 2F:
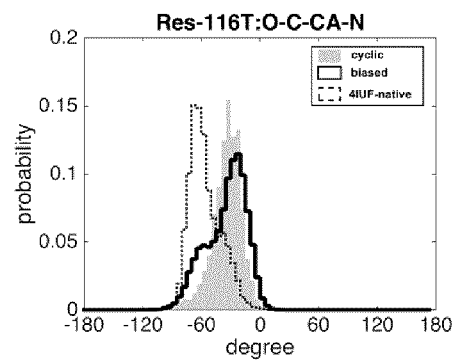
Figure 2G:
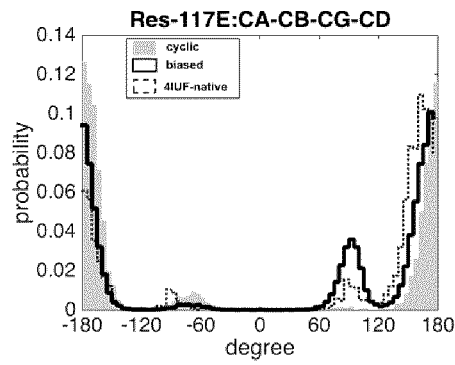
Figure 2H:
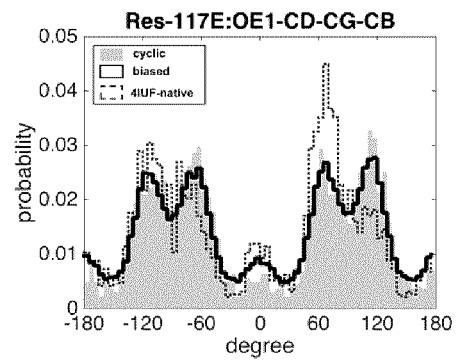
Figure 2I:
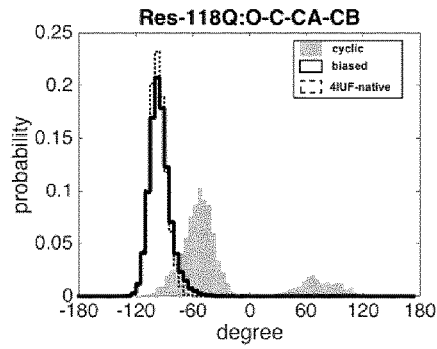
Figure 2J:
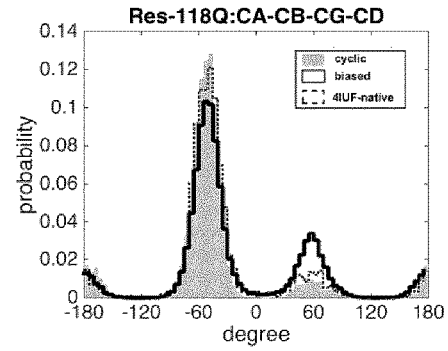
Figure 3A:
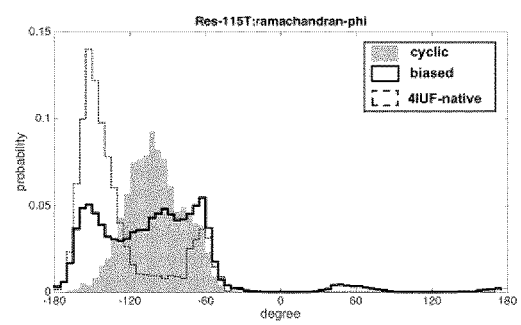
Figure 3B:
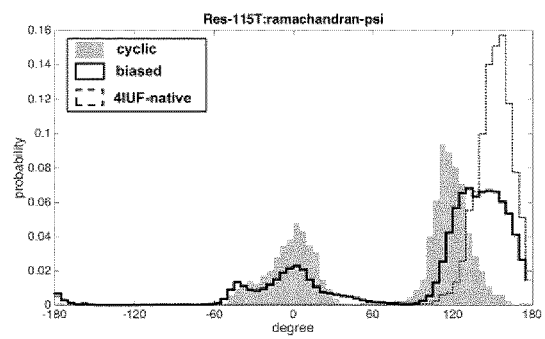
Figure 3C:
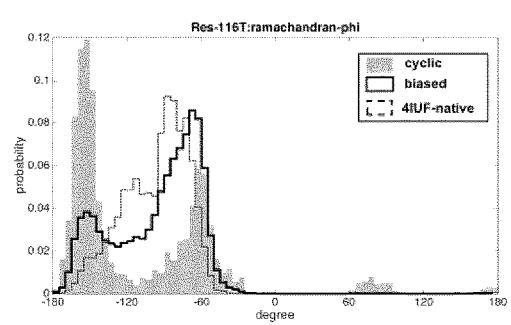
Figure 3D:
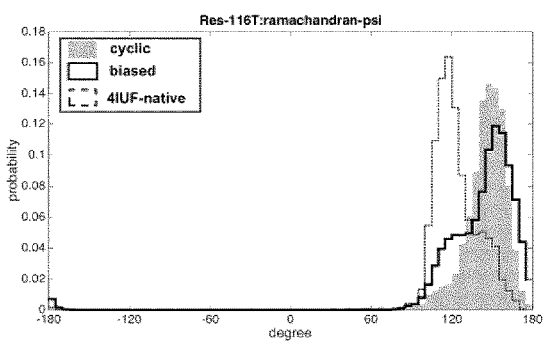
Figure 3E:
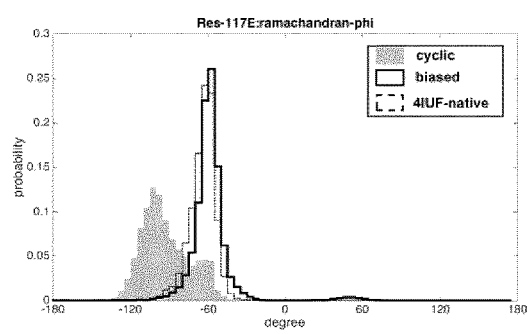
Figure 3F:
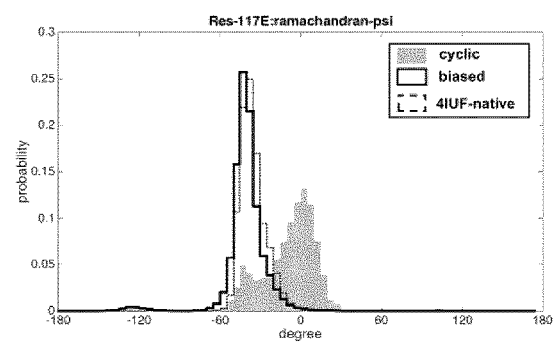
Figure 3G:
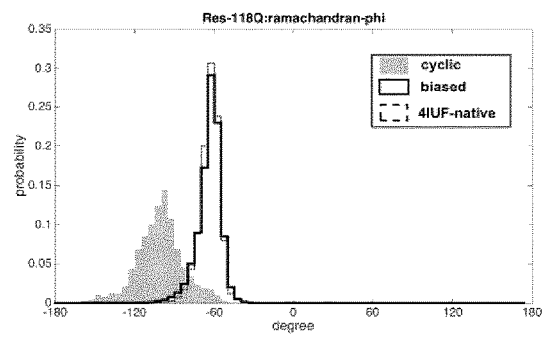
Figure 3H:
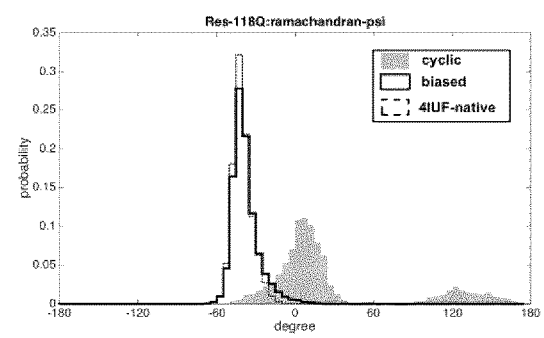

The TTEQ (SEQ ID NO: 1) epitope emerges as a prediction for PDB structure 4IUF when considering loss of native contacts. (FIG. 1 Panel B). TTE emerges as an epitope for structure 4IUF when considering increased SASA. TTE emerges as an epitope for structure 4IUF when considering increased RMSF.

For the plots in FIGS. 1-9 discussed herein, the data are obtained from equilibrium simulations in explicit solvent (TIP3P) using the Charmm36 force field. The simulation time and number of configurations for each ensemble are as follows. Cyclic peptide ensemble: simulation time 100 ns, containing 5000 frames in total; Biased ensemble: simulation time 90 ns for each unfolding trajectory; trajectories were repeated run 10 times (equivalently 90'10=900 ns), containing 40000 frames in total. 8000 frames were uniformly sampled from the 40000 frames for simplicity. Native 4IUF ensemble: 140 ns, containing 7000 frames.

III. Dihedral Angle Distributions

Further computational support for the identification of a misfolded protein-selective epitope, is provided by both the side chain dihedral angle distributions, and the Ramachandran, $\phi$ and $\psi$ distributions for the backbone dihedral angles in the cyclic peptide, a proxy for an exposed epitope in the misfolded protein. Some angles have substantially different distributions than the corresponding distributions in native TDP-43.

The side-chain and backbone dihedral distributions were examined for the four residues T115, T116, E117, and Q118. Percent overlap of distribution e.g. "native" in distribution "cyclic" is obtained by dividing the angles into elements of 5°, then decreasing a cutoff in probability amplitude from infinity, until 90% of the cyclic distribution is above the cutoff, and 10% remains below. This defines one or more regions in the allowable angles. Percent of the native distribution within this region was then found. The recipe is non-reciprocal and generally yields different numbers between pairs of distributions. The average of the overlaps, e.g. average of both native in cyclic and cyclic in native, is generally considered.

As shown in FIG. 2, for residue T115, dihedrals C—CA-CB-OG1, C—CA-N—HN, O—C—CA-N clearly distinguish the cyclic peptides of TTEQ (SEQ ID NO: 1) from the corresponding dihedral angles in the native ensemble. For residue T116, dihedral angle O—C—CA-N distinguishes the cyclic dihedral angle distribution from the corresponding distribution in the native ensemble. As shown in Table 1B, the dihedral overlap between the cyclic and biased ensemble is significantly increased over the overlap between the cyclic and native ensemble, for residues T115 and T116.

According to FIG. 3, the backbone Ramachandran angles $\phi$ and $\psi$ of T115 and T116 distinguishes the cyclic peptide from the native ensemble. For E117 and Q118, the cyclic peptide distribution is distinct from but has overlap with the native and biased distributions, which are not significantly distinct from each other.

From the dihedral distributions shown in FIG. 2, the probability that the native ensemble occupies a dihedral within the range of almost all (90%) of the cyclic peptide dihedral angles may be found. Likewise, the probability that the cyclic ensemble occupies a dihedral within the range of almost all (90%) of the native peptide dihedral angles may be found. The average of these over select dihedral angles in FIG. 2 is, for the residues TTEQ (SEQ ID NO:1): T115: O—C—CA-N 28%; T115: C—CA-CB-OG1, 53%. All overlap probabilities are given in Table 1A. For residues T115 and T116, the overlap between the cyclic and biased ensembles is generally higher than the overlap between the cyclic and native ensembles.

The accumulation of relatively small differences in individual dihedral angles can result in a large and significant difference in global conformation of the peptide, and thus significant deviations in the structural alignment, as described further below.

Based on FIG. 2, Table 1A shows the percent overlap of dihedral angle distributions for backbone and side-chain angles of residues T115, T116, E117, and Q118 in linear, cyclic peptide cyclo(CGGTTEQGG) (SEQ ID NO: 2) and native (4IUF) forms relative to each other. Column 1 is the specific dihedral angles considered. Columns 2-7 represent the percentage overlap of dihedral angle considered of one ensemble in another ensemble. For instance, column 2 shows the percentage overlap between a given dihedral angle in the native ensemble and the same angle in the cyclic peptide cyclo(CGGTTEQGG) (SEQ ID NO: 2).

Table 1B is derived from the numbers in Table 1A. The numbers in Table 1B show that the average overlap of the dihedral angle distributions between the cyclic and native forms is less than the average overlap of the dihedral angle distributions between the cyclic and biased forms, specifically for residues T115 and T116. This implies that residues T115 and T116 may be residues which confer the largest conformational selectivity against the native form.

TABLE 1A

Percent overlap of dihedral angle distribution, for cyclo (CGGTTEQGG) (SEQ ID NO: 2)

| Dihedral angle | Native in cyclic | Biased in cyclic | Cyclic in native | Biased in native | Cyclic in biased | Native in biased |
|---|---|---|---|---|---|---|
| 115T: C-CA-CB-OG1 | 57% | 81% | 49% | 63% | 91% | 89% |
| 115T: C-CA-N-HN | 40% | 64% | 63% | 72% | 98% | 94% |
| 115T: O-C-CA-N | 40% | 63% | 15% | 53% | 86% | 99% |
| 116T: CB-CA-N-HN | 75% | 84% | 47% | 76% | 82% | 95% |
| 116T: N-CA-CB-OG1 | 72% | 62% | 89% | 65% | 89% | 87% |
| 116T: O-C-CA-N | 51% | 82% | 69% | 61% | 95% | 91% |
| 117E: CA-CB-CG-CD | 76% | 74% | 90% | 84% | 87% | 86% |

TABLE 1A-continued

Percent overlap of dihedral angle distribution,
for cyclo (CGGTTEQGG) (SEQ ID NO: 2)

| Dihedral angle | Native in cyclic | Biased in cyclic | Cyclic in native | Biased in native | Cyclic in biased | Native in biased |
|---|---|---|---|---|---|---|
| 117E: OE1-CD-CG-CB | 87% | 85% | 89% | 85% | 93% | 93% |
| 118Q: CA-CB-CG-CD | 87% | 80% | 89% | 86% | 92% | 92% |
| 118Q: O-C-CA-CB | 41% | 47% | 7% | 85% | 10% | 98% |

TABLE 1B

Average overlap between cyclic and biased
or native, and corresponding difference

| Dihedral angle | average native-cyclic overlap | average biased-cyclic overlap | difference of (cyclic-biased) − (cyclic-native) |
|---|---|---|---|
| 115T:C-CA-CB-OG1 | 53% | 86% | 33% |
| 115T:C-CA-N-HN | 51% | 81% | 30% |
| 115T:O-C-CA-N | 27% | 75% | 47% |
| 116T:CB-CA-N-HN | 61% | 83% | 22% |
| 116T:N-CA-CB-OG1 | 81% | 75% | −6% |
| 116T:O-C-CA-N | 60% | 88% | 28% |
| 117E:CA-CB-CG-CD | 83% | 81% | −2% |
| 117E:OE1-CD-CG-CB | 88% | 89% | 1% |
| 118Q:CA-CB-CG-CD | 88% | 86% | −2% |
| 118Q:O-C-CA-CB | 24% | 28% | 4% |

Based on the data shown in FIG. 2, Table 2A lists the peak values of the dihedral angle distributions for those dihedral angles whose distributions show differences between the cyclic peptide cyclo(CGGTTEQGG) (SEQ ID NO: 2) and the native ensemble. Column 1 is the specific dihedral considered, column 2 is the peak value of the dihedral distribution for that angle in the context of the cyclic peptide cyclo(CGGTTEQGG) (SEQ ID NO: 2), column 3 is the peak value of the dihedral distribution for the peptide TTEQ (SEQ ID NO: 1) in the context of the native structural ensemble, column 4 is the peak value of the dihedral distribution for the peptide TTEQ (SEQ ID NO: 1) in the context of the biased structural ensemble, and column 5 is the difference of the peak values of the dihedral distributions for the cyclic and native ensembles. As shown in Table 2B, the differences are generally larger between the cyclic and native forms then they are between the cyclic and biased forms. Moreover, averaging over the various dihedral angles for a given residue, the magnitude of the difference (cyclic to native) minus (cyclic to biased) is largest for T115, and decreases monotonically from T115 to Q118.

TABLE 2A

Peak Values of the Dihedral Angle
Distributions, for cyclic
CGGTTEQGG (SEQ ID NO: 2)

| Dihedral angle | Cyclic | Native | Biased | Cyclic-Native difference |
|---|---|---|---|---|
| 115T: C-CA-CB-OG1 | −80 | 80 | −75 | −160 |
| 115T: C-CA-N-HN | 85 | 35 | 110 | 50 |
| 115T: O-C-CA-N | −60 | −25 | −45 | −35 |
| 116T: CB-CA-N-HN | −95 | −25 | −20 | −70 |
| 116T: N-CA-CB-OG1 | −175 | 35 | −165 | 150 |
| 116T: O-C-CA-N | −30 | −65 | −20 | 35 |
| 117E: CA-CB-CG-CD | −175 | 165 | 175 | 20 |
| 117E: OE1-CD-CG-CB | 115 | 70 | 120 | 45 |
| 118Q: CA-CB-CG-CD | −45 | −45 | −50 | 0 |
| 118Q: O-C-CA-CB | −50 | −95 | −95 | 45 |

TABLE 2B

Differences in peak values between cyclic,
native, biased and averages over residues

| Dihedral | cyclic-native | cyclic-biased | \|cyclic-native\| − \|cyclic-biased\| | average difference over residues |
|---|---|---|---|---|
| 115T:C-CA-CB-OG1 | −160 | −5 | 155 | 66.7 |
| 115T:C-CA-N-HN | 50 | −25 | 25 | |
| 115T:O-C-CA-N | −35 | −15 | 20 | |
| 116T:CB-CA-N-HN | −70 | −75 | 5 | 56.7 |
| 116T:N-CA-CB-OG1 | 150 | −10 | 140 | |
| 116T:O-C-CA-N | 35 | −10 | 25 | |
| 117E:CA-CB-CG-CD | 20 | 10 | 10 | 25 |
| 117E:OE1-CD-CG-CB | 45 | −5 | 40 | |
| 118Q:CA-CB-CG-CD | 0 | 5 | 5 | 2.5 |
| 118Q:O-C-CA-CB | 45 | 45 | 0 | |

IV. Ramachandran Angles

The backbone orientation that the epitope exposes to an antibody differs depending on whether the peptide is in the cyclic, biased, or native form. This discrepancy can be quantified by plotting the Ramachandran angles phi and psi (or $\phi$ and $\psi$), along the backbone, for each residue T115, T116, E117 and Q118 in the above 3 ensembles. FIG. 3 plots the phi and psi angles sampled in equilibrium simulations, for residues T115, T116, E117 and Q118. From FIG. 3 panels A and B, it can be seen that the distributions of backbone dihedral angles for T115 and T116 in the cyclic peptide are different from the distributions of dihedral angles sampled for either the native ensemble, and more similar to the biased ensemble. This is further quantified in Table 3A.

The overlap of the Ramachandran angle distributions, as defined above, is given in Table 3A. Table 3A shows the overlap probabilities of Ramachandran angles of the residues T115, T116, E117, and Q118 presented in FIG. 3. Specifically, the average of the fraction of the cyclic peptide cyclo(CGGTTEQGG) (SEQ ID NO: 2) ensemble that adopts conformations consistent with the native ensemble and the fraction of native ensemble that adopts conformations consistent with the cyclic ensemble is 28%, 63%, 55%, 23% for T115, T116, E117, and Q118 respectively. This is obtained by averaging both the psi and phi overlap numbers. This indicates for example that the orientations around T115 and Q118 in the cyclic peptide ensemble are conformationally distinct from conformations of those residues in the native ensemble.

Table 3B shows the overlap probabilities, averaged over both Ramachandran angles, and averaged for example in column 2 for cyclic in native, and native in cyclic; likewise column 3 averages over phi, psi, cyclic in biased and biased in cyclic of Table 3A, to achieve a net overlap percentage for a given residue Table 3B shows that the Ramachandran angles of T115 and T116 confer the greatest conformational selectivity against the native form, and towards biased, misfolded forms.

TABLE 3A

Overlap probabilities for Ramachandran angles phi and psi, for cyclic CGGTTEQGG (SEQ ID NO: 2).

| | cyclic in native | native in cyclic | cyclic in biased | biased in cyclic | biased in native | native in biased |
|---|---|---|---|---|---|---|
| phi | | | | | | |
| 115T | 42% | 31% | 98% | 61% | 60% | 94% |
| 116T | 35% | 80% | 82% | 89% | 77% | 93% |
| 117E | 24% | 87% | 25% | 71% | 83% | 93% |
| 118Q | 8% | 36% | 12% | 37% | 87% | 96% |
| psi | | | | | | |
| 115T | 12% | 28% | 85% | 59% | 51% | 99% |
| 116T | 70% | 66% | 94% | 83% | 63% | 81% |
| 117E | 23% | 87% | 30% | 73% | 84% | 97% |
| 118Q | 6% | 43% | 8% | 50% | 88% | 98% |

TABLE 3B

Average overlap probabilities for Ramachandran angles, for cyclic CGGTTEQGG (SEQ ID NO: 2), native and biased protein

| Residue | avg of cyclic-native | avg of cyclic-biased | difference of (cyclic-biased) − (cyclic-native) |
|---|---|---|---|
| 115T | 28% | 76% | 48% |
| 116T | 63% | 87% | 24% |
| 117E | 55% | 50% | −6% |
| 118Q | 23% | 27% | 3% |

Table 4A gives the peak (most-likely) values of the Ramachandran $\phi, \psi$ angles plotted in FIG. 3 for residues T115, T116, E117 and Q118. The $2^{nd}$, $3^{rd}$, and $4^{th}$ columns indicate the peak values of the Ramachandran phi/psi angles for each residue in the context of the cyclic peptide cyclo (CGGTTEQGG) (SEQ ID NO: 2), native ensemble, and non-native biased ensemble respectively. The most-likely Ramachandran phi and psi values are different between the cyclic and native ensembles for residues T115, T116, E117 and Q118. As shown in Table 4B, the differences are slightly larger between the cyclic and native forms then they are between the cyclic and biased forms. When averaged over phi and psi angles, T115 shows the greatest distinction between the above differences, so that the cyclic has stronger overlap with the biased form than the native from specifically for residue T115.

TABLE 4A

Peak values of distributions of backbone phi/psi angles (degrees)

| phi | Cyclic | native | biased |
|---|---|---|---|
| 115T | −100 | −150 | −60 |
| 116T | −150 | −85 | −65 |
| 117E | −100 | −60 | −55 |
| 118Q | −95 | −60 | −60 |

| psi | cyclic | native | biased |
|---|---|---|---|
| 115T | 115 | 160 | 135 |
| 116T | 150 | 120 | 155 |

TABLE 4A-continued

Peak values of distributions of backbone phi/psi angles (degrees)

| | | | |
|---|---|---|---|
| 117E | 5 | −35 | −40 |
| 118Q | 10 | −40 | −40 |

TABLE 4B

Differences cyclic to native, cyclic to biased, and difference between those differences, for the numbers in Table 4A.

| Residue | avg cyclic-native | avg cyclic-biased | \|cyclic-native\| − \|cyclic-biased\| |
|---|---|---|---|
| 115T | 47.5 | 30 | 17.5 |
| 116T | 47.5 | 45 | 2.5 |

TABLE 4B-continued

Differences cyclic to native, cyclic to biased, and difference between those differences, for the numbers in Table 4A.

| Residue | avg cyclic-native | avg cyclic-biased | \|cyclic-native\| − \|cyclic-biased\| |
|---|---|---|---|
| 117E | 40 | 45 | −5 |
| 118Q | 42.5 | 42.5 | 0 |

V. Solubility and Solvent-Exposure of the Epitope

Figure 4A:
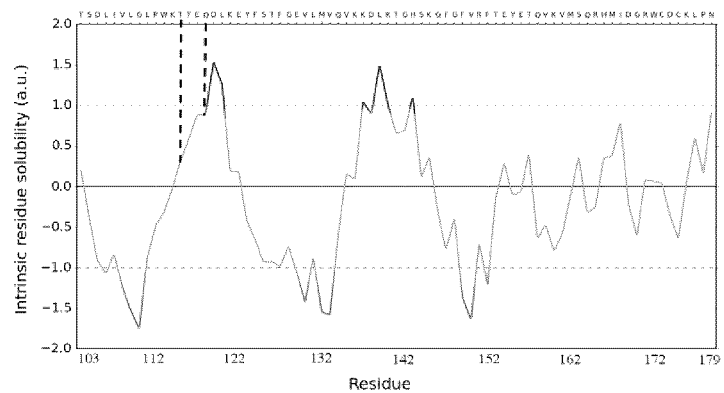

FIG. 4 Panel A plots the intrinsic solubility of each amino acid in TDP-43 RRM1. It can be seen that the epitope sequence TTEQ (SEQ ID NO: 1) is among one of the more soluble regions in the protein sequence, indicating that upon biasing forces implementing an external challenge to the protein structure, that particular region will not be averse to increasing it's solvent accessibility.

FIG. 4 Panel B and Table 5 gives the mean solvent accessible surface area (SASA) of each residue in the equilibrium ensemble of the cyclic peptide; the biased, partially unfolded protein ensemble; and the native ensemble. This shows that the SASA of residues TTEQ (SEQ ID NO: 1) in the biased ensemble is increased over the native, and as well, the SASA of the cyclic peptide is increased over that in the biased ensemble, indicating more surface would be exposed and thus accessible to antibody binding. The increase in exposure is most significant for residues T115 and E117, which shows the largest increase in SASA over the native ensemble. For T115, this difference is 101 Å$^2$, while for E117, this difference is 67 Å$^2$.

Figure 4B:
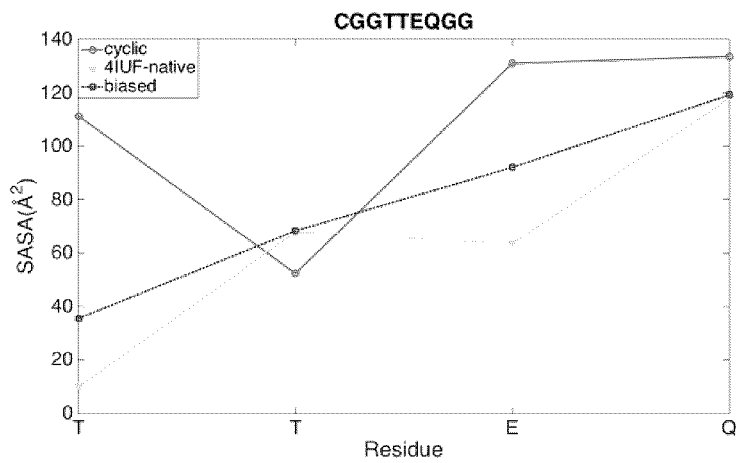
Figure 4C:
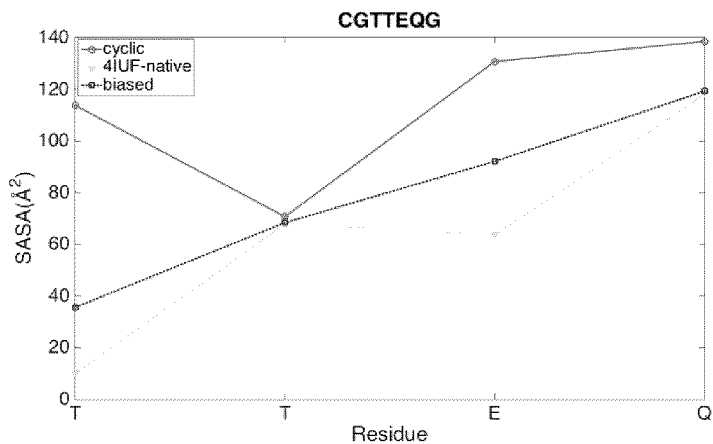

FIG. 4C gives the mean SASA of each residue as in FIG. 4B, but now for the cyclic peptide of sequence cyclo (CGTTEQG) (SEQ ID NO: 3). The results recapitulate those for cyclic peptide cyclo(CGGTTEQGG) (SEQ ID NO:2).

Table 5 shows the SASA of residues T115, T116, E117, and Q118 in the context of the cyclic cyclo(CGGTTEQGG) (SEQ ID NO: 2) ensemble, the biased ensemble, and the native ensemble.

TABLE 5

SASA by residue, and total SASA, for native, biased and cyclic CGGTTEQGG (SEQ ID NO: 2) ensembles
SASA by residue, and total (Å$^2$)

| CGGTTEQGG (SEQ ID NO: 2) | cyclic | biased | native |
|---|---|---|---|
| 115T | 111.3 | 35.5 | 10.3 |
| 116T | 52.3 | 68.3 | 68.2 |
| 117E | 131 | 92 | 64 |
| 118Q | 133.6 | 119.2 | 119.3 |
| Total | 428.2 | 315 | 261.8 |

Figure 7A:
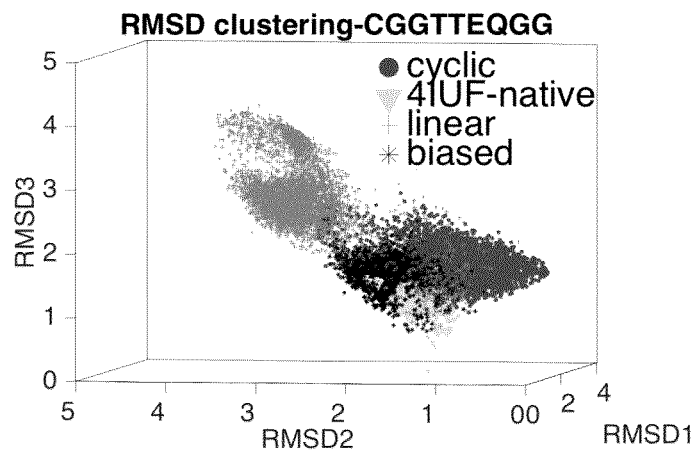
FIG. 7H plots the same correlation coefficient for cyclic peptide cyclo(CGTTEQG) (SEQ ID NO: 3) ensemble and the native ensemble, which converges to about 8% when 100% of the respective distributions are included.
FIG. 7I examines the effects of single residue deletions on the structural overlap between the cycloCGGTTEQGG (SEQ ID NO: 2) ensemble and the native ensemble. The average of the overlaps, cyclic in native and native in cyclic, as defined above, is used. The x-axis corresponds to the number of sampled conformations and is used as a measure of convergence of the result; the ordinate value at the largest value of the abscissa is the most reliable value.
FIG. 7J corresponds to cyclic peptide cyclo (CGTTEQG) (SEQ ID NO: 3). The conclusion is the same for this epitope scaffold: T115 confers significant conformational sel PDB entry 4IUF. The PDB 4IUF structure can be equilibrated on a computer to obtain an equilibrium ensemble, which was used for all measurements of the native conformations of the epitopes in the native structure of TDP-43, referred to herein variably as "native structure of RRM1", "equilibrium native ensemble of TDP-43", "equilibrium native ensemble of RRM1 of TDP-43", or "TDP-43 native structural ensemble".
Figure 7B:
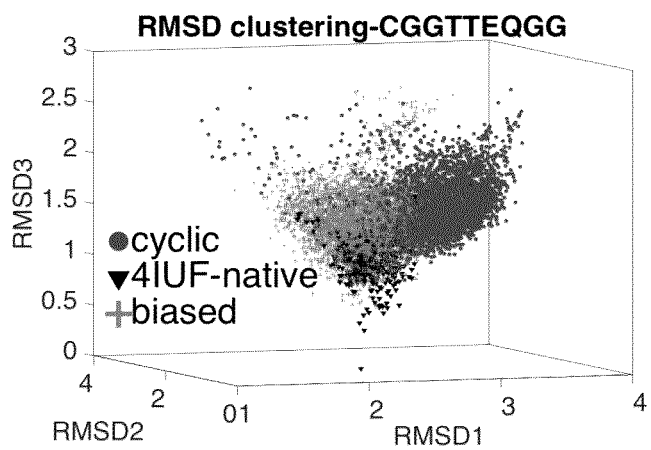
Figure 7C:
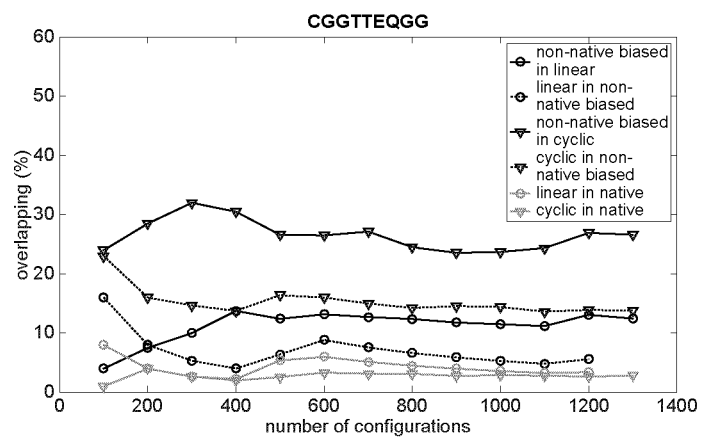
Figure 7D:
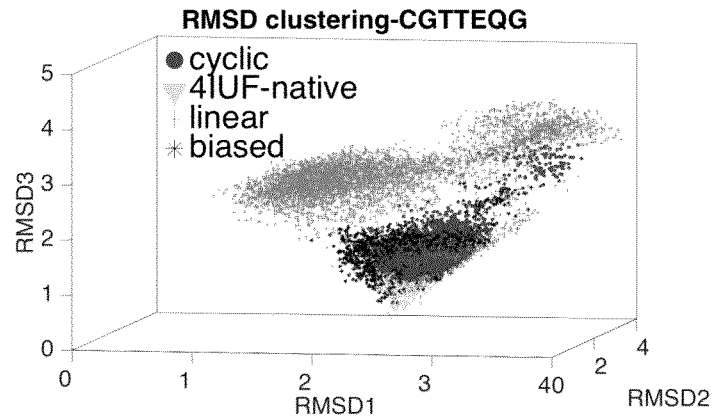
Figure 7E:
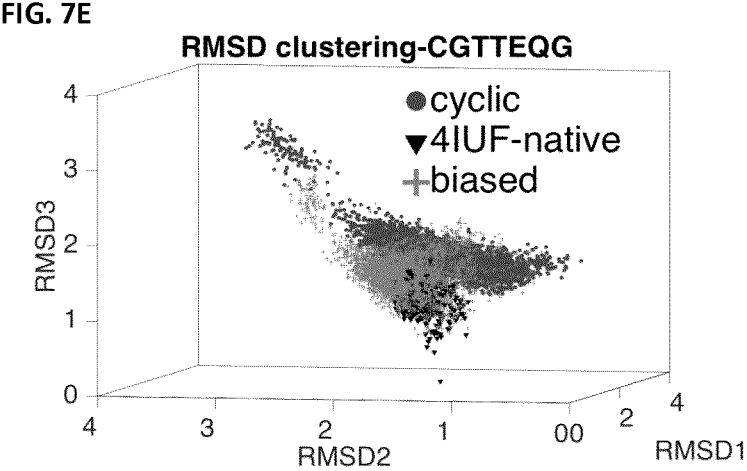
Figure 7F:
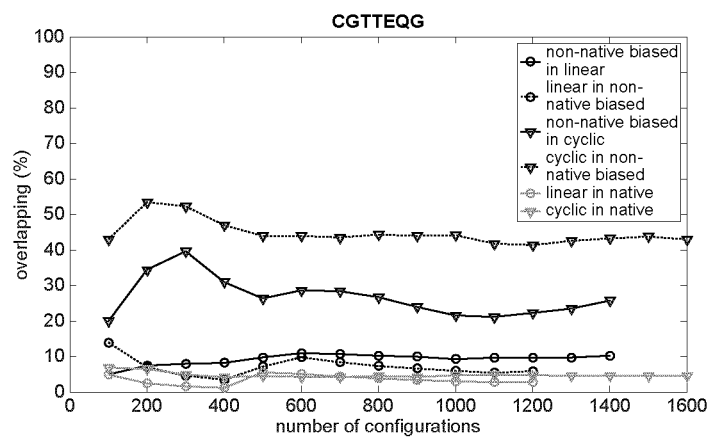

VI. The Ensemble of Cyclic Peptide Conformations Clusters Differently than the Ensemble of Either Linear or Fibril Conformations Definitive evidence that the sequence TTEQ (SEQ ID No: 1) displays a different conformation in the context of the cyclic peptide than in the native ensemble can be seen by using standard structural alignment metrics between conformations, and then implementing clustering analysis. Equilibrium ensembles of conformations are obtained for the native RRM1 (PDB 4IUF), biased RRM1, and cyclic peptides cyclo(CGGTTEQGG) (SEQ ID No: 2). Snapshots of conformations from these ensembles for residues TTEQ (SEQ ID NO: 1) are collected and then structurally aligned to the centroids of the largest cluster of the cyclic peptide ensemble, the largest cluster of the native ensemble, and the largest cluster of TTEQ (SEQ ID NO: 1) in the biased ensemble; the three values of the root mean squared deviation (RMSD) are then recorded and plotted. The clustering is performed here by the maxcluster algorithm. The 3 corresponding RMSD values for the cyclic, biased, and native ensembles are plotted as a 3-dimensional scatter plot in FIG. 7. FIG. 7 Panel A also includes results for an equilibrium ensemble of the linear peptide CGGTTEQGG (SEQ ID NO: 2). FIG. 7C plots the overlap percentages between several ensembles. Two overlap numbers are particularly important. One is the overlap with the cyclic or native ensemble ensembles with the non-native biased ensemble. The non-native biased ensemble is the part of the biased ensemble that does not include configurations overlapping with the native ensemble. I.e. any biased conformations that overlap with part of the native ensemble are removed, so it is those biased conformations that are different than native conformations. The higher this number, the better that epitope scaffold at selectively targeting locally unfolded states. The overlap between cyclic peptide ensemble and non-native biased ensemble is larger than the overlap between linear peptide ensemble and non-native biased ensemble. This justifies the use of using the cyclic scaffold as a proxy for non-native misfolded states. The cyclic peptide has substantially larger overlap with the non-native biased ensemble than it does with the native ensemble.

The other number that is important is the overlap between either the cyclic or linear structural ensembles with the native structural ensemble. This number should be low. The lower this number, the less that antibodies raised to the epitope scaffold will target the native structure. The numeric overlapping percentages are given in Table 6A. It is evident from FIG. 7 and Table 6A below that the 3 ensembles cluster differently from each other. In particular, the cyclic peptide structural ensemble is distinct from the native ensemble, implying that antibodies specific to the cyclic peptide epitope may have low affinity to the conformations presented in the linear or native ensembles. An antibody raised to the cyclic peptide could be conformationally selective and preferentially bind misfolded proteinic forms over the native conformations of TDP-43. The distinction between the ensembles occurs in spite of the overlap between several side chain and backbone dihedral angle distributions; the numerous often small differentiating features described above lead to globally different conformational distributions.

FIG. 7 Panels D, E, F plots the corresponding quantities as FIG. 7 A, B, C, but now for cyclic peptide cyclo (CGTTEQG) (SEQ ID NO:3). The results are similar to the above: The cyclic peptide has substantially larger overlap with the non-native biased ensemble than it does with the native ensemble, and the cyclic peptide is a better epitope scaffold for non-native biased states than is the linear peptide.

Table 6A gives the overlap percentages in the RMSD clustering scatter plot of the cyclic, biased, and native (4IUF) peptide conformations, as presented in FIG. 7. Column 1 shows the percentage overlap from the cyclic to the native form is quite small, only 5% for CGGTTEQGG (SEQ ID NO: 2) and 4% for CGTTEQG (SEQ ID NO: 3). On the other hand, the percent overlap from the cyclic to the biased ensembles is almost 3 times greater, about 14% for CGGTTEQGG (SEQ ID NO: 2) and about 10× greater or 42% for CGTTEQG (SEQ ID NO: 3). The cyclic ensemble is sampling non-native-like conformations about 95% of the time.

The overlap of the cyclic peptide in the non-native biased ensemble gives the fraction of scaffolds in the equilibrium ensemble that accurately represent misfolded non-native states. Likewise, the overlap of the cyclic peptide in the native biased ensemble gives the fraction of scaffolds in the equilibrium ensemble that accurately represent native states. The overlap of the non-native biased ensemble in the cyclic peptide ensemble gives the similarity of non-native misfolded states to the cyclic ensemble, and likewise, the overlap of the native biased ensemble in the cyclic peptide ensemble gives the similarity of native misfolded states to the cyclic ensemble. This latter quantity is not of particular interest, however the reciprocal overlaps between biased ensemble and cyclic ensemble are both measures quantifying the appropriateness of using the cyclic scaffold. In Table 6B we take an average of these two measures, divided by the cyclic in native ensemble overlap as a measure of the goodness in using a given cyclic scaffold to target non-native misfolded states vs. the native to provide a goodness ratio for cyclic peptides in targeting non-native misfolded conformations vs. native conformations. Column 1 gives the sequence, column 2 gives the average of the overlap of the cyclic peptide in the non-native biased ensemble and the overlap of the non-native biased ensemble in the cyclic peptide ensemble, Column 3 gives the overlap of the cyclic peptide in the native ensemble, Column 4 gives the difference of Column 2 and Column 3, and Column 5 gives the ratio of Column 2 divided by Column 3, which is defined as the goodness ratio for the cyclic peptide construct.

TABLE 6A

Percentage overlap of RMSD clustering

| | cyclic in native | native in cyclic | cyclic biased in cyclic | biased in cyclic | native biased in biased | biased in native | non-native biased in cyclic | cyclic in non-native biased |
|---|---|---|---|---|---|---|---|---|
| CGGTTEQGG (SEQ ID NO: 2) | 5% | 19% | 14% | 24% | 85% | 30% | 25% | 14% |
| CGTTEQG (SEQ ID NO: 3) | 4% | 17% | 55% | 24% | 84% | 24% | 26% | 42% |

TABLE 6B

Goodness ratio for cyclic peptides in targeting non-native misfolded conformations vs. native conformations

| Sequence | A) avg cyclic-non-native biased overlap | B) cyclic scaffold in native | difference in A-B | Ratio B/A |
|---|---|---|---|---|
| CGGTTEQGG (SEQ ID NO: 2) | 20% | 5% | 15% | 3.9 |
| CGTTEQG (SEQ ID NO: 3) | 34% | 4% | 30% | 8.5 |

TABLE 6C

Goodness ratio for several candidate cyclic scaffolds

| cyclic sequence | cyclic in non-native biased | non-native biased in cyclic | cyclic in native | ratio |
|---|---|---|---|---|
| CGTTEQG (SEQ ID NO: 3) | 42% | 26% | 4% | 8.50 |
| CGGTTEQGG (SEQ ID NO: 2) | 25% | 14% | 5% | 3.90 |
| CGGTTEQGGG (SEQ ID NO: 22) | 10% | 42% | 8% | 3.25 |
| CGTTEQGG (SEQ ID NO: 23) | 28% | 42% | 15% | 2.33 |

TABLE 6D

Overlap between the cyclic and the linear forms

| Cyclic sequence | linear in cyclic | cyclic in linear |
|---|---|---|
| CGTTEQG (SEQ ID NO: 3) | 7.5% | 21% |
| CGGTTEQGG (SEQ ID NO: 2) | 12% | 24% |
| CGTTEG (SEQ ID NO: 28) | 12% | 39% |
| CGTTEGG (SEQ ID NO: 29) | 13% | 43% |

Table 6C lists the goodness ratio as defined in Table 6B—the ability of cyclic peptides to target non-native misfolded conformations vs. native conformations—for several candidate cyclic scaffolds as a function of several different cyclic radii, sorted in decreasing order of goodness ratio. Two cyclic scaffolds analyzed, constructs CGTTEQG (SEQ ID NO: 3) and CGGTTEQGG (SEQ ID NO: 2) have the largest goodness ratio, and so would be predicted to be the best proxies for non-native misfolded structures using these measures.

Table 6D lists the overlap percentage between the cyclic and linear conformational ensembles. The ensembles are different as seen by their small to moderate overlap percentage; this indicates that the cyclic peptide ensemble is conformationally distinct from the linear peptide ensemble, and also likely to be conformationally distinct from the nascent unfolded peptide chain.

The overlap between the ensembles was calculated as follows. The fraction (percent) of the biased ensemble that overlaps with the cyclic ensemble is obtained by first dividing the volume of this 3-dimensional RMSD space up into cubic elements of length 0.1 Angstrom. Then a "cutoff density" of points in the cyclic distribution is found such that the cubes with cyclic distribution density equal to or higher than the cutoff density contain 90% of the cyclic distribution. This defines a volume (which may be discontiguous) that gives the characteristic volume containing the cyclic distribution and removes any artifacts due to outliers. Then the fraction of points from the biased distribution that are within this region is found. With this method, it is possible to find the overlapping percentages for cyclic in native, cyclic in biased, etc.

FIG. 7 Panels C and F illustrate that the ensembles are large enough that the overlap values have converged.

FIG. 7 Panel G shows the correlation coefficient between both the cyclic-CGGTTEQGG (SEQ ID NO: 2) ensemble and the native ensemble, and the cyclic-CGGTTEQGG (SEQ ID NO: 2) ensemble and the non-native biased ensemble, computed as follows. The correlation coefficient between two ensembles is defined by first finding the parts of the distributions having density greater than a cutoff value, such that a given percentage of the total distributions are encompassed, e.g. a density cutoff for the cyclic and linear distributions that give 60% of the total distributions. Then for these subdistributions, the correlation coefficient is defined as $\int f(\tau)g(\tau)d\tau / \sqrt{\int f(\tau)^2 d\tau} \sqrt{\int g(\tau)^2 d\tau}$, where $f(\tau)$ and $g(\tau)$ are the densities in each voxel T and the result is integrated (summed) over all voxels. Thus defined, the correlation coefficient between the native and cyclic distributions converges to about 4.5% when 100% of the respective distributions are included, and the correlation coefficient between the non-native biased and cyclic distributions converges to about 10.5% when 100% of the respective distributions are included, or about double the overlap.

Figure 7G:
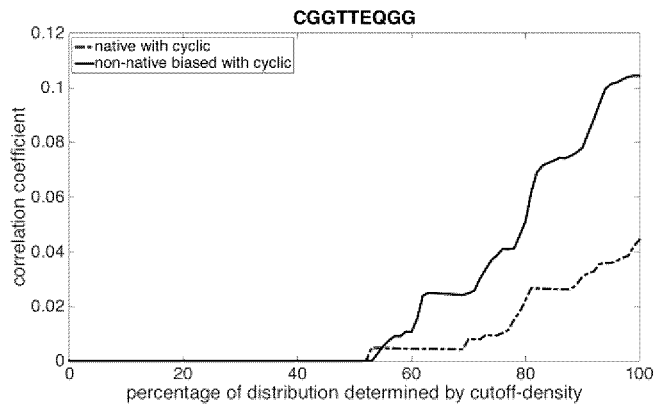
Figure 7H:
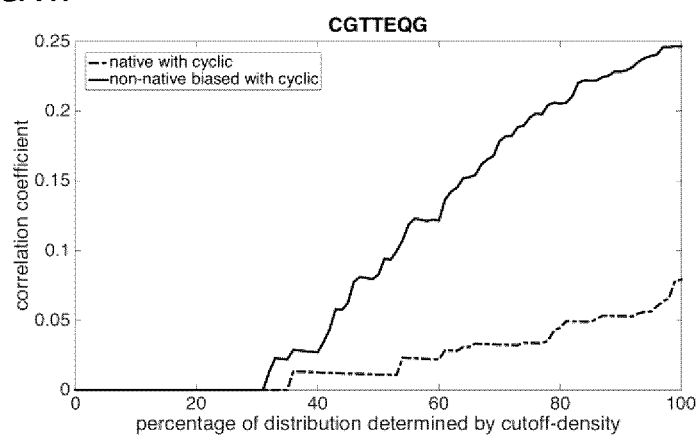

FIG. 7 Panel H shows the correlation coefficient between both the cyclic-(CGTTEQG) (SEQ ID NO: 3) ensemble and the native ensemble, and the cyclic-(CGTTEQG) (SEQ ID NO: 3) ensemble and the non-native biased ensemble, analogously to FIG. 7G. The correlation coefficient between the native and cyclic distributions converges to about 7% when 100% of the respective distributions are included, and the correlation coefficient between the non-native biased and cyclic distributions converges to about 25% when 100% of the respective distributions are included, or about 3.6 times the overlap.

FIG. 7 Panel I examines the effects of single residue deletions on the structural overlap, as defined by averaging the overlap of the native ensemble with the 90% cyclic (CGGTTEQGG) (SEQ ID NO: 2) ensemble, and the cyclic ensemble with 90% of the native ensemble. If a single amino acid confers conformational selectivity against the native conformation, then removing it from the structural alignment will result in a significantly higher overlap between the distributions. By this test, T115 stands out as conferring the most conformational selectivity to the cyclic peptide.

Figure 7I:
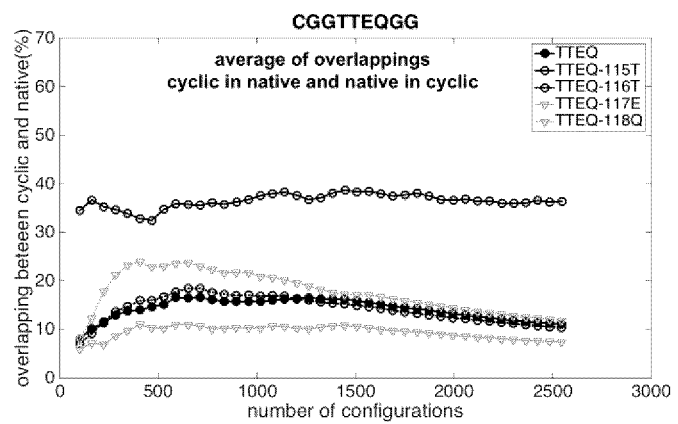
Figure 7J:
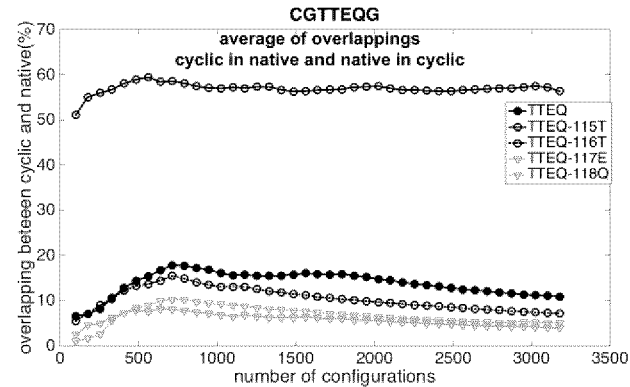
Figure 8A:
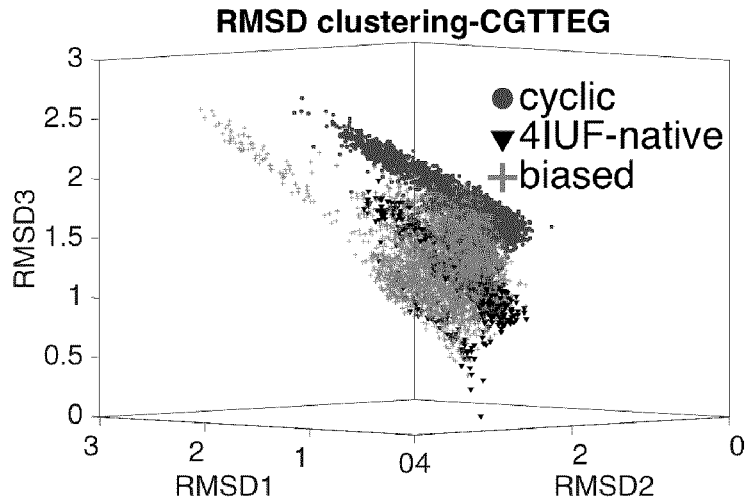
Figure 8B:
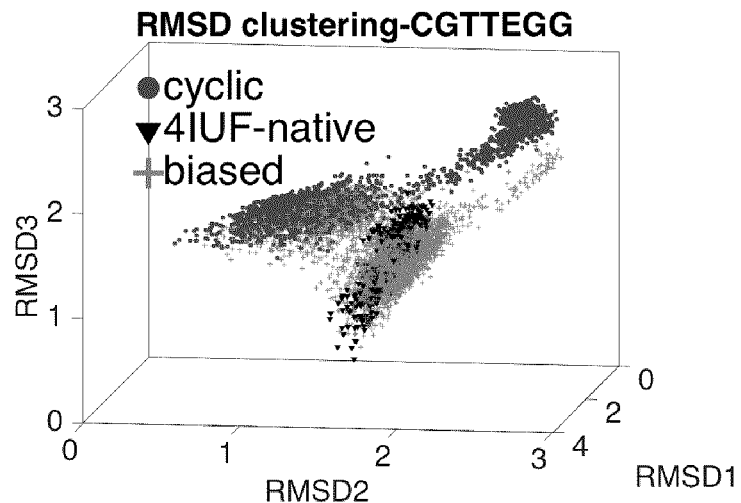

FIG. 7 Panel J plots the effects of single residue deletions for the cyclic peptide cyclo(CGTTEQG) (SEQ ID NO: 3), analogously with FIG. 7I. Again residue T115 stands out as conferring the conformational selectivity to the cyclic peptide.

Figure 5A:
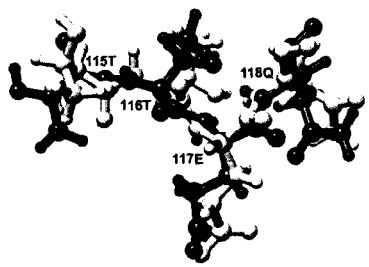
Figure 5B:
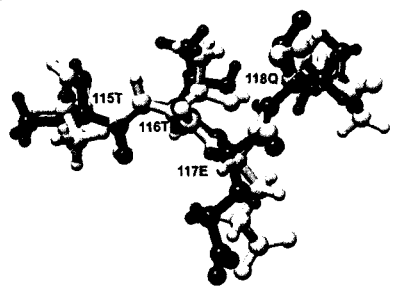
Figure 6A:
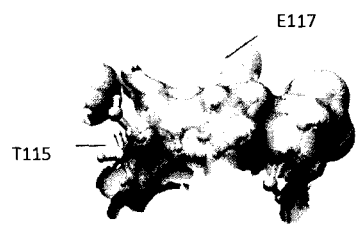
Figure 6B:
Figure 6C:
Figure 6D:
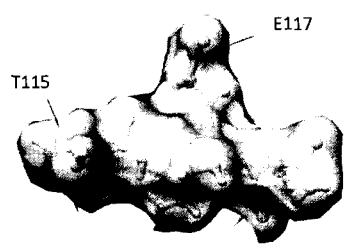
Figure 6E:
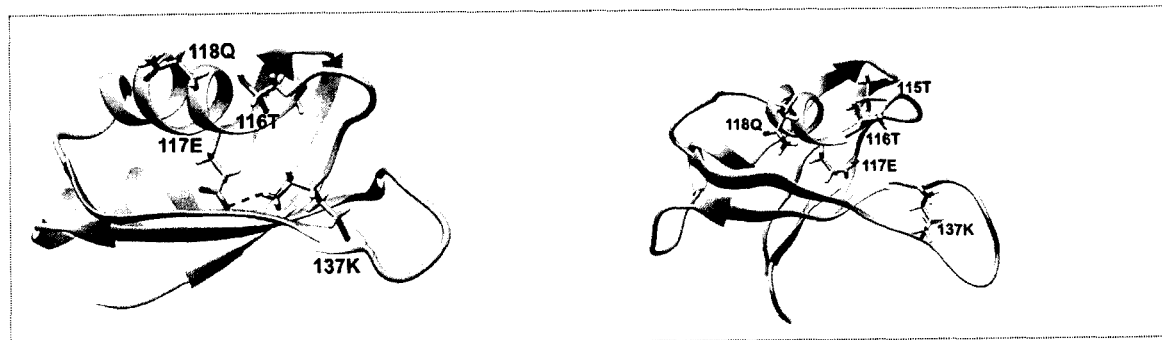

A schematic of the atomic structure of the most-representative conformation of TTEQ (SEQ ID NO: 1) from the cyclic peptide ensemble of CGGTTEQGG (SEQ ID NO: 2), constituting the centroid of the largest cluster from the cyclic peptide ensemble of structures, is shown in FIG. 5 Panel A in black. As well, the most-representative conformation in the native structural ensemble, constituting the centroid of the largest cluster, is shown in light grey in FIG. 5, optimally superimposed on the cyclic peptide shown in black by aligning them using RMSD, to make explicit their different orientations. In particular, T115 has a significantly different orientation between the two centroid conformations. FIG. 5 Panel B shows the corresponding centroid conformations for the cyclic peptide and native ensemble for the cyclic sequence CGTTEQG (SEQ ID NO: 3), again optimally superimposed by aligning with respect to RMSD. Both cyclic constructs show T115 is in an alternate conformation, and to a lesser extent Q118 appears in an alternate conformation.

Table 7 lists values of the Ramachandran backbone and side chain dihedral angles occupied by residues T115, T116, E117, and Q118 in the centroid structure of the cyclic CGGTTEQGG (SEQ ID NO: 2) peptide ensemble, the centroid structure of the native ensemble, and the centroid structure of the non-native biased ensemble; cyclic and native centroid conformations are plotted in FIG. 5. The centroid structures exhibit several dihedral angles that are substantially different between the cyclic conformation and the native conformation. Column 1 of Table 7 gives the residue and dihedral angle of interest, column 2 gives the value of the dihedral angle in the centroid structure of the cyclic ensemble, column 3 gives the value of the dihedral in the native ensemble centroid, column 4 gives the value of the dihedral in the non-native biased ensemble centroid, column 5 is the magnitude of the difference in cyclic and native dihedrals, column 6 is the magnitude of the difference in cyclic and non-native biased dihedrals, column 7 gives the values of column 5 averaged over the dihedrals in each amino acid and column 8 gives the values of column 6 averaged over the dihedrals in each amino acid. It is apparent that many of the cyclic dihedral angles are significantly different then the corresponding dihedral angles in the linear or native centroids, as described above for the peak values of the dihedral distributions. Note however that the dihedral angles of the centroid structures need not be the same as the peak values of the dihedral distributions. For an example of the differences here, the dihedral OG1-CB-CG2-2HG2 in residue 115T shows a difference of 100 degrees between the cyclic and native, but only 15 degrees between the cyclic and non-native biased. The average difference between cyclic and native for 115T is 87.6 degrees, while the average difference between cyclic and non-native biased for 115T is 51.9 degrees. Again note that these differences are only for one conformation in each of the respective ensembles—the centroid conformation.

TABLE 7

Dihedral angles in the centroid structures of the linear, cyclic, and native ensembles.

| Residue:Dihedral | cyclic | native | biased | cyclic-native | cyclic-biased | avg cyclic-native | avg cyclic-biased |
|---|---|---|---|---|---|---|---|
| 115T:C-CA-CB-CG2 | 60 | −25 | 0 | 85 | 60 | 87.6 | 51.9 |
| 115T:C-CA-CB-HB | −60 | −150 | −115 | 90 | 55 | | |
| 115T:C-CA-CB-OG1 | 180 | 95 | 130 | 85 | 50 | | |
| 115T:C-CA-N-HN | 75 | 25 | 65 | 50 | 10 | | |
| 115T:CA-CB-CG2-1HG2 | 60 | −50 | 45 | 110 | 15 | | |
| 115T:CA-CB-CG2-2HG2 | 175 | 80 | 170 | 95 | 5 | | |
| 115T:CA-CB-CG2-3HG2 | −65 | −165 | −70 | 100 | 5 | | |
| 115T:CA-CB-OG1-HG1 | 45 | 80 | 50 | 35 | 5 | | |
| 115T:CB-CA-N-HN | −45 | −100 | −60 | 55 | 15 | | |
| 115T:CG2-CB-OG1-HG1 | 170 | −155 | −175 | 145 | 165 | | |
| 115T:HA-CA-CB-CG2 | −50 | −150 | −110 | 100 | 60 | | |
| 115T:HA-CA-CB-HB | −170 | 90 | 130 | 80 | 120 | | |
| 115T:HA-CA-CB-OG1 | 70 | −25 | 15 | 95 | 55 | | |
| 115T:HA-CA-N-HN | −175 | 135 | 175 | 130 | 170 | | |
| 115T:HB-CB-CG2-1HG2 | −175 | 70 | 165 | 65 | 160 | | |
| 115T:HB-CB-CG2-2HG2 | −60 | −160 | −70 | 100 | 10 | | |
| 115T:HB-CB-CG2-3HG2 | 60 | −45 | 50 | 105 | 10 | | |
| 115T:HB-CB-OG1-HG1 | −80 | −40 | −65 | 40 | 15 | | |
| 115T:N-CA-CB-CG2 | 180 | 90 | 125 | 90 | 55 | | |
| 115T:N-CA-CB-HB | 60 | −35 | 10 | 95 | 50 | | |
| 115T:N-CA-CB-OG1 | −65 | −145 | −105 | 80 | 40 | | |
| 115T:O-C-CA-CB | 50 | 90 | 90 | 40 | 40 | | |
| 115T:O-C-CA-HA | 170 | −145 | −155 | 135 | 145 | | |
| 115T:O-C-CA-N | −70 | −30 | −40 | 40 | 30 | | |
| 115T:OG1-CB-CG2-1HG2 | −60 | −175 | −85 | 115 | 25 | | |
| 115T:OG1-CB-CG2-2HG2 | 55 | −45 | 40 | 100 | 15 | | |
| 115T:OG1-CB-CG2-3HG2 | 175 | 70 | 160 | 105 | 15 | | |
| 116T:C-CA-CB-CG2 | −55 | −70 | −75 | 15 | 20 | 68.1 | 58.7 |
| 116T:C-CA-CB-HB | −165 | 165 | 175 | 150 | 160 | | |
| 116T:C-CA-CB-OG1 | 75 | 45 | 55 | 30 | 20 | | |
| 116T:C-CA-N-HN | 45 | 85 | 100 | 40 | 55 | | |
| 116T:CA-CB-CG2-1HG2 | 80 | −30 | −60 | 110 | 140 | | |
| 116T:CA-CB-CG2-2HG2 | −155 | 85 | 60 | 60 | 35 | | |
| 116T:CA-CB-CG2-3HG2 | −40 | −150 | 175 | 110 | 35 | | |
| 116T:CA-CB-OG1-HG1 | 110 | 150 | 50 | 40 | 60 | | |
| 116T:CB-CA-N-HN | −70 | −45 | −25 | 25 | 45 | | |
| 116T:CG2-CB-OG1-HG1 | −120 | −85 | 180 | 35 | 120 | | |
| 116T:HA-CA-CB-CG2 | −170 | 175 | 175 | 165 | 165 | | |
| 116T:HA-CA-CB-HB | 80 | 55 | 65 | 25 | 15 | | |
| 116T:HA-CA-CB-OG1 | −45 | −65 | −55 | 20 | 10 | | |
| 116T:HA-CA-N-HN | 165 | −160 | −140 | 145 | 125 | | |
| 116T:HB-CB-CG2-1HG2 | −170 | 85 | 55 | 75 | 45 | | |
| 116T:HB-CB-CG2-2HG2 | −45 | −160 | 175 | 115 | 40 | | |
| 116T:HB-CB-CG2-3HG2 | 70 | −40 | −70 | 110 | 140 | | |
| 116T:HB-CB-OG1-HG1 | −10 | 40 | −65 | 50 | 55 | | |
| 116T:N-CA-CB-CG2 | 65 | 60 | 60 | 5 | 5 | | |
| 116T:N-CA-CB-HB | −45 | −65 | −50 | 20 | 5 | | |
| 116T:N-CA-CB-OG1 | −165 | 175 | −170 | 160 | 5 | | |
| 116T:O-C-CA-CB | 115 | 105 | 100 | 10 | 15 | | |
| 116T:O-C-CA-HA | −125 | −145 | −150 | 20 | 25 | | |
| 116T:O-C-CA-N | −5 | −25 | −30 | 20 | 25 | | |
| 116T:OG1-CB-CG2-1HG2 | −55 | −155 | 170 | 100 | 45 | | |
| 116T:OG1-CB-CG2-2HG2 | 70 | −40 | −75 | 110 | 145 | | |
| 116T:OG1-CB-CG2-3HG2 | −170 | 85 | 40 | 75 | 30 | | |
| 117E:C-CA-CB-CG | 180 | 165 | 175 | 15 | 5 | 52.2 | 63.3 |
| 117E:C-CA-CB-HB1 | −60 | −70 | −55 | 10 | 5 | | |
| 117E:C-CA-CB-HB2 | 65 | 45 | 50 | 20 | 15 | | |
| 117E:C-CA-N-HN | 75 | 125 | 135 | 50 | 60 | | |
| 117E:CA-CB-CG-CD | −165 | 165 | 95 | 150 | 80 | | |
| 117E:CA-CB-CG-HG1 | −45 | −70 | −140 | 25 | 95 | | |
| 117E:CA-CB-CG-HG2 | 65 | 45 | −25 | 20 | 90 | | |
| 117E:CB-CA-N-HN | −45 | −5 | 5 | 40 | 50 | | |
| 117E:HA-CA-CB-CG | 65 | 55 | 60 | 10 | 5 | | |
| 117E:HA-CA-CB-HB1 | −175 | 180 | −170 | 175 | 5 | | |
| 117E:HA-CA-CB-HB2 | −50 | −60 | −65 | 10 | 15 | | |
| 117E:HA-CA-N-HN | −160 | −125 | −110 | 35 | 50 | | |
| 117E:HB1-CB-CG-CD | 65 | 45 | −30 | 20 | 95 | | |
| 117E:HB1-CB-CG-HG1 | −175 | 170 | 90 | 165 | 85 | | |
| 117E:HB1-CB-CG-HG2 | −65 | −75 | −155 | 10 | 90 | | |
| 117E:HB2-CB-CG-CD | −50 | −80 | −145 | 30 | 95 | | |
| 117E:HB2-CB-CG-HG1 | 70 | 50 | −25 | 20 | 95 | | |
| 117E:HB2-CB-CG-HG2 | 180 | 160 | 90 | 20 | 90 | | |
| 117E:N-CA-CB-CG | −60 | −70 | −60 | 10 | 0 | | |
| 117E:N-CA-CB-HB1 | 65 | 55 | 70 | 10 | 5 | | |

TABLE 7-continued

Dihedral angles in the centroid structures of the linear, cyclic, and native ensembles.

| Residue:Dihedral | cyclic | native | biased | cyclic-native | cyclic-biased | avg cyclic-native | avg cyclic-biased |
|---|---|---|---|---|---|---|---|
| 117E:N-CA-CB-HB2 | −175 | 175 | 180 | 170 | 175 | | |
| 117E:O-C-CA-CB | −65 | −85 | −70 | 20 | 5 | | |
| 117E:O-C-CA-HA | 45 | 30 | 45 | 15 | 0 | | |
| 117E:O-C-CA-N | 175 | 150 | 165 | 25 | 10 | | |
| 117E:OE1-CD-CG-CB | −75 | 10 | 125 | 85 | 20 | | |
| 117E:OE1-CD-CG-HG1 | 165 | −115 | 5 | 100 | 160 | | |
| 117E:OE1-CD-CG-HG2 | 55 | 130 | −115 | 75 | 170 | | |
| 117E:OE2-CD-CG-CB | 100 | −175 | −55 | 95 | 155 | | |
| 117E:OE2-CD-CG-HG1 | −15 | 55 | −175 | 70 | 160 | | |
| 117E:OE2-CD-CG-HG2 | −125 | −60 | 70 | 65 | 15 | | |
| 118Q:C-CA-CB-CG | −175 | 175 | 180 | 170 | 175 | 76.5 | 54.7 |
| 118Q:C-CA-CB-HB1 | −55 | −65 | −60 | 10 | 5 | | |
| 118Q:C-CA-CB-HB2 | 60 | 50 | 60 | 10 | 0 | | |
| 118Q:C-CA-N-HN | 85 | 130 | 115 | 45 | 30 | | |
| 118Q:CA-CB-CG-CD | −35 | −65 | −65 | 30 | 30 | | |
| 118Q:CA-CB-CG-HG1 | 85 | 60 | 50 | 25 | 35 | | |
| 118Q:CA-CB-CG-HG2 | −150 | 180 | 170 | 150 | 140 | | |
| 118Q:CB-CA-N-HN | −45 | 5 | −15 | 50 | 30 | | |
| 118Q:CG-CD-NE2-1HE2 | −175 | −25 | 35 | 150 | 30 | | |
| 118Q:CG-CD-NE2-2HE2 | 20 | 180 | −170 | 160 | 10 | | |
| 118Q:HA-CA-CB-CG | 80 | 60 | 65 | 20 | 15 | | |
| 118Q:HA-CA-CB-HB1 | −160 | −175 | −175 | 15 | 15 | | |
| 118Q:HA-CA-CB-HB2 | −45 | −65 | −60 | 20 | 15 | | |
| 118Q:HA-CA-N-HN | −170 | −110 | −130 | 60 | 40 | | |
| 118Q:HB1-CB-CG-CD | −160 | 175 | 170 | 155 | 150 | | |
| 118Q:HB1-CB-CG-HG1 | −40 | −60 | −75 | 20 | 35 | | |
| 118Q:HB1-CB-CG-HG2 | 85 | 60 | 45 | 25 | 40 | | |
| 118Q:HB2-CB-CG-CD | 90 | 60 | 60 | 30 | 30 | | |
| 118Q:HB2-CB-CG-HG1 | −150 | −175 | 170 | 25 | 140 | | |
| 118Q:HB2-CB-CG-HG2 | −25 | −55 | −65 | 30 | 40 | | |
| 118Q:N-CA-CB-CG | −45 | −60 | −50 | 15 | 5 | | |
| 118Q:N-CA-CB-HB1 | 75 | 65 | 70 | 10 | 5 | | |
| 118Q:N-CA-CB-HB2 | −170 | 175 | −175 | 165 | 5 | | |
| 118Q:NE2-CD-CG-CB | −55 | 160 | −110 | 35 | 55 | | |
| 118Q:NE2-CD-CG-HG1 | 180 | 35 | 135 | 145 | 45 | | |
| 118Q:NE2-CD-CG-HG2 | 65 | −85 | 15 | 150 | 50 | | |
| 118Q:O-C-CA-CB | −35 | −100 | −90 | 65 | 55 | | |
| 118Q:O-C-CA-HA | 85 | 15 | 20 | 70 | 65 | | |
| 118Q:O-C-CA-N | −165 | 135 | 140 | 120 | 125 | | |
| 118Q:OE1-CD-CG-CB | 130 | −15 | 85 | 145 | 45 | | |
| 118Q:OE1-CD-CG-HG1 | 5 | −140 | −30 | 145 | 35 | | |
| 118Q:OE1-CD-CG-HG2 | −110 | 100 | −155 | 30 | 45 | | |
| 118Q:OE1-CD-NE2-1HE2 | 0 | 145 | −160 | 145 | 160 | | |
| 118Q:OE1-CD-NE2-2HE2 | −165 | −5 | −5 | 160 | 160 | | |

FIG. 6 again shows TTEQ (SEQ ID NO:1) in the native centroid, biased centroid, and cyclic peptide centroids for CGGTTEQGG (SEQ ID NO: 2) and CGTTEQG (SEQ ID NO: 3), now using a surface area representation for residues TTEQ (SEQ ID NO: 1). The surface area profile, which would be presented to an antibody, is different between the centroid conformations. Conformations have been shown separately, but all have been aligned. Comparing the centroid configurations of the native, biased, and cyclic ensembles, the exposed surface area of E117 and as well T115, monotonically increase consistently with the SASA plotted in FIGS. 4B and 4C. Thus, antibodies raised to this region in a cyclic ensemble of TDP-43 will be unlikely to bind (e.g. equally or with similar selectivity) TTEQ (SEQ ID NO: 1) in native TDP-43.

FIG. 6E shows an example of interactions that are present in the native ensemble of RRM1 of TDP-43, which bury surface area of the side chain of E117, but which are disrupted upon biasing the protein to be partially unfolded. In the native ensemble, E117 forms a salt-bridge with Lysine 137 (K137), which constrains the side chains of each residue, and reduces the exposed surface area of E117 in the native ensemble. In the biased ensemble however (FIG. 6E, right panel), the salt-bridge is broken, exposing the side chain of E117. Other interactions within the protein are also sufficiently weakened that the exposure of T115 also increases, as plotted in FIGS. 4B and C.

Example 2

Clustering by RMSD for TTE in the Cyclic Compounds CGTTEG (SEQ ID NO: 28) and CGTTEGG (SEQ ID NO: 29)

A similar set of experiments were performed for TTE in the cyclic compounds CGTTEG (SEQ ID NO: 28) and CGTTEGG (SEQ ID NO: 29).

RMSD was analysed as in Example 1 for TTE cyclic compounds. Clustering plots by root mean squared deviation (RMSD) are shown in FIG. 8. The axes correspond to the RMSD of TTE relative to TTE in the centroid structure of the cyclic peptide ensemble cyclo (CGTTEG) (SEQ ID NO: 28) (panel A) or cyclo (CGTTEGG) (SEQ ID NO: 29) (panel B), the RMSD of TTE to TTE in the centroid structure of the native structural ensemble (equilibration starting from PDB ID 4IUF) and the RMSD of TTE to TTE in the centroid structure of the non-native biased ensemble (the biased ensemble with the points overlapping with the native ensemble removed). Each point corresponds to a given conformation taken from either the cyclic peptide equilibrium ensemble (circles as noted in the legend), the non-native biased equilibrium ensemble (+ symbols as noted in the legend), or the native structure equilibrium ensemble starting from PDB ID 4IUF (inverted triangles as noted in the legend).

Figure 9A:
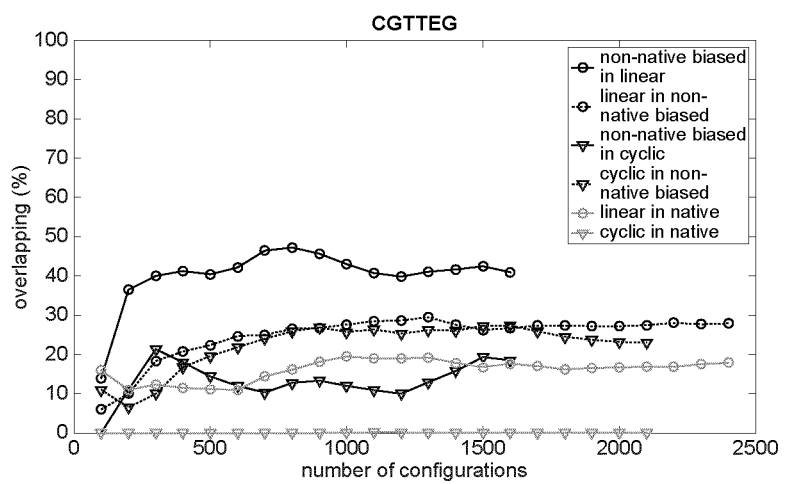
Figure 9B:
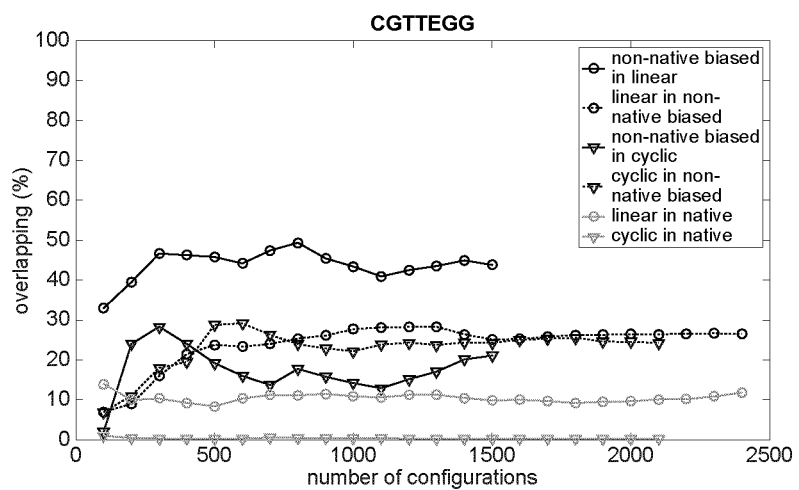

FIG. 9 shows the overlap of percentages between the different ensembles, as a function of the number of configurations sampled, to show convergence. Cyclic ensemble corresponds to the sequence cyclo(CGTTEG) (SEQ ID NO: 28) (Panel A) or cyclo(CGTTEGG) (SEQ ID NO: 29) (Panel B). Analogous to FIG. 7, the percent overlap for each pair of ensembles shows the percent overlap of a particular ensemble with 90% of the comparator structure ensemble, as described in the text in Example 2. The numeric overlapping percentages are given in Table 8A below. The overlap of the cyclic ensemble with the native ensemble is zero within the numerical accuracy of the simulations; low similarity to the native structure is again a desirable feature for a cyclic peptide scaffold.

TABLE 8A

| cyclic sequence | cyclic in non-native biased | non-native biased in cyclic | cyclic in native | ratio of (cyclic in biased + biased in cyclic)/ (2*(cyclic in native)) |
|---|---|---|---|---|
| CGTTEG | 22% | 17% | 0% | inf |
| CGTTEGG | 25% | 21% | 0% | inf |
| CGGTTEGG | 37% | 20% | 5% | 5.7 |
| CGGGTTEGG | 10% | 22% | 2% | 8.0 |
| CGGTTEGGG | 25% | 27% | 3% | 8.7 |
| CGGGTTEGGG | 20% | 35% | 5% | 5.5 |
| CGGGGTTEGGG | 20% | 42% | 10% | 3.1 |
| CGGGGTTEGGGG | 45% | 52% | 16% | 3.0 |

Table 8A shows the overlapping percentage of the RMSD clustering between the cyclic in native, cyclic in non-native biased, and non-native biased in cyclic forms of the cyclopeptides as presented in FIG. 9 panels for the scaffolds cyclo(CGTTEG) (SEQ ID NO: 28) and cyclo(CGTTEGG) (SEQ ID NO: 29). The last column gives the ratio defined by the mean of Columns 2 and 3 divided by column 4 column 4 (provided in the right most column). The two scaffolds cyclo(CGTTEG) (SEQ ID NO: 28) and cyclo(CGTTEGG) (SEQ ID NO: 29) show the largest discrimination between the non-native biased ensemble and the native ensemble, having a ratio of overlap equal to infinity (the cyclic ensemble has no overlap with the native ensemble).

Additional computational simulations were performed to measure the similarity between various ensembles by measuring the Jensen-Shannon distance [Lindorff-Larsen K, Ferkinghoff-Borg J (2009) Similarity Measures for Protein Ensembles. PLOS ONE 4(1): e4203] between the cyclic-native, cyclic-biased, and cyclic-(unfolded monomer) ensemble pairs. Applying weights to these measurement criteria along with uncertainties in the weights allows the use of multiple criteria decision-making analysis [Hwang C L, Yoon K. Multiple attribute decision making: methods and applications a state-of-the-art survey. vol. 186. Springer Science & Business Media; (2012)] to select viable candidates that differentiate misfolded/biased TDP-43 from native TDP-43 as well as pre-folded TDP-43 monomer (i.e. transient unfolded TDP-43 monomer). A sequence of length 77 residues in RRM1 was used to model an unfolded monomer of the RRM1 domain, starting from amino acid 103 and ending at amino acid 179. The analysis was performed and used to assess the similarity of TTE and TTEQ (SED ID NO:1) epitopes in the context of biased TDP-43 RRM1 domain and various cyclic peptides comprising said epitopes, in the context of different scaffolds consisting of variable numbers of glycine spacers. The ensemble overlap was also measured, for the same simulation data, in terms of the number of standard deviations between two separated Gaussian distributions. All of the ensemble overlap data is shown in Table 8B.

TABLE 8B

| Sequence | cyclic-native-JSD | 1-(cyclic-biased-JSD) | cyclic-monomer-JSD | cyclic-native-d | dmax-cyclic-biased-d | (cyclic-monomer-d |
|---|---|---|---|---|---|---|
| CGTTEG | 1.000 | 0.072 | 0.984 | 7.744 | 3.496 | 5.594 |
| CGTTEGG | 1.000 | 0.116 | 0.961 | 7.704 | 3.944 | 4.822 |
| CGTTEQG | 0.998 | 0.100 | 0.970 | 7.658 | 3.825 | 5.093 |
| CGGTTEGG | 1.000 | 0.080 | 0.989 | 7.778 | 3.533 | 5.810 |
| CGTTEQGG | 0.994 | 0.126 | 0.969 | 7.129 | 4.049 | 5.088 |
| CGGTTEGGG | 0.998 | 0.148 | 0.903 | 7.146 | 4.209 | 3.969 |
| CGGTTEQGG | 0.993 | 0.106 | 0.958 | 6.256 | 3.888 | 4.806 |
| CGGGTTEGG | 0.999 | 0.094 | 0.881 | 7.414 | 3.778 | 3.784 |
| CGGGTTEGGG | 0.980 | 0.157 | 0.868 | 5.420 | 4.247 | 3.677 |

TABLE 8B-continued

| Sequence | cyclic-native-JSD | 1-(cyclic-biased-JSD) | cyclic-monomer-JSD | cyclic-native-d | dmax-cyclic-biased-d) | (cyclic-monomer-d |
|---|---|---|---|---|---|---|
| CGGTTEQGGG | 0.971 | 0.162 | 0.857 | 5.144 | 4.295 | 3.639 |
| CGGGTTEQGG | 0.980 | 0.128 | 0.928 | 5.574 | 4.043 | 4.314 |
| CGGGGTTEGGG | 0.979 | 0.172 | 0.815 | 5.373 | 4.368 | 3.327 |
| CGGGGTTEGGGG | 0.889 | 0.321 | 0.846 | 3.933 | 5.064 | 3.505 |

Cyclic peptides which overlapped significantly with TTE and TTEQ (SED ID NO:1) epitopes in the context of biased TDP-43 RRM1 domain as measured by the JSD data in Table 8B, but had small overlap with either natively folded TDP-43 or transient unfolded TDP-43, included scaffolds (linker) with up to 9 amino acids (SEQ ID NO: 35) and are given in Table 8C.

TABLE 8C

| Cyclic peptide | SEQ ID NO |
|---|---|
| CGTTEG | SEQ ID NO: 28 |
| CGTTEGG | SEQ ID NO: 29 |
| CGTTEQG | SEQ ID NO: 3 |
| CGGTTEGG | SEQ ID NO: 30 |
| CGTTEQGG | SEQ ID NO: 23 |
| CGGTTEGGG | SEQ ID NO: 32 |
| CGGTTEQGG | SEQ ID NO: 2 |
| CGGGTTEGG | SEQ ID NO: 31 |
| CGGGTTEGGG | SEQ ID NO: 33 |
| CGGTTEQGGG | SEQ ID NO: 22 |
| CGGGTTEQGG | SEQ ID NO: 42 |
| CGGGGTTEGGG | SEQ ID NO: 34 |
| CGGGGTTEGGGG | SEQ ID NO: 35 |

Example 3

Cyclic Compound Construction Comprising a Conformationally Constrained Epitope

Peptides comprising TTEQ (SEQ ID NO: 1) or TTE such as cyclo (CGTTEQG) (SEQ ID NO:3) or cyclo(CGTTEG) (SEQ ID NO: 28) can be cyclized head to tail.

A native ensemble comprising TTEQ (SEQ ID NO:1) or TTE and a linker, preferably comprising 2, 3, or 4 amino acids and/or PEG units, can be synthesized using known methods such as Fmoc based solid phase peptide synthesis alone or in combination with other methods. PEG molecules can be coupled to amine groups at the N terminus for example using coupling chemistries described in Hamley 2014 [7] and Roberts et al. 2012 [8], each incorporated herein by reference. The native ensemble compound may be cyclized by covalently bonding 1) the amino terminus and the carboxy terminus of the peptide+linker to form a peptide bond (e.g. cyclizing the backbone), 2) the amino or carboxy terminus with a side chain in the peptide+linker or 3) two side chains in the peptide+linker.

The bonds in the cyclic compound may be all regular peptide bonds (homodetic cyclic peptide) or include other types of bonds such as ester, ether, amide or disulfide linkages (heterodetic cyclic peptide).

Peptides may be cyclized by oxidation of thiol- or mercaptan-containing residues at the N-terminus or C-terminus, or internal to the peptide, including for example cysteine and homocysteine. For example two cysteine residues flanking the peptide may be oxidized to form a disulphide bond. Oxidative reagents that may be employed include, for example, oxygen (air), dimethyl sulphoxide, oxidized glutathione, cystine, copper (II) chloride, potassium ferricyanide, thallium (III) trifluro acetate or other oxidative reagents such as may be known to those of skill in the art and used with such methods as are known to those of skill in the art.

Methods and compositions related to cyclic peptide synthesis are described in US Patent Publication 2009/0215172. US Patent publication 2010/0240865, US Patent Publication 2010/0137559 and U.S. Pat. No. 7,569,541 describe various methods for cyclization. Other examples are described in PCT Publication WO01/92466, and Andreu et al., 1994. Methods in Molecular Biology 35:91-169.

More specifically, a cyclic peptide comprising the TTEQ (SEQ ID NO: 1) epitope, TEQ epitope or TTE epitope can be constructed by adding a linker comprising a spacer with cysteine residues flanking and/or inserted in the spacer. The peptide can be structured into a cyclic conformation by creating a disulfide linkage between the non-native cysteines residues added to the N- and C-termini of the peptide. It can also be synthesized into a cyclic compound by forming a peptide bond between the N- and C-termini amino acids (e.g. head to tail cyclization).

Peptide synthesis is performed by CPC Scientific Inc. (Sunnyvale Calif., USA) following standard manufacturing procedures. The structure of the cyclic peptide was designed to mimic the conformation and orientation of the amino acid backbone and side chains of TTEQ (SEQ ID NO: 1) in misfolded TDP-43 polypeptide.

Cyclo (SEQ ID NO: 3)
( )

Cyclo (CGTTEQG) (SEQ ID NO: 3) and cyclo (CGGTTEQGG) (SEQ ID NO: 2) may be synthesized using the following method (CPC Scientific Inc, Sunnyvale Calif.). The protected native ensemble was synthesized by standard conventional Fmoc-based solid-phase peptide synthesis on 2-chlorotrityl chloride resin, followed by cleavage from the resin with 30% HFIP/DCM. Protected native ensemble was cyclized to the corresponding protected cyclic peptide by using EDC. HCl/HOBt/DIEA in DMF at low concentration. The protected cyclic peptide was deprotected by TFA to give crude cyclic peptide and the crude peptide was purified by RP HPLC to give pure cyclic peptide after lyophilize.

Cyclo (CGTTEQG) (SEQ ID NO: 3) and cyclo (CGGTTEQGG) (SEQ ID NO: 2) can be prepared by amide condensation of the linear peptide CGTTEQG (SEQ ID NO: 3) or CGGTTEQGG (SEQ ID NO: 2) respectively.

Cyclo (C-PEG2-TTEQG) (SEQ ID NO: 24) and cyclo (C-PEG2-TTEQGG) (SEQ ID NO: 25) can be prepared by amide condensation of the linear compound C-PEG2-TTEQG (SEQ ID NO: 24) or C-PEG2-TTEQGG (SEQ ID NO: 25) respectively.

Cyclo (CGTTEQ-PEG2) (SEQ ID NO: 26) and cyclo (CGGTTEQ-PEG2) (SEQ ID NO: 27) can be prepared by amide condensation of the linear compound CGTTEQ-PEG2 (SEQ ID NO: 26) or CGGTTEQ-PEG2 (SEQ ID NO: 27) respectively.

Linear (CGTTEQG) (SEQ ID NO: 3) or Linear (CGGTTEQGG) (SEQ ID NO: 2) may be prepared (CPC Scientific Inc, Sunnyvale Calif.). The protected native ensemble was synthesized by standard conventional Fmoc-based solid-phase peptide synthesis on Fmoc-Gly-Wang resin, then the protected peptide was cleaved by TFA to give crudepeptide and the crude peptide was purified by RP HPLC to give pure peptide after lyophilize, and which was used to conjugate BSA.

Similarly, cyclo (CGTTEG) (SEQ ID NO: 28) and Cyclo (CGTTEGG) (SEQ ID NO: 29) can be prepared by amide condensation of the linear peptide CGTTEG (SEQ ID NO: 28) or CGTTEGG(SEQ ID NO: 29) respectively.

Cyclo(C-PEG2-TTEG) (SEQ ID NO: 36) and Cyclo(C-PEG2-TTEGG) (SEQ ID NO: 37) can be prepared by amide condensation of the linear compound C-PEG2-TTEG (SEQ ID NO: 36) or C-PEG2-TTEGG (SEQ ID NO: 37) respectively.

Cyclo(CGTTE-PEG2) (SEQ ID NO: 38) and Cyclo (CGGTTE-PEG2) (SEQ ID NO: 39) can be prepared by amide condensation of the linear compound CGTTE-PEG2 (SEQ ID NO: 38) or CGGTTE-PEG2 (SEQ ID NO: 39) respectively.

Cyclic and Linear (CGTTEG) (SEQ ID NO: 28) or Linear (CGGTTEGG) (SEQ ID NO: 30) peptides may be prepared (CPC Scientific Inc, Sunnyvale Calif.). The protected was synthesized by standard conventional Fmoc-based solid-phase peptide synthesis on Fmoc-Gly-Wang resin, then the protected peptide was cleaved by TFA to give crudepeptide and the crude peptide was purified by RP HPLC to give pure peptide after lyophilize, and which was used to conjugate BSA.

Immunogen Construction

The cyclic compounds cyclo (CGTTEQG) (SEQ ID NO: 3), cyclo (CGGTTEQGG) (SEQ ID NO: 2), cyclo (CGTTEG) (SEQ ID NO: 28) and cyclo (CGTTEGG) (SEQ ID NO: 29) are synthesized as described above and then conjugated to KLH (for immunizing) or BSA (for screening) (CPC Scientific Inc, Sunnyvale Calif.). BSA or KLH is re-activated by SMCC in PBS buffer, then a solution of the pure peptide in PBS buffer is added to the conjugation mixture, the conjugation mixture is stirred at room temperature for 2 h. Then the conjugation mixture is lyophilized after dialysis to give the conjugation product.

Peptides can also be conjugated to KLH (for immunizing) and BSA (for screening) using a trifluoroacetate counter ion protocol. Peptides are desalted and checked by MS and HPLC to confirm at least 95% pure.

Example 4

Antibody Generation and Selection

A conformationally constrained compound optionally a cyclic compound such as a cyclic peptide comprising TTEQ (SEQ ID NO: 1) or TTE such as cyclo (CGTTEQG) (SEQ ID NO: 3), cyclo(CGGTTEQGG) (SEQ ID NO: 2), cyclo (CGTTEG) (SEQ ID NO: 28) or cyclo (CGTTEGG) (SEQ ID NO: 29) is linked to Keyhole Limpet Hemocyanin (KLH). The linked peptide or peptides are sent to Immunoprecise Antibodies LTD (Victoria BC, Canada) for mouse monoclonal antibody production, following protocols approved by the Canadian Council on Animal Care.

Immunization

Briefly, female BALB/c mice (Charles River Laboratories, Quebec) are immunized. A series of subcutaneous aqueous injections containing antigen but no adjuvant are given over a period of 19 days. Mice are immunized with 100 μg per mouse per injection of a 0.5 mg/mL solution in sterile saline of cyclic peptide-KLH. All mice are euthanized on Day 19 and lymphocytes are harvested for hybridoma cell line generation.

Fusion/Hybridoma Development

Lymphocytes are isolated and fused with murine SP2/0 myeloma cells in the presence of poly-ethylene glycol (PEG 1500). Fused cells are cultured using HAT selection. This method uses a semi-solid methylcellulose-based HAT selective medium to combine the hybridoma selection and cloning into one step. Single cell-derived hybridomas grow to form monoclonal colonies on the semi-solid media. Approximately 10 days after the fusion event, resulting hybridoma clones are transferred to 96-well tissue culture plates and grown in HT containing medium until mid-log growth is reached (approximately 5 days).

Hybridoma Analysis (Screening)

Tissue culture supernatants from the hybridomas can be tested by indirect ELISA on screening antigen (cyclic or linear peptide-BSA) and probed for both IgG and IgM antibodies using a Goat anti-IgG/IgM(H&L)-HRP secondary and developed with TMB substrate.

Clones >0.2 OD in this assay are taken to the next round of testing. Positive cultures are retested on screening antigen to confirm secretion and on an irrelevant antigen (Human Transferrin). Clones of interest are isotyped by antibody trapping ELISA to determine if they are IgG or IgM isotype and can be tested by indirect ELISA on other cyclic peptide-BSA conjugates as well as native-BSA conjugates to evaluate cross-reactivity.

Positive IgG-secreting clones are subjected to large-scale production.

Direct Binding Assays

Binding of clones to linear and cyclic peptides (conjugated to BSA) can be examined by surface plasmon resonance using a Biacore™ 3000 instrument (GE Healthcare).

Binding analysis is carried out using a high density (at least 1000 response units (RU)) of antigen immobilized on flow cells. Dilutions of a selected clone are sequentially injected over the surface to assess binding.

For affinity kinetics and specificity analysis, a conformational peptide comprising TTEQ (SEQ ID NO: 1) or TTE and BSA, for example a cyclic peptide having the sequence of SEQ ID NO:2, 3 28 or 29 conjugated to BSA via amine conjugation, are immobilized at low densities (50-100 RU) on adjacent flow cells. Serial 2-fold dilutions of a selected clone (4.7 nM to 75 nM) are then sequentially injected over the surfaces at 60 μl/minute for 3 minutes, followed by a dissociation phase. Following a double-reference subtraction, the sensorgrams are fitted to a Langmuir 1:1 binding model. Up to three separate analyses are performed on 3 consecutive days using the same sensorchip and the same conditions.

Binding analysis can be carried out also using Molecular Affinity Screening System (MASS-1) (Sierra Sensors GmbH, Hamburg, Germany). MASS-1 is a Surface Plasmon Resonance (SPR) Imaging analytical biosensor that employs high intensity laser light and high speed optical scanning to monitor binding interactions in real time. The peptide-BSA conjugates are covalently immobilized on separate flow cells of a High Amine Capacity (HAC) sensor chip, using standard amine-coupling chemistry, and unreacted sites blocked. Adjacent flow cells are similarly immobilized with BSA as a reference control surface.

Tissue culture supernatants are screened for the presence of antibody binding against their cognate cyclic peptide. Each sample is diluted and injected in duplicate over the immobilized peptide and BSA reference surfaces for 2 minutes, followed by injection of running buffer only for a 5-min dissociation phase. After every analytical cycle, the sensor chip surfaces are regenerated. Sensorgrams are double-referenced by subtracting out binding from the BSA reference surfaces and blank running buffer injections, and binding response report points measured at 20 seconds before the end of the injection in a 20 second window of data.

Isotyping

The hybridoma antibodies are isotyped using antibody trap experiments. Trap plates are coated with 1:10,000 Goat anti-mouse IgG/IgM(H&L) antibody at 100 uL/well carbonate coating buffer pH9.6 overnight at 4 C. Primary antibody (hybridoma supernatants) is added at 100 ug/mL. Secondary Antibody is added at 1:5,000. Goat anti-mouse IgGγ-HRP or 1:10,000 Goat anti-mouse IgMμ-HRP is added at 100 uL/well in PBS-Tween for 1 hour at 37 C with shaking. All washing steps are performed for 30 mins with PBS-Tween. The substrate TMB is added at 50 uL/well, developed in the dark and stopped with equal volume 1M HCl.

Example 5

Monoclonal antibodies were made using the methods in Example 4. Specifically cyclo(CGGTTEQGG) (SEQ ID NO: 2) conjugated to KLH or cyclo(CGTTEQG) (SEQ ID NO:3) conjugated to KLH via the cysteine residues were injected into mice and monoclonal antibodies were generated.

Antibody-containing hybridoma tissue culture supernatants were typed for immunoglobulin type and screened against negative control peptide and BSA. IgG producing clones that did not bind the negative control peptide or BSA were tested by ELISA for binding to the immunizing cyclic peptides, to corresponding linear peptides and related cyclic peptides cyclo(CGGTTEGGG) (SEQ ID NO: 32), cyclo (CGTTEGG) (SEQ ID NO: 29) as described below.

ELISA Conditions:

ELISA plates were coated with 0.1 μg/well with peptide cyclo(CGGTTEQGG) (SEQ ID NO: 2) or cyclo (CGTTEQG) (SEQ ID NO: 3) or the linear versions thereof at 100 μL/well in carbonate Coating Buffer (pH 9.6) overnight at 4 C. In other assays, cyclo(CGGTTEGGG) (SEQ ID NO: 32) or cyclo (CGTTEGG) (SEQ ID NO: 29) were also used to coat the ELISA plates.

The plates were blocked with 3% skim milk powder in PBS for 1 hour at room temperature. The primary antibody, hybridoma tissue culture supernatant neat at 100 uL/well, was incubated for 1 hour at 37 C with shaking. The secondary antibody, goat anti-mouse IgGγ-HRP at a 1:10,000 dilution was added at 100 uL/well in PBS-Tween and incubated for 1 hour at 37 C with shaking. All washing steps were performed for 30 mins with PBS-Tween. TMB Substrate was added at 50 uL/well, developed in the dark and stopped with equal volume 1M HCl. The development time was 1-2 min and the plate was read at 450 nm.

The ELISA results are presented in Table 9 A and B for which shows the binding affinity of monoclonal antibodies generated against the immunizing peptide versus the corresponding linear peptide. As shown therein, IgG antibodies were produced that showed preferential binding to the immunizing cyclic peptides compared to the linear peptide.

TABLE 9A

Affinity for cyclo(CGGTTEQGG) (SEQ ID NO: 2) compared to linear peptide

|  | 2H10 | 3H5 | 6C5 | 9B10 | 9C5 | 9G4 | 11F3 |
|---|---|---|---|---|---|---|---|
| Cyclo (CGGTTEQGG) SEQ ID NO: 2 | 2.516 | 2.835 | 1.101 | 1.877 | 2.286 | 1.896 | 1.105 |
| Linear CGGTTEQGG SEQ ID NO: 2 | 0.104 | 0.068 | 0.191 | 0.074 | 0.115 | 0.083 | 0.071 |

TABLE 9B

Binding affinity for cyclo (CGTTEQG) (SEQ ID NO: 3) compared to linear peptide

|  | 1G10 | 2G4 | 5B11 | 3C11 | 5D3 | 4B3 | 4D3 | 4E2 | 4G5 | 11D5 |
|---|---|---|---|---|---|---|---|---|---|---|
| Cyclo (CGTTEQG) SEQ ID NO: 3 | 2.186 | 1.907 | 1.97 | 1.567 | 2.222 | 2.296 | 1.712 | 1.743 | 1.71 | 2.962 |

TABLE 9B-continued

Binding affinity for cyclo (CGTTEQG) (SEQ ID NO: 3) compared to linear peptide

| | 1G10 | 2G4 | 5B11 | 3C11 | 5D3 | 4B3 | 4D3 | 4E2 | 4G5 | 11D5 |
|---|---|---|---|---|---|---|---|---|---|---|
| Linear CGTTEQG SEQ ID NO: 3 | 0.07 | 0.08 | 0.122 | 0.109 | 0.064 | 0.073 | 0.07 | 0.084 | 0.064 | 0.05 |

In addition antibodies were tested for binding to related cyclic peptides cyclo(CGGTTEGGG) (SEQ ID NO: 32) and cyclo (CGTTEGG) (SEQ ID NO: 29) comprising the TTE epitope. Fifteen of 17 antibodies, had greater affinity for a related cyclic peptide compared to the linear peptide corresponding to the immunogen and 14 of the 17 antibodies tested had about a 2 fold or greater selectivity for a related cyclic peptide compared to the linear peptide corresponding to the immunogen.

Example 6

Misfolded TDP-43 Characterization

Antibodies will be tested for their ability to bind native TDP-43 polypeptide as well as misfolded TDP-43 polypeptide using surface plasmon resonance and immunohistochemistry.

Surface Plasmon Resonance (Biacore) of Biological Samples.

Homogenization: Human and mouse neurological tissue samples are weighed and subsequently submersed in a volume of fresh, ice cold TBS (supplemented with 5 mM EGTA, 5 mM EDTA, (both from Sigma) and EDTA-free protease inhibitor cocktail from Roche Diagnostics, Laval QC, Canada) such that the final concentration of tissue is 20% (w/v). Tissue is homogenized in this buffer using a mechanical probe homogenizer (3×30 sec pulses with 30 sec pauses in between, all performed on ice). TBS homogenized samples are then subjected to ultracentrifugation (70,000×g for 90 min). Supernatants are collected, aliquoted and stored at −80° C. The protein concentration of TBS homogenates is determined using a BCA protein assay (Pierce Biotechnology Inc, Rockford Ill., USA).

Surface Plasmon Resonance Analysis: CSF samples and neurological tissue samples from ALS patients and/or FTD patients and age-matched controls are analyzed. Test antibodies and an IgG1 isotype control are directly immobilized at high densities (10,000 RU) on 2 separate flow cells of a sensor chip. Using a Biacore 3000, diluted neurological tissue samples, homogenized in TBS are injected sequentially over the surfaces for 300 seconds, followed by 150 seconds of dissociation in buffer and surface regeneration. Binding responses are double-referenced by subtraction of IgG1 reference surface binding and normalized with assay buffer, and the different groups of samples compared.

Example 7

Human embryonic kidney cells (HEK293FT) were transiently transfected with a modified form of TDP-43 with an HA-tag and lacking a nuclear localization signal (TDP-43$^{\Delta NLS}$). This form of the protein accumulates in the cytoplasm and forms misfolded aggregates. Empty vector was used as a negative control.

The cells were stained overnight at 4° C. with 1 µg/ml polyclonal rabbit antibody against the HA tag (to detect misfolded cytoplasmic TDP-43) or with 10 µg/ml of test antibody. Bound antibodies were then detected by staining for 1 hour at room temperature with fluorescently-labeled anti-rabbit (red Alexa Fluor 647) or anti-mouse (green Alexa Fluor 488) secondary antibody. Nuclear DNA was stained with Hoeschst 33342 dye (blue). Micrographs were acquired on a confocal Leica SP8 microscope in a Z-stack fashion with 0.3 µm steps. Included images represent a Z-plane projection of the entire cell thickness. Z-stacked images (20-30 steps) of single fluorescence channels and merged signals were captured.

The results are presented in FIG. 10. Panel A shows Hoechst 33342 dye stained cells and reveals the cell nuclei. FIG. 10B shows cells stained for the HA tagged recombinant TDP-43$^{\Delta NLS}$. Only the recombinant protein is detected. As expected the exogenously expressed TDP-43 lacking a NLS was found in the cytoplasm and is present in misfolded aggregates. FIG. 10C shows results with a monoclonal antibody produced using cyclo(CGGTTEQGG) (SEQ ID NO: 2). Predominantly cytoplasmic staining is present suggesting the test antibody does not bind wild type nuclear TDP-43. FIG. 10D shows a merged image wherein there is substantial overlap (co-localization) between detection of HA tagged recombinant TDP-43$^{\Delta NLS}$ cytoplasmic aggregates and test antibody staining of TDP-43.

Example 8

Human spinal cord homogenates were prepared from control and sporadic ALS patients and were analysed by dot blot with selected antibodies.

Tissue from a human without ALS was used as the control and two different sporadic ALS tissue samples were assessed. One was a tissue sample obtained from a patient carrying the C9orf72 mutation and another was a tissue sample obtained from a patient with unknown mutation status.

PVDF membranes were dotted with 10 micrograms of homogenate in duplicate and the test antibodies and control antibody (mIgG1) were used at a 500 fold dilution of 2 microgram/microliter stock solution. Rabbit polyclonal TDP-43 antibody (ProteinTech, Rosemont Ill.) was used as a positive control.

As shown in FIG. 11A, the IgG1 negative control produced low background staining for all samples and as shown in FIG. 11B, the positive control antibody produced a robust positive signal for all tested samples.

Selective staining of sALS samples was seen using the test antibodies. Antibody 1 is clone IG10, antibody 2 is clone 2H10, antibody 3 is clone 11F3, antibody 4, is clone 3H5, antibody 5 is 4G5 and antibody 6 is clone 9C5. Antibody 6C5 also showed selective staining of sALS samples.

Example 9

Several of the antibodies positive for binding aggregated TDP-43 were sequenced. Immunoglobulin gene transcripts expressed by the hybridomas were amplified with sets of proprietary primers from cDNA generated from the hybridoma cells using standard RT-PCR protocol and sequenced using a standard dye-terminator capillary sequencing method (Immunoprecise, Victoria BC Canada).

Complementarity determining regions (CDRs) CDR1, CDR2 and CDR3 are highlighted are bolded and underlined, and were identified according to IgBLAST (available using ncbi tools (Ye et al., *Nucelic Acids Research* 2013, Vol. 41, Web Server Issue doi:10:1093|nar|gkt382). Using this tool a query is searched with BLAST against the IMGT or NCBI germline V gene database (the sequences in such databases have been pre-annotated for the FR/CDR boundaries). The top database sequence hit is used to map the pre-annotated FR/CDR boundary information to the query sequence. The BLAST search parameters are Expect cut-off, 20; word size 9; mismatch penalty, −1; Dust filtering, off.

TABLE 10

Antibody variable domain sequences

| Clone | Isotype | Consensus DNA Sequence | Translated Protein Sequence |
|---|---|---|---|
| 3H5 | Heavy-IgG1 SEQ ID NO: 45, 46 | CAGATCCAGTTGGTGCAGTCTGGACCTGAGCTGAAGAAGCCTGGAGAGA CAGTCAAGATCTCCTGCAAGGCTTCTGGTTATACCTTCACAGACTATTCA ATGCACTGGGTGAAACAGGCTCCAGGAAGGGTTTAAAGTGGATGGGCTG GATAAACACTGAGACTGGTGAGCCAACATATGCAGATGACTTCAAGGGA CGGTTTGCCTTCTCTTTGGAAACCTCTGCCAGCACTGCCTATTTGCAGATC AACAACTCAAAAATGAGGACACGGCTACATATTTCTGTGCTAGTCGACGA TGGTACCCGTACTACTTTGACTACTGGGGCCAAGGCACCACTCTCACAGT CTCCTCA | QIQLVQSGPELKKPGETVKI SCKASGYTFTDYSMHWVK QAPGKGLKWMGWINTET GEPTYADDPKGRFAFSLETS ASTAYLQINNLKNEDTATYF CASRRWYPYYFDYWGQG TTLTVSS |
| | Light-Lambda SEQ ID NO: 47, 48 | CAGGCTGTTGTGACTCAGGAATCTGCACTCACCACATCACCTGGTGAAAC AGTCACACTCACTTGTCGCTCAAGTACTGGGCTGTTACAACTAGTAACT ATGCCAACTGGGTCCAAGAAAAACCAGATC ATTTATTCACTGGTCTAATAGGTGGTCCCAACAACCGAGCTCCAGGTGTT CCTGCCAGATTCTCAGGCTCCCTGATTGGAGACAAGGCTGCCCTCACCAT CACAGGGGCACAGACTGAGGATGAGGCATATATTTCTGTGCTCTATGGT ACAGCAACCATTGGGTGTTCGGTGGAGGAACCAAACTGACTGTCCTA | QAVVTQESALTTSPGETVTL TCRSSTGAVTTSNYANWV QEKPDHLFTGLIGGPNNRA PGVPARFSGSLIGDKAALTIT GAQTEDEAIYFCALWYSNH WVFGGGTKLTVL |
| 6C5 | Heavy-IgG1 SEQ ID NO: 49, 50 | GAAGTGAAGCTGGTGGAGTCTGGGGGAGGCTTAGTGCAGCCTGGAGGG TCCCTGAAACTCTCCTGTGCAACCTCTGGATTCACTTTCAGTGACTATTAC ATGTATTGGGTTCGCCAGACTCCAGAGAGAGGTCTGGAGTGGGTCGCA CATTAGTAATGGTGGTGGTAGCACCTATTATCCAGACACTGTAAAGGGC CGATTCACCATCTCCAGAGACAATGCCAAGAACACCCTGTACCTGCAAAT GAGCCGTTGAAGTCTGAGGACACAGCCATGTATTACTGTGCAAGAGAGG GGGGTACCGCCTGGTTTGCTTACTGGGGCCAAGGGACTCTGGTCACTGT CTCTGCA | EVKLVESGGGLVQPGGSLK LSCATSGFTFSDYYMYWVR QTPEKRLEWVAYISNGGGS TYYPDTVKGRFTISRDNAKN TLYLQMSRLKSEDTAMYYC AREGGTAWFAYWGQGTL VTVSA |
| | Light-Kappa SEQ ID NO: 51, 52 | GATGTTTTGATGACCCAAACTCCACTCTCCCTGCCTGTCAGTCTTGGAGAT CAAGCCTCCATCTCTTGCAGATCTAGTCAGAGCATTGTACATAGTAATGG AAACACCTATTTAGAATGGTACCTGCGAAACCAGGCCAGTCTCCAAAGCT CCTGATCTACAAAGTTTCCAACCGATTTTCTGGGGTCCCAGACAGGTTCA GTGGCAGTGGATCAGGGACAGATTTCACACTCAAGATCAGCAGAGTGGA GGCTAGGATCTGGGAGTTTATTACTGCTTTCAAGGTTCACATGTTCCGTA CACGTTCGGAGGGGGGACCAAGCTGGAAATAAAA | DVLMTQTPLSLPVSLGDQA SISCRSSQSIVHSNGNTYLE WYLQKPGQSPKLLIYKVSN RFSGVPDRFSGSGSGTDFTL KISRVEAEDLGVYYCFQGSH VPYTFGGGTKLEIK |
| 9C5 | Heavy-IgG3 SEQ ID NO: 53, 54 | GAAGTGCAGCTGGTGGAGTCTGGGGGAGGCTTAGTGAAGCCTGGAGGG TCCCTGAAACTCTCCTGTGCAGCCTCTGGATTCACTTTCAGTGACTATTAC ATGTATTGGGTTCGCCAGACTCCAGAGAAAGAGGCTGGAGTGGGTCGAAC CATTAGTGATGGTGGTAGTTACACCTCCTATCCAGACAGTGTGAAGGGA CGATTCACCATCTCCAGAGACAATGCCAAGAACAACCTGTACCTGCAAAT GAGCAGTTGAGGTCTGAGGACACAGCCATGTATTACTGTGCAAGAGATT ACTATGGTAGTAGTAGCTACACCTCGGGCTTTGCTTACTGGGGCCAAGG GACTCTGGTCACTGTCTCTGCA | EVQLVESGGGLVKPGGSLK LSCAASGFTFSDYYMYWVR QTPEKRLEWVATISDGGSY TSYPDSVKGRFTISRDNAKN NLYLQMSSLRSEDTAMYC ARDYYGSSSYTSGFAYWG QGTLVTVSA |
| | Light-Kappa SEQ ID NO: 55, 56 | GATGTTTTGATGACCCAAACTCCACTCTCCCTGCCTGTCAGTCTTGGAGAT CAAGCCTCCATCTCTTGCAGATCTAGTCAGAGCATTGTACATAGTAATGG AAACACCTATTTAGAATGGTACCTGCGAAACCAGGCCAGTCTCCAAAGCT CCTGATCTACAAAGTTTCCAACCGATTTTCTGGGGTCCCAGACAGGTTCA GTGGCAGTGGATCAGGGACAGATTTCACACTCAAGATCAGCAGAGTGGA GGCTAGGATCTGGGAGTTTATTACTGCTTTCAAGGTTCACATGTTCCTGG GACGTTCGGTGGAGGCACCAAGCTGGAAATCAAA | DVLMTQTPLSLPVSLGDQA SISCRSSQSIVHSNGNTYLE WYLQKPGQSPKLLIYKVSN RFSGVPDRFSGSGSGTDFTL KISRVEAEDLGVYYCFQGSH VPGTFGGGTKLEIK |
| 11F3 | Heavy-IgG1 SEQ ID NO: 57, 58 | CAGATCCAGTTGGTGCAGTCTGGACCTGAGCTGAAGAAGCCTGGAGAGA CAGTCAAGATCTCCTGCAAGGCTTCTGGTTATACCTTCACAGACTATTCA ATGCACTGGGTGAAGCACTCTCCAGGAAGGGTTTAAAGTGGATGGGCTG GATAAACACTGAGACTGGTGAGCCAACATATGCAGATGACTTCAAGGGA CGGTTTGCCTTCTCTTTGGAAACCTCTGCCAGCACTGCCTATTTGCAGATC AACAACTCAAAAATGAGGACACGGCTACATATTTCTGTGCTAGAGGGTAT GGCAACTGGTTTGCTTACTG GGGCCAAGGGACTCTGGTCACTGTCTCTGCA | QIQLVQSGPELKKPGETVKI SCKASGYTFTDYSMHWVK HSPGKGLKWMGWINTET GEPTYADDPKGRFAFSLETS ASTAYLQINNKNEDTATYF CARGYGNWFAYWGQGTL VTVSA |
| | Light-Kappa SEQ ID NO: 59, 60 | CAAATTGTTCTCACCCAGTCTCCAGCAATCATGTCTGCATCTCTAGGGGAA CGGGTCACCATGACCTGCACTGCCAGCTCAAGTGTAAGTTCCAGTTACTT ACACTGGTACCAGCAGAAGCCAGGATCTCCCCCAAACTCTGGATTTATAG CACATCCAACCTGGCTTCTGGAGTCCCAGCTCGCTTCAGTGGCAGTGGGT CTGGGACCTCTTACTCTCTCACAATCAGCAGCATGGAGGCTGAAGATGCT | QIVLTQSPAIMSASLGERVT MTCTASSSVSSSYLHWYQ QKPGSSPKLWIYSTSNLASG VPARFSGSGSGTSYSLTISS MEAEDAATYYCHQYHRSP |

TABLE 10-continued

Antibody variable domain sequences

| Clone | Isotype | Consensus DNA Sequence | Translated Protein Sequence |
|---|---|---|---|
| | | GCCCTTATTACTGCCACCAGTATCATCGTTCCCCGCTCACGTTCGGTGCTG GGACCAAGCTGGAGCTGAAA | LTFGAGTKLELK |
| 2H10 | Heavy-IgG1 SEQ ID NOs: 61 62 VH1 | GAGGTGAAGCTGGTGGAATCTGGAGGAGGCTTGGTACAGCCTGGGGGT TCTCTGAGACTCTCCTGTGCAACTTCTGGGTTCACCTTCAGTGATTTCTAC ATAAACTGGGTCCGCCAGCCTCCAGGGAGAGACTGGAGTGGATTGCTAC AAGTAGGAGCAAAGCTCATGATTATACAACAGAGTACAGTGCATCTGTG AAGGGTCGGTTCATCGTCTCCAGAGACACTTCCCAAAGCATCCTCTACCTT CAGATGATGCCCTAAAACCTGAGGACACTGCCATTTATTACTGTGCAAGA GATACATGGTATGGTTCCTGGTTTGCTTACTGGGGCCAAGGGACTCTGG TCACTGTCTCTACA | EVKLVESGGGLVQPGGSLR LSCATSGFTFSDFYINWVR QPPGKRLEWIATSRSKAHD YTTEYSASVKGRFIVSRDTS QSILYLQMDALKPEDTAIYY CARDTWYGSWFAYWGQ GTLVTVST |
| | Light-Kappa SEQ ID NOs: 63 64 | GATGTTTTGATGACCCAAACTCCACTCTCCCTGCCTGTCAGTCTTGGAGAT CAAGCCTCCATCTCTTGCAGATCTAGTCAGAGCATTGTACATAGTAATGG AAACACCTATTTAGAATGGTACCTGCGAAACCAGGCCAGTCTCCAAAGCT CCTGATCTACAAAGTTTCCAACCGATTTTCTGGGGTCCCAGACAGGTTCA GTGGCAGTGGATCAGGAACAGATTTCACACTCAAGATCAGCAGAGTGGA GGCTAGGATCTGGGAGTTTATTACTGCTTTCAAGGTTCACATGTTCCTCC GACGTTCGGTGGAGGCTCCAAGCTGGAAATCAAA | DVLMTQTPLSLPVSLGDQA SISCRSSQSIVHSNGNTYLE WYLQKPGQSPKLLIYKVSN RFSGVPDRFSGSGSGTDFTL KISRVEAEDLGVYYCFQGSH VPPTFGGGSKLEIK |
| 2H10 | Heavy-IgG1 SEQ ID NOs: 65, 66 VH2 | CAGGTCCAGCTGCAGCAGTCTGGAACTGAACTGGTGAGGCCTGGGACTT CAGTGAAGGTGTCCTGCAAGGCTTCTGGATACGCCTTCACTAATTACTTG ATAGAGTGGGTAAAGCAGAGGCCTGGACGGGCCTTGAGTGGATTGGAG TGATTAATCCTGGAAGTGGTGGTACTAGGTACAATGAGAAGTTCAAGGG CAAGGCAACACTGACTGCAGACAAATCCTCCACCACTGCCCACATGCAGC TCAGCAGCTGACATCTGATGACTCTGCGGTCTATTTCTGTGCAAGATGGG GGGGAAACTACTCTGGCTATGCTATGGACTACTGGGGTCAAGGAACCTC AGTCACCGTCTCCTCA | QVQLQQSGTELVRPGTSVK VSCKASGYAFTNYLIEWVK QRPGQGLEWIGVINPGSG GTRYNEKFKGKATLTADKSS TTAHMQLSSLTSDDSAVYF CARWGGNYSGYAMDYW GQGTSVIVSS |
| | Light-Kappa SEQ ID NOs: 63 64 | GATGTTTTGATGACCCAAACTCCACTCTCCCTGCCTGTCAGTCTTGGAGAT CAAGCCTCCATCTCTTGCAGATCTAGTCAGAGCATTGTACATAGTAATGG AAACACCTATTTAGAATGGTACCTGCGAAACCAGGCCAGTCTCCAAAGCT CCTGATCTACAAAGTTTCCAACCGATTTTCTGGGGTCCCAGACAGGTTCA GTGGCAGTGGATCAGGAACAGATTTCACACTCAAGATCAGCAGAGTGGA GGCTAGGATCTGGGAGTTTATTACTGCTTTCAAGGTTCACATGTTCCTCC GACGTTCGGTGGAGGCTCCAAGCTGGAAATCAAA | DVLMTQTPLSLPVSLGDQA SISCRSSQSIVHSNGNTYLE WYLQKPGQSPKLLIYKVSN RFSGVPDRFSGSGSGTDFTL KISRVEAEDLGVYYCFQGSH VPPTFGGGSKLEIK |

Two heavy chains were identified for antibody 2H10 which are labelled VH1 and VH2.

Whether one or both heavy chains produce antibodies selective for its cyclic peptide immunogen, can be confirmed by expressing each heavy chain (or variable region) with the light chain (or variable region) and assessing target binding.

Antibody 2H10-VH1 heavy chain alignment is more closely related to the heavy chains for 6C5 and 9C5 compared to 2H10-V2.

Example 10

Immunofluorescent Staining of TDP-43 Using Antibody 9C5

Misfolded TDP-43 was recombinantly expressed using the construct and protocol described in Example 7 with the following modifications to reduce background. The primary and secondary antibodies were spun for 10 min at 10000 RPM prior to use, and the sections were blocked with 10% NGS for 1 hour at RT prior to primary addition. DAPI stain is used to identify the nucleus.

Figure 12A:
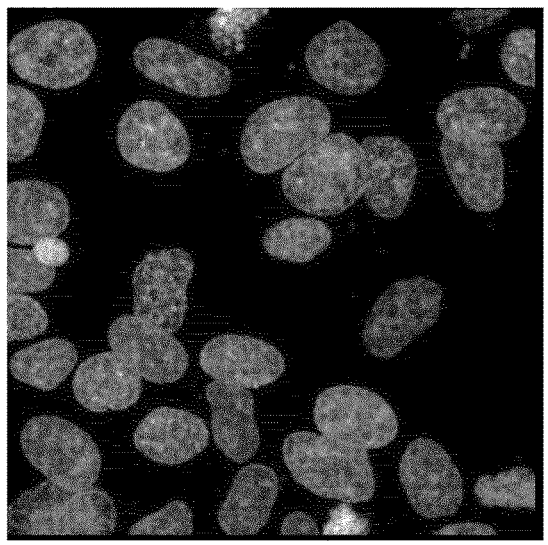
Figure 12B:
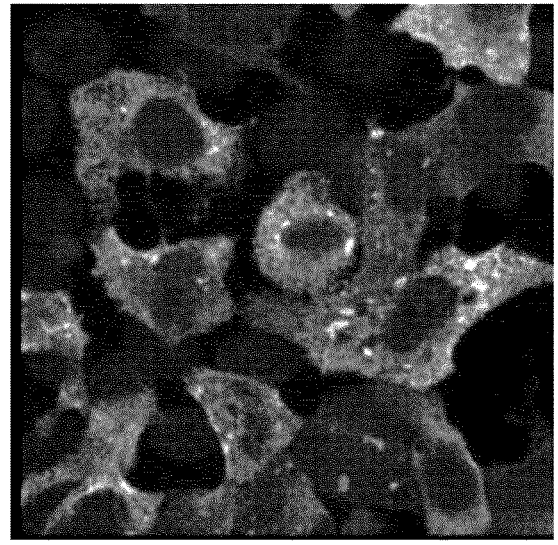
Figure 12C:
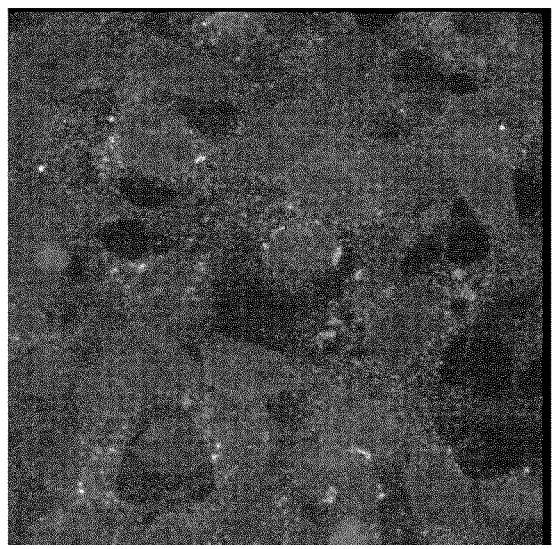
Figure 12D:
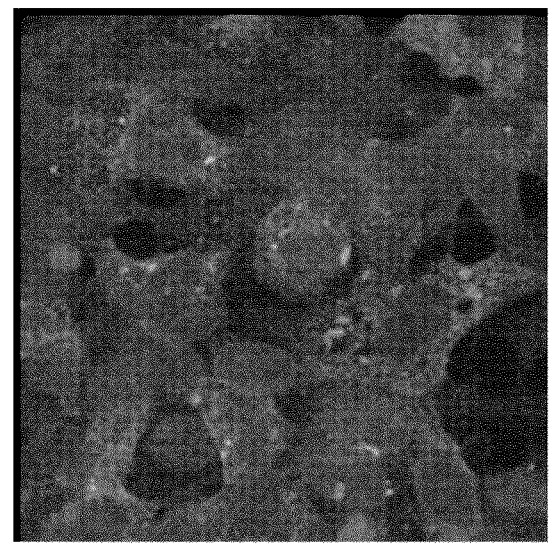

As shown in FIG. 12C, 9C5 antibody detected TDP-43 cytoplasmic inclusions of misfolded TDP-43. FIG. 12A shows DAPI stained cells confirming that the TDP43 detected is cytoplasmic. Staining was also performed for HA (FIG. 12B) as the TDP-43 recombinantly expressed is HA tagged which primarily colocalized with 9C5 staining (FIG. 12D).

TABLE 11

Epitope and Cyclic Compound Sequences

1. TTEQ (SEQ ID NO: 1)
2. CGGTTEQGG, cyclo (CGGTTEQGG) (SEQ ID NO: 2)
3. CGTTEQG, cyclo (CGTTEQG) (SEQ ID NO: 3)
4. GTTEQG (SEQ ID NO: 4)
5. TTEQG (SEQ ID NO: 5)
6. GTTEQ (SEQ ID NO: 6)
7. KTTEQD (SEQ ID NO: 7)
8. TEQD (SEQ ID NO: 8)
9. TTEQD (SEQ ID NO: 9)
10. KTTE (SEQ ID NO: 10)
11. TTEQDL (SEQ ID NO: 11)
12. KTTEQ (SEQ ID NO: 12)
13. CGTTEQGC, cyclic (CGTTEQGC) (SEQ ID NO: 13)
14. KTTEQDL (SEQ ID NO: 14)
15. TEQDLK (SEQ ID NO: 15)
16. TEQDLKE (SEQ ID NO: 16)
17. TEQDLKEY (SEQ ID NO: 17)

TABLE 11-continued

Epitope and Cyclic Compound Sequences

18. TEQDLKEYF (SEQ ID NO: 18)
19. EQDL (SEQ ID NO: 19)
20. WKTTEQ (SEQ ID NO: 20)
21. TTEQDLKEYFSTFGEV (SEQ ID NO: 21)
22. CGGTTEQGGG, cyclo (CGGTTEQGGG) (SEQ ID NO: 22)
23. CGTTEQGG, cyclo(CGTTEQGG) (SEQ ID NO: 23)
24. C-PEG2-TTEQG, cyclo (C-PEG2-TTEQG), CTTEQG (SEQ ID NO: 24)
25. C-PEG2-TTEQGG, cyclo (C-PEG2-TTEQGG), CTTEQGG (SEQ ID NO: 25)
26. CGTTEQ-PEG2, cyclo (CGTTEQ-PEG2), CGTTEQ (SEQ ID NO: 26)
27. CGGTTEQ-PEG2, cyclo1(CGTTEQ-PEG2), CGTTEQ (SEQ ID NO: 27)
28. CGTTEG, cyclo (CGTTEG) (SEQ ID NO: 28)
29. CGTTEGG, cyclo (CGTTEGG), (SEQ ID NO: 29)
30. CGGTTEGG, cyclo (CGGTTEGG), (SEQ ID NO: 30)
31. CGGGTTEGG, cyclo (CGGGTTEGG), (SEQ ID NO: 31)
32. CGGTTEGGG, cyclo (CGGTTEGGG), (SEQ ID NO: 32)
33. CGGGTTEGGG, cyclo (CGGGTTEGGG), (SEQ ID NO: 33)
34. CGGGGTTEGGG, cyclo (CGGGGTTEGGG), (SEQ ID NO: 34)
35. CGGGGTTEGGGG, cyclo (CGGGGTTEGGGG), (SEQ ID NO: 35)
36. C-PEG2-TTEG, cyclo (C-PEG2-TTEG), CTTEG (SEQ ID NO: 36)
37. C-PEG2-TTEGG, cyclo (C-PEG2-TTEGG), CTTEGG (SEQ ID NO: 37)
38. CGTTE-PEG2, cyclo (CGTTE-PEG2), CGTTE (SEQ ID NO: 38)
39. CGGTTE-PEG2, cyclo1 (CGGTTE-PEG2), CGGTTE (SEQ ID NO: 39)
40. GGCGG (SEQ ID NO: 40)
41. GCGG (SEQ ID NO: 41)
42. CGGGTTEQGG, cyclo (CGGGTTEQGG), (SEQ ID NO: 42)
43. CGGGGTTEQGGG, cyclo (CGGGGTTEQGGG), (SEQ ID NO: 43)
44. CGGGGGTTEQGGGG, cyclo (CGGGGTTEQGGGG), (SEQ ID NO: 44)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

[1] Kuo P H, Chiang C H, Wnag Y T, Doudeva L G, Yuan H S, The Crystal Structure of TDP-43 RRM1-DNA Complex Reveals the Specific Recognition for UG- and TG-Rich Nucleic Acids. *Nucleic Acids Res.*, 2014, vol 42, 4712.

[2] DOI: 10.2210/pdb1wf0/pdb (No publication).

[3] Mompean, M., Romano, V., Pantoja-Uceda, D., Stuani, C., Baralle, F. E., Buratti, E., and Laurents, D. V. The TDP-43 N-Terminal Domain Structure at High Resolution. *FEBS J.*, 2016, 283, 1242.

[4] Arai, T., Hasegawa, M., Akiyama, H., Ikeda, K., Nonaka, T., Mori, H., Mann, D., Tsuchiya, K., Yoshida, M., Hashizume, Y., and Oda, T. TDP-43 is a component of ubiquitin-positive tau-negative inclusions in frontotemporal lobar degeneration and amyotrophic lateral sclerosis. *Biochem. Biophys. Res. Commun.*, 2006, 351, 602-611.

[5] Chantelle F. Sephton, Shannon K. Good, Stan Atkin, Colleen M. Dewey, Paul Mayer III, Joachim Herz, and Gang Yu *J. Biol. Chem.* 2010, vol. 285, No. 9, 6826-6834.

[6] Abel, O., Powell, J. F., Andersen, P. M., and Al-Chalabi, A. *Hum Mutat*, 2012, 33:1345-51.

[7] Hamley, I. W. *PEG-Peptide Conjugates* 2014; 15, 1543-1559; dx.doi.org/10.1021/bm500246w

[8] Roberts, M J et al *Chemistry for peptide and protein PEGylation* 64: 116-127.

The invention claimed is:

1. An antibody that selectively binds TDP-43, wherein the antibody comprises a light chain variable region and a heavy chain variable region, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

| | | | |
|---|---|---|---|
| A) | | CDR-H1: GYTFTDYS; | SEQ ID NO: 67 |
| | | CDR-H2: INTETGEP; | SEQ ID NO: 68 |
| | | CDR-H3: ASRRWYPYYFDY; | SEQ ID NO: 69 |
| | | CDR-L1: TGAVTTSNY; | SEQ ID NO: 70 |
| | | CDR-L2: GPN; and | SEQ ID NO: 71 |
| | | CDR-L3: ALWYSNHWV; | SEQ ID NO: 72 |
| or | | | |
| B) | | CDR-H1: GFTFSDYY; | SEQ ID NO: 73 |
| | | CDR-H2: ISNGGGST; | SEQ ID NO: 74 |
| | | CDR-H3: AREGGTAWFAY; | SEQ ID NO: 75 |
| | | CDR-L1: QSIVHSNGNTY; | SEQ ID NO: 76 |
| | | CDR-L2: KVS; and | SEQ ID NO: 77 |
| | | CDR-L3: FQGSHVPYT; | SEQ ID NO: 78 |
| or | | | |
| C) | | CDR-H1: GFTFSDYY; | SEQ ID NO: 73 |
| | | CDR-H2: ISDGGSYT; | SEQ ID NO: 79 |
| | | CDR-H3: ARDYYGSSSYTSGFAY; | SEQ ID NO: 80 |
| | | CDR-L1: QSIVHSNGNTY; | SEQ ID NO: 76 |
| | | CDR-L2: KVS; and | SEQ ID NO: 77 |
| | | CDR-L3: FQGSHVPGT; | SEQ ID NO: 81 |
| or | | | |
| D) | | CDR-H1: GYTFTDYS; | SEQ ID NO: 67 |
| | | CDR-H2: INTETGEP; | SEQ ID NO: 68 |
| | | CDR-H3: ARGYGNWFAY; | SEQ ID NO: 82 |
| | | CDR-L1: SSVSSSY; | SEQ ID NO: 83 |
| | | CDR-L2: STS; and | SEQ ID NO: 84 |
| | | CDR-L3: HQYHRSPLT; | SEQ ID NO: 85 |
| or | | | |
| E) | | CDR-H1: GFTFSDFY; | SEQ ID NO: 86 |
| | | CDR-H2: SRSKAHDYTT; and | SEQ ID NO: 87 |
| | | CDR-H3: ARDTWYGSWFAY; | SEQ ID NO: 88 |
| | | CDR-L1: QSIVHSNGNTY; | SEQ ID NO: 76 |
| | | CDR-L2: KVS; and | SEQ ID NO: 77 |
| | | CDR-L3: FQGSHVPPT; | SEQ ID NO: 92 |
| or | | | |
| F) | | CDR-H1: GYAFTNYL; | SEQ ID NO: 89 |
| | | CDR-H2: INPGSGGT; and | SEQ ID NO: 90 |
| | | CDR-H3: ARWGGNYSGYAMDY; | SEQ ID NO: 91 |
| | | CDR-L1: QSIVHSNGNTY; | SEQ ID NO: 76 |
| | | CDR-L2: KVS; and | SEQ ID NO: 77 |
| | | CDR-L3: FQGSHVPPT | SEQ ID NO: 92. |

2. The antibody of claim 1, wherein the antibody selectively binds misfolded TDP-43 polypeptide compared to native TDP-43 polypeptide.

3. The antibody of claim 2, wherein the antibody is at least 2 fold, 3 fold, at least 5 fold, at least 10 fold or at least 20 fold more selective for misfolded TDP-43 polypeptide compared to native TDP-43 polypeptide.

4. The antibody of claim 1, wherein the antibody comprises:
 a) a heavy chain variable region comprising: i) the amino acid sequence as set forth in SEQ ID NO: 46; ii) an amino acid sequence with at least 80% sequence identity to SEQ ID NO: 46, wherein the CDR sequences are as set forth in SEQ ID NO: 67, 68 and 69, or iii) a conservatively substituted amino acid sequence of i), wherein the CDR sequences are as set forth in SEQ ID NO: 67, 68 and 69; and/or wherein the antibody comprises a light chain variable region comprising i) the amino acid sequence as set forth in SEQ ID NO: 48, ii) an amino acid sequence with at least 80% sequence identity to SEQ ID NO: 48, wherein the CDR sequences are as set forth in SEQ ID NO: 70, 71 and 72, or iii) a conservatively substituted amino acid sequence of i), wherein the CDR sequences are as set forth in SEQ ID NO: 70, 71 and 7;
 b) a heavy chain variable region comprising: i) the amino acid sequence as set forth in SEQ ID NO: 50; ii) an amino acid sequence with at least 80% sequence identity to SEQ ID NO: 50, wherein the CDR sequences are as set forth in SEQ ID NO: 73, 74 and 75, or iii) a conservatively substituted amino acid sequence of i), wherein the CDR sequences are as set forth in SEQ ID NO: 73, 74 and 75; and/or wherein the antibody comprises a light chain variable region comprising i) the amino acid sequence as set forth in SEQ ID NO: 52, ii) an amino acid sequence with at least 80% sequence identity to SEQ ID NO: 52, wherein the CDR sequences are as set forth in SEQ ID NO: 76, 77 and 78, or iii) a conservatively substituted amino acid sequence of i), wherein the CDR sequences are as set forth in SEQ ID NO: 76, 77 and 78;
 c) a heavy chain variable region comprising: i) the amino acid sequence as set forth in SEQ ID NO: 54; ii) an amino acid sequence with at least 80% sequence identity to SEQ ID NO: 54, wherein the CDR sequences are as set forth in SEQ ID NO: 73, 79 and 80, or iii) a conservatively substituted amino acid sequence of i), wherein the CDR sequences are as set forth in SEQ ID NO: 73, 79 and 80; and/or wherein the antibody comprises a light chain variable region comprising i) the amino acid sequence as set forth in SEQ ID NO: 56, ii) an amino acid sequence with at least 80% sequence identity to SEQ ID NO: 56, wherein the CDR sequences are as set forth in SEQ ID NO: 76, 77 and 81, or iii) a conservatively substituted amino acid sequence of i), wherein the CDR sequences are as set forth in SEQ ID NO: 76, 77 and 81;
 d) a heavy chain variable region comprising: i) the amino acid sequence as set forth in SEQ ID NO: 58; ii) an amino acid sequence with at least 80% sequence identity to SEQ ID NO: 58, wherein the CDR sequences are as set forth in SEQ ID NO: 67, 68 and 82, or iii) a conservatively substituted amino acid sequence of i), wherein the CDR sequences are as set forth in SEQ ID NO: 67, 68 and 82; and/or wherein the antibody comprises a light chain variable region comprising i) the amino acid sequence as set forth in SEQ ID NO: 60, ii) an amino acid sequence with at least 80% sequence identity to SEQ ID NO: 60, wherein the CDR sequences are as set forth in SEQ ID NO: 83, 84 and 85, or iii) a conservatively substituted amino acid sequence of i), wherein the CDR sequences are as set forth in SEQ ID NO: 83, 84 and 85;
 e) a heavy chain variable region comprising: i) the amino acid sequence as set forth in SEQ ID NO: 62; ii) an amino acid sequence with at least 80% sequence identity to SEQ ID NO: 62, wherein the CDR sequences are as set forth in SEQ ID NO: 86, 87 and 88, or iii) a conservatively substituted amino acid sequence of i), wherein the CDR sequences are as set forth in SEQ ID NO: 86, 87 and 88; and/or wherein the antibody comprises a light chain variable region comprising i) the amino acid sequence as set forth in SEQ ID NO: 64, ii) an amino acid sequence with at least 80% sequence identity to SEQ ID NO: 64, wherein the CDR sequences are as set forth in SEQ ID NO: 76, 77 and 92, or iii) a conservatively substituted amino acid sequence of i), wherein the CDR sequences are as set forth in SEQ ID NO: 76, 77 and 92; or
 f) a heavy chain variable region comprises: i) the amino acid sequence as set forth in SEQ ID NO: 66; ii) an amino acid sequence with at least 80% sequence identity to SEQ ID NO: 66, wherein the CDR sequences are as set forth in SEQ ID NO: 89, 90 and 91, or iii) a conservatively substituted amino acid sequence of i), wherein the CDR sequences are as set forth in SEQ ID NO: 89, 90 and 91; and/or wherein the antibody comprises a light chain variable region comprising i) the amino acid sequence as set forth in SEQ ID NO: 64, ii) an amino acid sequence with at least 80% sequence identity to SEQ ID NO: 64, wherein the CDR sequences are as set forth in SEQ ID NO: 76, 77 and 92, or iii) a conservatively substituted amino acid sequence of i), wherein the CDR sequences are as set forth in SEQ ID NO: 76, 77 and 92.

5. The antibody of claim 4, wherein
 a) the heavy chain variable region comprises the amino acid sequence as set forth in SEQ ID NO: 46 and/or the light chain variable region comprises the amino acid sequence as set forth in SEQ ID NO: 48;
 b) the heavy chain variable region comprises the amino acid sequence as set forth in SEQ ID NO: 50 and/or the light chain variable region comprises the amino acid sequence as set forth in SEQ ID NO: 52;
 c) the heavy chain variable region comprises the amino acid sequence as set forth in SEQ ID NO: 54 and/or the light chain variable region comprises the amino acid sequence as set forth in SEQ ID NO: 56;
 d) the heavy chain variable region comprises the amino acid sequence as set forth in SEQ ID NO: 58 and/or the light chain variable region comprises the amino acid sequence as set forth in SEQ ID NO: 60;
 e) the heavy chain variable region comprises the amino acid sequence as set forth in SEQ ID NO: 62 and/or the light chain variable region comprises the amino acid sequence as set forth in SEQ ID NO: 64; or
 f) the heavy chain variable region comprises the amino acid sequence as set forth in SEQ ID NO: 66 and/or the light chain variable region comprises the amino acid sequence as set forth in SEQ ID NO: 64.

6. The antibody of claim 1, wherein the antibody is a monoclonal antibody, humanized antibody and/or single chain antibody.

7. The antibody of claim 1, wherein the antibody is a binding fragment selected from Fab, Fab', F(ab')2, scFv, dsFv, ds-scFv, dimers, nanobodies, minibodies, diabodies, and multimers thereof.

8. An immunoconjugate comprising the antibody of claim 1 and a detectable label or a transport moiety that facilitates transport across the blood brain barrier and/or into a cell.

9. A nucleic acid encoding i) an antibody or ii) an immunoconjugate that is a polypeptide comprising said antibody, the antibody comprising a light chain variable region and a heavy chain variable region, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

| A) | CDR-H1: GYTFTDYS; | SEQ ID NO: 67 |
|---|---|---|
| | CDR-H2: INTETGEP; | SEQ ID NO: 68 |
| | CDR-H3: ASRRWYPYYFDY; | SEQ ID NO: 69 |
| | CDR-L1: TGAVTTSNY; | SEQ ID NO: 70 |
| | CDR-L2: GPN; and | SEQ ID NO: 71 |
| | CDR-L3: ALWYSNHWV; | SEQ ID NO: 72 |
| or | | |
| B) | CDR-H1: GFTFSDYY; | SEQ ID NO: 73 |
| | CDR-H2: ISNGGGST; | SEQ ID NO: 74 |
| | CDR-H3: AREGGTAWFAY; | SEQ ID NO: 75 |
| | CDR-L1: QSIVHSNGNTY; | SEQ ID NO: 76 |
| | CDR-L2: KVS; and | SEQ ID NO: 77 |
| | CDR-L3: FQGSHVPYT; | SEQ ID NO: 78 |
| or | | |
| C) | CDR-H1: GFTFSDYY; | SEQ ID NO: 73 |
| | CDR-H2: ISDGGSYT; | SEQ ID NO: 79 |
| | CDR-H3: ARDYYGSSSYTSGFAY; | SEQ ID NO: 80 |
| | CDR-L1: QSIVHSNGNTY; | SEQ ID NO: 76 |
| | CDR-L2: KVS; and | SEQ ID NO: 77 |
| | CDR-L3: FQGSHVPGT | SEQ ID NO: 81 |
| or | | |
| D) | CDR-H1: GYTFTDYS; | SEQ ID NO: 67 |
| | CDR-H2: INTETGEP; | SEQ ID NO: 68 |
| | CDR-H3: ARGYGNWFAY; | SEQ ID NO: 82 |
| | CDR-L1: SSVSSSY; | SEQ ID NO: 83 |
| | CDR-L2: STS; and | SEQ ID NO: 84 |
| | CDR-L3: HQYHRSPLT; | SEQ ID NO: 85 |
| or | | |
| E) | CDR-H1: GFTFSDFY; | SEQ ID NO: 86 |
| | CDR-H2: SRSKAHDYTT; and | SEQ ID NO: 87 |
| | CDR-H3: ARDTWYGSWFAY; | SEQ ID NO: 88 |
| | CDR-L1: QSIVHSNGNTY; | SEQ ID NO: 76 |
| | CDR-L2: KVS; and | SEQ ID NO: 77 |
| | CDR-L3: FQGSHVPPT; | SEQ ID NO: 92 |
| or | | |
| F) | CDR-H1: GYAFTNYL; | SEQ ID NO: 89 |
| | CDR-H2: INPGSGGT; and | SEQ ID NO: 90 |
| | CDR-H3: ARWGGNYSGYAMDY; | SEQ ID NO: 91 |
| | CDR-L1: QSIVHSNGNTY; | SEQ ID NO: 76 |
| | CDR-L2: KVS; and | SEQ ID NO: 77 |
| | CDR-L3: FQGSHVPPT | SEQ ID NO: 92. |

10. A cell expressing the antibody of claim 1.

11. A composition comprising the antibody of claim 1, an immunoconjugate comprising said antibody or a cell expressing said antibody.

12. A kit comprising the antibody of claim 1, an immunoconjugate comprising said antibody or a cell expressing said antibody.

13. A method of making the antibody of claim 1, comprising administering an immunogen comprising a cyclic compound comprising: a TDP-43 peptide comprising: 1) TTE, 2) TTEQ (SEQ ID NO:1) or 3) TEQ and up to 6 TDP-43 contiguous residues, and a linker, wherein the linker is covalently coupled to the TDP-43 peptide N-terminus residue and the peptide C-terminus residue, wherein at least one amino acid in the TDP-43 peptide is an alternate conformation than T, E, and/or Q in a corresponding linear and/or native TDP-43 or a composition comprising said immunogen to a subject and isolating antibody and/or cells expressing antibody selective for the TDP-43 peptide in the cyclic compound of the immunogen administered.

14. A method of determining if a sample suspected of comprising misfolded TDP-43 polypeptides contains misfolded TDP-43 polypeptide the method comprising:

a) contacting the sample with the antibody of claim 1 under conditions permissive for forming an antibody: misfolded TDP-43 polypeptide complex; and
b) detecting the presence of any complex;
wherein the presence of detectable complex is indicative that the sample may contain misfolded TDP-43 polypeptide.

15. The method of claim 14, wherein the sample comprises brain tissue extract, spinal cord tissue or cerebrospinal fluid (CSF).

16. The antibody of claim 1, wherein the antibody comprises:
a) a heavy chain variable region comprising: i) the amino acid sequence as set forth in SEQ ID NO: 46; ii) an amino acid sequence with at least 90% or at least 90% sequence identity to SEQ ID NO: 46, wherein the CDR sequences are as set forth in SEQ ID NO: 67, 68 and 69, or iii) a conservatively substituted amino acid sequence of i), wherein the CDR sequences are as set forth in SEQ ID NO: 67, 68 and 69; and/or wherein the antibody comprises a light chain variable region comprising i) the amino acid sequence as set forth in SEQ ID NO: 48, ii) an amino acid sequence with at least 90% or at least 90% sequence identity to SEQ ID NO: 48, wherein the CDR sequences are as set forth in SEQ ID NO: 70, 71 and 72, or iii) a conservatively substituted amino acid sequence of i), wherein the CDR sequences are as set forth in SEQ ID NO: 70, 71 and 72;
b) a heavy chain variable region comprising: i) the amino acid sequence as set forth in SEQ ID NO: 50; ii) an amino acid sequence with at least 90% or at least 90% sequence identity to SEQ ID NO: 50, wherein the CDR sequences are as set forth in SEQ ID NO: 73, 74 and 75, or iii) a conservatively substituted amino acid sequence of i), wherein the CDR sequences are as set forth in SEQ ID NO: 73, 74 and 75; and/or wherein the antibody comprises a light chain variable region comprising i) the amino acid sequence as set forth in SEQ ID NO: 52, ii) an amino acid sequence with at least 90% or at least 90% sequence identity to SEQ ID NO: 52, wherein the CDR sequences are as set forth in SEQ ID NO: 76, 77 and 78, or iii) a conservatively substituted amino acid sequence of i), wherein the CDR sequences are as set forth in SEQ ID NO: 76, 77 and 78;
c) a heavy chain variable region comprising: i) the amino acid sequence as set forth in SEQ ID NO: 54; ii) an amino acid sequence with at least 90% or at least 90% sequence identity to SEQ ID NO: 54, wherein the CDR sequences are as set forth in SEQ ID NO: 73, 79 and 80, or iii) a conservatively substituted amino acid sequence of i), wherein the CDR sequences are as set forth in SEQ ID NO: 73, 79 and 80; and/or wherein the antibody comprises a light chain variable region comprising i) the amino acid sequence as set forth in SEQ ID NO: 56, ii) an amino acid sequence with at least 90% or at least 90% sequence identity to SEQ ID NO: 56, wherein the CDR sequences are as set forth in SEQ ID NO: 76, 77 and 81, or iii) a conservatively substituted amino acid sequence of i), wherein the CDR sequences are as set forth in SEQ ID NO: 76, 77 and 81;
d) a heavy chain variable region comprising: i) the amino acid sequence as set forth in SEQ ID NO: 58; ii) an amino acid sequence with at least 90% or at least 90% sequence identity to SEQ ID NO: 58, wherein the CDR sequences are as set forth in SEQ ID NO: 67, 68 and 82, or iii) a conservatively substituted amino acid sequence of i), wherein the CDR sequences are as set forth in SEQ ID NO: 67, 68 and 82; and/or wherein the antibody comprises a light chain variable region comprising i) the amino acid sequence as set forth in SEQ ID NO: 60, ii) an amino acid sequence with at least 90% or at least 90% sequence identity to SEQ ID NO: 60, wherein the CDR sequences are as set forth in SEQ ID NO: 83, 84 and 85, or iii) a conservatively substituted amino acid sequence of i), wherein the CDR sequences are as set forth in SEQ ID NO: 83, 84 and 85;

e) a heavy chain variable region comprising: i) the amino acid sequence as set forth in SEQ ID NO: 62; ii) an amino acid sequence with at least 90% or at least 90% sequence identity to SEQ ID NO: 62, wherein the CDR sequences are as set forth in SEQ ID NO: 86, 87 and 88, or iii) a conservatively substituted amino acid sequence of i), wherein the CDR sequences are as set forth in SEQ ID NO: 86, 87 and 88; and/or wherein the antibody comprises a light chain variable region comprising i) the amino acid sequence as set forth in SEQ ID NO: 64, ii) an amino acid sequence with at least 90% or at least 90% sequence identity to SEQ ID NO: 64, wherein the CDR sequences are as set forth in SEQ ID NO: 76, 77 and 92, or iii) a conservatively substituted amino acid sequence of i), wherein the CDR sequences are as set forth in SEQ ID NO: 76, 77 and 92; or f) a heavy chain variable region comprises: i) the amino acid sequence as set forth in SEQ ID NO: 66; ii) an amino acid sequence with at least 90% or at least 90% sequence identity to SEQ ID NO: 66, wherein the CDR sequences are as set forth in SEQ ID NO: 89, 90 and 91, or iii) a conservatively substituted amino acid sequence of i), wherein the CDR sequences are as set forth in SEQ ID NO: 89, 90 and 91; and/or wherein the antibody comprises a light chain variable region comprising i) the amino acid sequence as set forth in SEQ ID NO: 64, ii) an amino acid sequence with at least 90% or at least 90% sequence identity to SEQ ID NO: 64, wherein the CDR sequences are as set forth in SEQ ID NO: 76, 77 and 92, or iii) a conservatively substituted amino acid sequence of i), wherein the CDR sequences are as set forth in SEQ ID NO: 76, 77 and 92.

17. A composition comprising the nucleic acid of claim 9.

18. A kit comprising the nucleic acid of claim 9.

19. The antibody of claim 1, wherein the light chain variable region and the heavy chain variable region are fused.

20. The antibody of claim 1, wherein the light chain variable region is encoded by an expression vector and the heavy chain variable region is encoded by another expression vector.

21. The antibody of claim 1, wherein:
a) the heavy chain variable region amino acid sequence is encoded by the nucleotide sequence as set out in SEQ ID NO: 45 or a codon degenerate or optimized version thereof and/or wherein the light chain variable region amino acid sequence is encoded by the nucleotide sequence as set out in SEQ ID NO: 47 or a codon degenerate or optimized version thereof;
b) the heavy chain variable region amino acid sequence is encoded by the nucleotide sequence as set out in SEQ ID NO: 49 or a codon degenerate or optimized version thereof and/or the light chain variable region amino acid sequence is encoded by the nucleotide sequence as set out in SEQ ID NO: 51 or a codon degenerate or optimized version thereof;
c) the heavy chain variable region amino acid sequence is encoded by the nucleotide sequence as set out in SEQ ID NO: 53 or a codon degenerate or optimized version thereof and/or the light chain variable region amino acid sequence is encoded by the nucleotide sequence as set out in SEQ ID NO: 55 or a codon degenerate or optimized version thereof;
d) the heavy chain variable region amino acid sequence is encoded by the nucleotide sequence as set out in SEQ ID NO: 57 or a codon degenerate or optimized version thereof and/or the light chain variable region amino acid sequence is encoded by the nucleotide sequence as set out in SEQ ID NO: 59 or a codon degenerate or optimized version thereof;
e) the heavy chain variable region amino acid sequence is encoded by the nucleotide sequence as set out in SEQ ID NO: 61 or a codon degenerate or optimized version thereof and/or the light chain variable region amino acid sequence is encoded by a nucleotide sequence as set out in SEQ ID NO: 63 or a codon degenerate or optimized version thereof; or
f) the heavy chain variable region amino acid sequence is encoded by the nucleotide sequence as set out in SEQ ID NO: 65 or a codon degenerate or optimized version thereof and/or the light chain variable region amino acid sequence is encoded by the nucleotide sequence as set out in SEQ ID NO: 63 or a codon degenerate or optimized version thereof.

22. The antibody of claim 16, wherein:
a) the heavy chain variable region amino acid sequence is encoded by the nucleotide sequence as set out in SEQ ID NO: 45 or a codon degenerate or optimized version thereof and/or wherein the light chain variable region amino acid sequence is encoded by the nucleotide sequence as set out in SEQ ID NO: 47 or a codon degenerate or optimized version thereof;
b) the heavy chain variable region amino acid sequence is encoded by the nucleotide sequence as set out in SEQ ID NO: 49 or a codon degenerate or optimized version thereof and/or the light chain variable region amino acid sequence is encoded by the nucleotide sequence as set out in SEQ ID NO: 51 or a codon degenerate or optimized version thereof;
c) the heavy chain variable region amino acid sequence is encoded by the nucleotide sequence as set out in SEQ ID NO: 53 or a codon degenerate or optimized version thereof and/or the light chain variable region amino acid sequence is encoded by the nucleotide sequence as set out in SEQ ID NO: 55 or a codon degenerate or optimized version thereof;
d) the heavy chain variable region amino acid sequence is encoded by the nucleotide sequence as set out in SEQ ID NO: 57 or a codon degenerate or optimized version thereof and/or the light chain variable region amino acid sequence is encoded by the nucleotide sequence as set out in SEQ ID NO: 59 or a codon degenerate or optimized version thereof;
e) the heavy chain variable region amino acid sequence is encoded by the nucleotide sequence as set out in SEQ ID NO: 61 or a codon degenerate or optimized version thereof and/or the light chain variable region amino acid sequence is encoded by a nucleotide sequence as set out in SEQ ID NO: 63 or a codon degenerate or optimized version thereof; or
f) the heavy chain variable region amino acid sequence is encoded by the nucleotide sequence as set out in SEQ ID NO: 65 or a codon degenerate or optimized version thereof and/or the light chain variable region amino acid sequence is encoded by the nucleotide sequence as set out in SEQ ID NO: 63 or a codon degenerate or optimized version thereof.

23. The nucleic acid of claim 9, wherein the light chain variable region and the heavy chain variable region are fused.

24. The cell of claim 10, wherein the cell is a hybridoma.

25. The method of claim 15, wherein the sample is from a subject with or suspected of having amyotrophic lateral sclerosis (ALS) or frontotemporal dementia (FTD).

26. The composition of claim 17, wherein the light chain variable region is encoded by a vector and the heavy chain variable region is encoded by another vector.

* * * * *